(12) United States Patent
Llinas-Brunet et al.

(10) Patent No.: US 7,642,235 B2
(45) Date of Patent: Jan. 5, 2010

(54) MACROCYCLIC PEPTIDES ACTIVE AGAINST THE HEPATITIS C VIRUS

(75) Inventors: Montse Llinas-Brunet, Dollard-Des-Ormeaux (CA); Murray Bailey, Pierrefonds (CA); Punit Bhardwaj, Laval (CA); Elise Ghiro, Laval (CA); Nathalie Goudreau, St-Laurent (CA); Teddy Halmos, Laval (CA)

(73) Assignee: Boehringer Ingelheim International GmbH, Ingelheim (DE)

( * ) Notice: Subject to any disclaimer, the term of this patent is extended or adjusted under 35 U.S.C. 154(b) by 404 days.

(21) Appl. No.: 10/945,518

(22) Filed: Sep. 20, 2004

(65) Prior Publication Data

US 2005/0080005 A1    Apr. 14, 2005

Related U.S. Application Data

(60) Provisional application No. 60/504,839, filed on Sep. 22, 2003.

(51) Int. Cl.
| | |
|---|---|
| A61K 38/00 | (2006.01) |
| A61K 31/47 | (2006.01) |
| A61K 38/12 | (2006.01) |
| A01N 43/42 | (2006.01) |
| C07K 5/00 | (2006.01) |
| C07K 7/00 | (2006.01) |
| C07K 16/00 | (2006.01) |
| C07K 17/00 | (2006.01) |

(52) U.S. Cl. .......... 514/10; 514/312; 530/317
(58) Field of Classification Search ........ None
See application file for complete search history.

(56) References Cited

U.S. PATENT DOCUMENTS

| | | | |
|---|---|---|---|
| 3,139,421 A | 6/1964 | Elslager et al. |
| 5,114,918 A | 5/1992 | Ishikawa et al. |
| 5,192,746 A | 3/1993 | Lobl et al. |
| 5,633,388 A | 5/1997 | Diana et al. |
| 5,721,210 A | 2/1998 | Lobl et al. |
| 5,824,784 A | 10/1998 | Kinstler et al. |
| 5,830,888 A | 11/1998 | Getman et al. |
| 5,866,684 A | 2/1999 | Attwood et al. |
| 5,869,253 A | 2/1999 | Draper |
| 6,018,020 A | 1/2000 | Attwood et al. |
| 6,159,938 A | 12/2000 | Gyorkos et al. |
| 6,187,905 B1 | 2/2001 | Hurst et al. |
| 6,323,180 B1 | 11/2001 | Llinas-Brunet et al. |
| 6,534,523 B1 | 3/2003 | Bailey et al. |
| 6,608,027 B1 | 8/2003 | Tsantrizos et al. |
| 6,767,991 B1 | 7/2004 | Llinas-Brunet et al. |
| 6,828,301 B2 | 12/2004 | Chen et al. |
| 6,867,185 B2 | 3/2005 | Campbell et al. |
| 6,869,964 B2 | 3/2005 | Campbell et al. |
| 6,878,722 B2 | 4/2005 | Campbell et al. |
| 7,119,072 B2 | 10/2006 | Llinas-Brunet et al. |
| 7,157,424 B2 | 1/2007 | Chen et al. |
| 7,173,004 B2 | 2/2007 | McPhee et al. |
| 7,504,378 B2 | 3/2009 | Llinas-Brunet et al. |
| 2003/0181363 A1 | 9/2003 | Llinas-Brunet et al. |
| 2003/0224977 A1 | 12/2003 | Llinas-Brunet et al. |
| 2004/0002448 A1 | 1/2004 | Tsantrizos et al. |
| 2004/0038872 A1 | 2/2004 | Campbell et al. |
| 2004/0077551 A1 | 4/2004 | Campbell et al. |
| 2004/0138109 A1 | 7/2004 | Chen et al. |
| 2004/0248779 A1 | 12/2004 | Dersch et al. |
| 2005/0020503 A1 | 1/2005 | Llinas-Brunet et al. |
| 2005/0049187 A1 | 3/2005 | Brandenburg et al. |
| 2005/0075279 A1 | 4/2005 | Llinas-Brunet et al. |
| 2005/0080005 A1 | 4/2005 | Llinas-Brunet et al. |
| 2005/0090432 A1 | 4/2005 | McPhee et al. |
| 2005/0119453 A1 | 6/2005 | Brenner et al. |
| 2005/0154186 A1 | 7/2005 | Gallou et al. |
| 2005/0159345 A1 | 7/2005 | Lamarre et al. |

(Continued)

FOREIGN PATENT DOCUMENTS

| | | |
|---|---|---|
| CA | 2087021 A1 | 1/1992 |
| CA | 2222524 A1 | 1/1997 |

(Continued)

OTHER PUBLICATIONS

WHO. Fact Sheet No. 164. Hepatitis C, Revised Oct. 2000. pp. 1-3. Accessed online at http://www.who.int/mediacentre/factsheets/fs164/en/print.html.*

(Continued)

*Primary Examiner*—Cecilia Tsang
*Assistant Examiner*—Marcela M Cordero Garcia
(74) *Attorney, Agent, or Firm*—Michael P. Morris; Mary-Ellen M. Devlin; Philip I. Datlow

(57) ABSTRACT

Compounds of formula I:

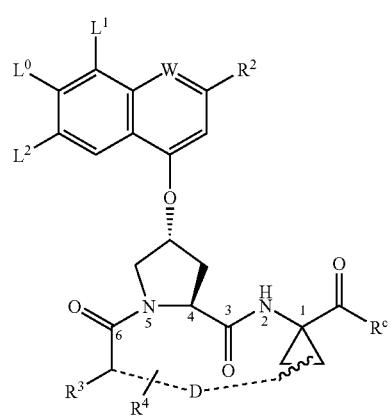

wherein D, $R^4$, $R^3$, $L^0$, $L^1$, $L^2$, $R^2$ and $R^C$ are defined herein; or a pharmaceutically acceptable salt thereof, useful as inhibitors of the HCV NS3 protease.

59 Claims, No Drawings

U.S. PATENT DOCUMENTS

| | | | |
|---|---|---|---|
| 2005/0192212 | A1 | 9/2005 | Llinas-Brunet et al. |
| 2005/0209135 | A1 | 9/2005 | Busacca et al. |
| 2005/0215423 | A1 | 9/2005 | Brenner et al. |
| 2006/0063915 | A1 | 3/2006 | Gallou et al. |
| 2006/0063916 | A1 | 3/2006 | Gallou |
| 2006/0089300 | A1 | 4/2006 | Llinas-Brunet et al. |

FOREIGN PATENT DOCUMENTS

| | | |
|---|---|---|
| EP | 0937459 A2 | 8/1999 |
| EP | 1256628 A2 | 11/2002 |
| GB | 2337262 | 11/1999 |
| JP | 1135478 | 2/1999 |
| JP | 11127861 | 5/1999 |
| JP | 11137252 | 5/1999 |
| JP | 11292840 | 5/1999 |
| JP | 10298151 | 4/2001 |
| JP | 2001103993 | 4/2001 |
| WO | 9200995 A1 | 1/1992 |
| WO | 9415958 A2 | 7/1994 |
| WO | 9533764 A2 | 12/1995 |
| WO | 9701579 A2 | 1/1997 |
| WO | 9706804 A1 | 2/1997 |
| WO | 9950230 A1 | 10/1997 |
| WO | 9743310 A1 | 11/1997 |
| WO | 9817679 A1 | 4/1998 |
| WO | 9822496 A2 | 5/1998 |
| WO | 9846597 A1 | 10/1998 |
| WO | 9846630 A1 | 10/1998 |
| WO | 9853814 A1 | 12/1998 |
| WO | 9907733 A2 | 2/1999 |
| WO | 9907734 A2 | 2/1999 |
| WO | WO 99/07733 | 2/1999 |
| WO | WO 99/07734 | 2/1999 |
| WO | 9938888 A2 | 8/1999 |
| WO | 9964442 A1 | 12/1999 |
| WO | 0006529 A1 | 2/2000 |
| WO | 0009543 A2 | 2/2000 |
| WO | 0009558 A1 | 2/2000 |
| WO | WO 00/09543 | 2/2000 |
| WO | WO 00/09558 | 2/2000 |
| WO | 0020400 A1 | 4/2000 |
| WO | 0031129 A1 | 6/2000 |
| WO | 0059929 A1 | 10/2000 |
| WO | WO 00/59929 | 10/2000 |
| WO | 0102424 A2 | 1/2001 |
| WO | 0107407 A1 | 2/2001 |
| WO | 0116357 A2 | 3/2001 |
| WO | 0132691 A1 | 5/2001 |
| WO | 0140262 A1 | 6/2001 |
| WO | 0147883 A1 | 7/2001 |
| WO | 0158929 A1 | 8/2001 |
| WO | 0164678 A2 | 9/2001 |
| WO | 0174768 A2 | 10/2001 |
| WO | 0177113 A2 | 10/2001 |
| WO | 0181325 A2 | 11/2001 |
| WO | 0185172 A1 | 11/2001 |
| WO | 0190121 A2 | 11/2001 |
| WO | 0206246 A1 | 1/2002 |
| WO | 0208187 A1 | 1/2002 |
| WO | 0208198 A2 | 1/2002 |
| WO | 0208244 A2 | 1/2002 |
| WO | 0208251 A2 | 1/2002 |
| WO | 0208256 A2 | 1/2002 |
| WO | 0218369 A2 | 3/2002 |
| WO | 02057287 A2 | 7/2002 |
| WO | 02057425 A2 | 7/2002 |
| WO | 02060926 A2 | 8/2002 |
| WO | WO 02/060926 A2 | 8/2002 |
| WO | 02069903 A2 | 9/2002 |
| WO | 02079234 A1 | 10/2002 |
| WO | 02098424 A1 | 12/2002 |
| WO | 02100846 A1 | 12/2002 |
| WO | 02100851 A1 | 12/2002 |
| WO | 03000254 A1 | 1/2003 |
| WO | 03007945 A1 | 1/2003 |
| WO | 03010140 A2 | 2/2003 |
| WO | 03010141 A2 | 2/2003 |
| WO | 03026587 A2 | 4/2003 |
| WO | WO 03/099316 A1 | 4/2003 |
| WO | 03053349 A2 | 7/2003 |
| WO | WO 03/053349 A2 | 7/2003 |
| WO | 03064416 A1 | 8/2003 |
| WO | 03064456 A1 | 8/2003 |
| WO | 03066103 A1 | 8/2003 |
| WO | WO 03/064416 A1 | 8/2003 |
| WO | WO 03/064455 A2 | 8/2003 |
| WO | WO 03/064456 A1 | 8/2003 |
| WO | 03099274 A1 | 12/2003 |
| WO | 03099316 A1 | 12/2003 |
| WO | WO 03/099274 A1 | 12/2003 |
| WO | 2004032827 A2 | 4/2004 |
| WO | WO 2004/032827 A2 | 4/2004 |
| WO | 2004039833 A1 | 5/2004 |
| WO | 2004093915 A1 | 11/2004 |
| WO | 2005028501 A1 | 3/2005 |
| WO | 2005046712 A1 | 5/2005 |
| WO | 2005056182 A1 | 6/2005 |

OTHER PUBLICATIONS

Hoofnagle, MD. US Department of Health and Human Services. Dec. 14, 2004. pp. 1-5. Accessed online Apr. 30, 2007 at http://www.hhs.gov/asl/testify/t041214a.html.☐☐.*

Flamm. Chronic Hepatitis C Virus Infection.JAMA, May 14, 2003. Vo.. 289, No. 18, pp. 2413-2417.*

Chen, S. et al.;"Pharmaceutical Compositions for Hepatitis C Viral Protease Inhibitors";U.S. Appl. No. 10/807,023, filed Mar. 23, 2004.

Llinas-Burnet, M. et al.;"Hepatitis C Inhibitor Compounds";U.S. Appl. No. 10/850,101, filed May 20, 2004.

Lamarre, D. et al. An NS3 Protease Inhibitor with Antiviral Effects in Humans Infected with Hepatitis C Virus; Nature (2003) 426, p. 186-189.

Foy, E. et al.;Regulation of Interferon Regulatory Factor-3 by the Hepatitis C Virus Serine Protease;Science Express, Apr. 17, 2003.

Tsantrizos, Y. et al, "Macrocyclic inhibitors of the NS3 protease as Potential Therapeutic Agents of Hepatitis C Virus Infection"; Angewandte Chemie, Internat. Ed., 2003, vol. 42, No. 12, pp. 1356-1360.

Berge et al.; Pharmaceutical Salts; Journal of Pharmaceutical Sciences; Jan. 1977; vol. 66; No. 1; pp. 1-19.

Krchnak et al.; Polymer-Supported Mitsunobu Ether Formation and its Use in Combinatorial Chemistry; Tetrahedron Letters; vol. 36; No. 35; pp. 6193-6196.

Lohmann, et al; Replication of Subgenonnic Hepatitis C Virus RNAs in a Hepatoma Cell Line; Science; Jul. 2, 1999; vol. 285; pp. 110-113.

Miller, et al; Application of Ring-Closing Methathesis to the Synthesis of Rigidified Amino Acids and Peptides; Journal of American Chemical Society; 1996; vol. 118; pp. 9606-9614.

Mitsunobu; The Use of Diethyl Azodicarboxylate and Triphenylphosphine in Synthesis and Transformation of Natural Products; Synthesis (Reviews); pp. 1-28.

Rano, et al; Solid Phase Synthesis of Aryl Ethers via the Mitsunobu Reaction; Tetrahedron Letters; 1995; vol. 36; No. 22; pp. 3789-3792.

Still, et al; Rapid Chromatographic Technique for Preparative Separations with Moderate Resolution; Journal of Organic Chemistry; 1978; vol. 43; No. 14.

Derwent Abstract: AN 2001-435746 [47] (JP2001103993).

Derwent Abstract: AN 1999-040664 [04] (JP10298151).

Derwent Abstract: AN 1999-350322 [30] (JP11127861).

Derwent Abstract: AN 2000-018687 [02] (JP11292840).

Derwent Abstract: AN 1999-186214 [16] (JP11035478).

Derwent Abstract: AN 1999-374374 [32] (JP11137252).

Cappelletti et al.; New Conformationally Constrained Xxx-Pro bicyclic mimetics; Letters in Peptide Science; 1995; vol. 2; pp. 161-164.

Glen et al.; Electron-Impact-Induced Fragmentation of Some Isomeric Cyclopropyl Picolyl and Pyridyl Ketones; Organic Mass Spectrometry; 1975; vol. 10; pp. 913-918.

Kingsbury et al.; A Recyclable Ru-Based Metathesis Catalyst; Journal of the American Chemical Society; 1999; vol. 121; pp. 791-799.

Wieland et al.; Amanita Toxins. XVII. Attempted syntheses of phalloine-like cyclopeptides; Ann. 1959, 626: 154-173.

Jackson et al.; Potent alpha 4 beta 1 Peptide Antagonists as Potential Anti-Inflammatory Agents; J. Med. Chem. 1997; vol. 40; pp. 3359-3368.

Steinkuhler et al.; Product Inhibition of the Hepatitis C Virus NS3 Protease; Biochemistry; vol. 37; 1998; pp. 8899-8905.

Ingallinella et al.; Potent Peptide Inhibitors of Human Hepatitis C Virus NS3 Protease Are Obtained by Optimizing the Cleavage Products; Biochemistry; 1998; vol. 37; pp. 8906-8914.

Chu et al.; Structure of Sch 68631: A New Hepatitis C Virus Proteinase Inhibitor from Streptomyces sp.; Tetrahedron Letters;1996; vol. 37; No. 40; pp. 7229-7232.

Matsumoto et al.; 3D Modeling of HCV Protease and Computer Screening of its Inhibitors; Antiviral Research, 1996, A 23, 30, 1, Abstract 19.

Llinas-Brunet et al.; Peptide-Based Inhibitors of the Hepatitis C Virus Serine Protease; Bioorganic & Medicinal Chemistry Letters; No. 8; 1998; pp. 1713-1718.

Llinas-Brunet et al.; Studies on the C-Terminal of Hexapeptide Inhibitors of the Hepatitis C Virus Serine Protease; Bioorganic & Medicinal Chemistry Letters; No. 8; 1998; pp. 2719-2724.

Huang et al.; Olefin Metathesis-Active Ruthenium Complexes Bearing a Nucleophilic Carbene Ligand; Journal of the American Chemical Society; 1999; vol. 121; pp. 2674-2678.

Website: http://www.hcvadvocate.org/pdf/aasld_2002_sp-3.pdf; What Have We Learned about Hepatitis C at the 2002 Aasld Conference?; 3rd Part; Alan Franciscus, Editor in Chief at HCV Advocate; Translation by Clara Maltras.

Website: http://www.medknowledge.de/neu/2002/IV-2002-32-biln-2061-pipeline.htrn; Neue Medikamente im Pipeline 2002.

Website: http://www.natap.org/2002/AASLD/day14.htm; Sulkowski; Orally available Hepatitis C Virus (HCV) Proteasse Inhibitor (BILN 2061, Boehringer Ingelheim Pharma) Demonstrates Potent Anti-viral Activity in Persons Infected with HCV Genotype 1; Conference Reports for NATAP; American Association for the Study of Liver Diseases; Nov. 2-5, 2002; Boston, MA.

* cited by examiner

MACROCYCLIC PEPTIDES ACTIVE AGAINST THE HEPATITIS C VIRUS

This application claims benefit from U.S. Provisional Application No. 60/504,839, filed Sep. 22, 2003, which application is herein incorporated by reference in its entirety.

FIELD OF THE INVENTION

The present invention relates to compounds, processes for their synthesis, compositions and methods for the treatment of hepatitis C virus (HCV) infection. In particular, the present invention provides novel peptide analogs, pharmaceutical compositions containing such analogs and methods for using these analogs in the treatment of HCV infection.

BACKGROUND OF THE INVENTION

Hepatitis C virus (HCV) is the major etiological agent of post-transfusion and community-acquired non-A non-B hepatitis worldwide. It is estimated that over 200 million people worldwide are infected by the virus. A high percentage of carriers become chronically infected and many progress to chronic liver disease, so-called chronic hepatitis C. This group is in turn at high risk for serious liver disease such as liver cirrhosis, hepatocellular carcinoma and terminal liver disease leading to death.

The mechanism by which HCV establishes viral persistence and causes a high rate of chronic liver disease has not been thoroughly elucidated. It is not known how HCV interacts with and evades the host immune system. In addition, the roles of cellular and humoral immune responses in protection against HCV infection and disease have yet to be established. Immunoglobulins have been reported for prophylaxis of transfusion-associated viral hepatitis, however, the Center for Disease Control does not presently recommend immunoglobulin treatment for this purpose. The lack of an effective protective immune response is hampering the development of a vaccine or adequate post-exposure prophylaxis measures, so in the near-term, hopes are firmly pinned on antiviral interventions.

Various clinical studies have been conducted with the goal of identifying pharmaceutical agents capable of effectively treating HCV infection in patients afflicted with chronic hepatitis C. These studies have involved the use of interferon-alpha, alone and in combination with other antiviral agents. Such studies have shown that a substantial number of the participants do not respond to these therapies, and of those that do respond favorably, a large proportion were found to relapse after termination of treatment.

Until recently, interferon (IFN) was the only available therapy of proven benefit approved in the clinic for patients with chronic hepatitis C. However the sustained response rate is low, and interferon treatment also induces severe side-effects (i.e. retinopathy, thyroiditis, acute pancreatitis, depression) that diminish the quality of life of treated patients. Recently, interferon in combination with ribavirin has been approved for patients non-responsive to IFN alone. However, the side effects caused by IFN are not alleviated with this combination therapy. Pegylated forms of interferons such as PEG-Intron® and Pegasys® can apparently partially address these deleterious side-effects but antiviral drugs still remain the avenue of choice for oral treatment of HCV.

Therefore, a need exists for the development of effective antiviral agents for treatment of HCV infection that overcome the limitations of existing pharmaceutical therapies.

HCV is an enveloped positive strand RNA virus in the Flaviviridae family. The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature nonstructural proteins (NS2, NS3, NS4A, NS4B, NS5A, and NS5B) is effected by two viral proteases. The first one, as yet poorly characterized, cleaves at the NS2-NS3 junction (henceforth referred to as NS2/3 protease); the second one is a serine protease contained within the N-terminal region of NS3 (NS3 protease) and mediates all the subsequent cleavages downstream of NS3, both in cis, at the NS3-NS4A cleavage site, and in trans, for the remaining NS4A-NS4B, NS4B-NS5A and NS5A-NS5B sites. The NS4A protein appears to serve multiple functions, acting as a cofactor for the NS3 protease and possibly assisting in the membrane localization of NS3 and other viral replicase components. The complex formation of the NS3 protease with NS4A seems necessary to the processing events, enhancing the proteolytic efficiency at all of the sites. The NS3 protein also exhibits nucleoside triphosphatase and RNA helicase activities. NS5B is a RNA-dependent RNA polymerase that is involved in the replication of HCV.

A general strategy for the development of antiviral agents is to inactivate virally encoded enzymes that are essential for the replication of the virus. In a two day clinical trial, it has been shown that the HCV NS3 protease inhibitor BILN 2061 is effective in rapidly reducing viral loads in patients infected with the hepatitis C virus (*Nature* (2003) 426, p.186-189), thus providing proof of principle of the clinical antiviral activity of HCV NS3 protease inhibitors.

The NS3 protease has been found to potentially have an additional impact by blocking the IFN-mediated cellular antiviral activity in the infected cell (Foy et al., *Science*, 17 Apr. 2003). This lends credence to a hypothesis that the NS3/NS4A protease may represent a dual therapeutic target, the inhibition of which may both block viral replication and restore Interferon response of HCV infected cells.

In WO 00/59929 compounds of the formula:

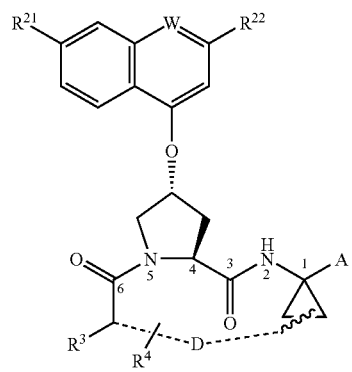

wherein W is CH or N and the substituents and groups A, D, $R^{21}$, $R^{22}$, $R^3$ and $R^4$ are as defined therein, are described as HCV viral NS3 inhibitors, an enzyme essential for the replication of the hepatitis C virus.

In WO 03/053349 compounds of the formula:

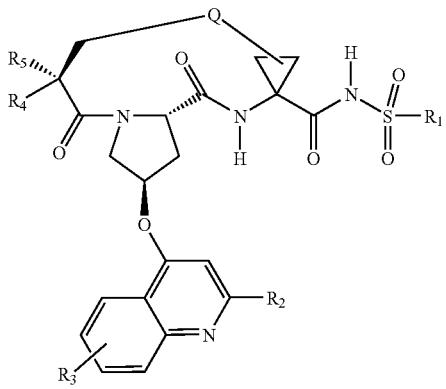

wherein $R^1$, $R^2$, $R^3$, $R^4$, $R^5$ and Q are as defined therein, are also described as HCV viral NS3 protease inhibitors.

Furthermore, WO 03/064455 also describes compounds of the formula:

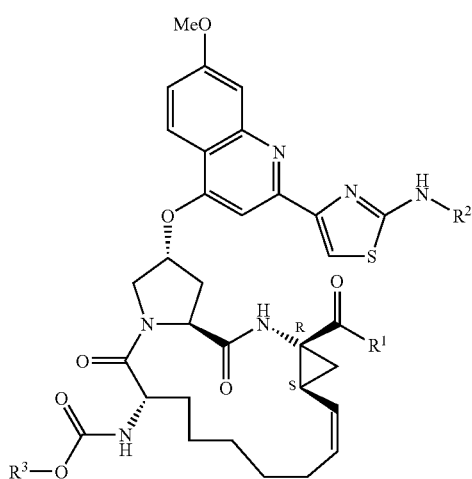

wherein $R^1$, $R^2$ and $R^3$ are defined therein, as HCV protease inhibitors.

The present invention now provides novel compounds that are inhibitory to the NS3 protease. Furthermore, compounds being active in cell culture are provided.

An advantage of one aspect of the present invention resides in the fact that compounds according to this invention specifically inhibit the NS3 protease and do not show significant inhibitory activity against other serine proteases such as human leukocyte elastase (HLE), porcine pancreatic elastase (PPE), or bovine pancreatic chymotrypsin, or cysteine proteases such as human liver cathepsin B (Cat B).

SUMMARY OF THE INVENTION

Included in the scope of the invention are compounds of formula I:

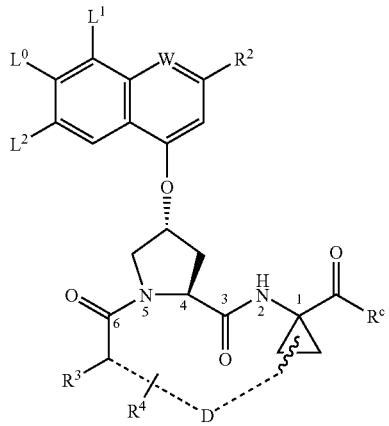

wherein W is CH or N, $L^0$ is H, —OH, —O—$(C_{1-4})$alkyl, —$NH_2$, —NH$(C_{1-4})$alkyl or —N$((C_{1-4})$alkyl$)_2$;

$L^1$, $L^2$ are each independently halogen, $(C_{1-4})$alkyl, $(C_{2-4})$alkynyl, —O—$(C_{1-4})$alkyl, —S—$(C_{1-4})$alkyl, —SO—$(C_{1-4})$alkyl, or —$SO_2$-$(C_{1-4})$alkyl; and
either $L^1$ or $L^2$ (but not both at the same time) may also be H; or
$L^0$ and $L^1$ or
$L^0$ and $L^2$ may be covalently bonded to form, together with the two C-atoms to which they are linked, a 4-, 5- or 6-membered carbocyclic ring wherein one —$CH_2$-group and, in the case of 5- or 6-membered ring, one or two —$CH_2$-groups not being directly linked to each other, may be replaced each independently by —O— or $NR^a$ to form a heterocyclic ring wherein $R^a$ is H or $(C_{1-4})$alkyl, and wherein said carbo- or heterocyclic ring is optionally mono- or di-substituted with $(C_{1-4})$alkyl;

$R^2$ is $(C_{6\ or\ 10})$aryl or Het, wherein Het is a five-, six-, or seven-membered, saturated or unsaturated (including aromatic) heterocycle, containing from one to four heteroatoms each independently selected from nitrogen, oxygen and sulfur, said aryl or Het being substituted with $R^{24}$,
wherein $R^{24}$ is H, halo, $(C_{1-6})$alkoxy, $(C_{3-6})$cycloalkoxy or $NO_2$; or
$R^{24}$ is $R^{20}$, —NHCOR$^{20}$, —NHCOOR$^{20}$, —NHR$^{21}$ or —NHCONR$^{21}$R$^{22}$, wherein
$R^{20}$ is selected from $(C_{1-8})$alkyl, $(C_{3-7})$cycloalkyl and $(C_{1-4})$alkyl-$(C_{3-7})$cycloalkyl, wherein said cycloalkyl and alkyl-cycloalkyl may be mono-, di- or tri-substituted with $(C_{1-3})$alkyl;
$R^{21}$ is H or $R^{20}$ as defined above; and
$R^{22}$ is H or methyl;

$R^3$ is hydroxy, $NH_2$, or a group of formula —NH—$R^{31}$, wherein $R^{31}$ is $(C_{6-10})$aryl, heteroaryl, —C(O)—B, —C(O)—OB, or —C(O)—NH—B, wherein B is $(C_{1-10})$ alkyl, $(C_{3-7})$ cycloalkyl or $(C_{1-4})$alkyl-$(C_{3-7})$cycloalkyl,
a) wherein each said alkyl, cycloalkyl, and alkyl-cycloalkyl may be mono-, di- or tri-substituted with $(C_{1-3})$alkyl; and
b) wherein each said alkyl, cycloalkyl, and alkyl-cycloalkyl may be mono- or di-substituted with substituents each independently selected from hydroxy and O—$(C_{1-6})$alkyl; and
c) wherein each of said alkyl groups may be mono-, di- or tri-substituted with halogen; and d) wherein in each of said cycloalkyl groups being 5-, 6- or 7-membered, one or two —$CH_2$-groups not being directly linked to each other may be replaced by —O—;

D is a 5 to 10-atom saturated or unsaturated alkylene chain optionally containing one to three heteroatoms each independently selected from: O, S, and N—$R^{41}$, wherein $R^{41}$ is H, $(C_{1-6})$alkyl, $(C_{3-6})$cycloalkyl, or —C(O)—$R^{42}$, wherein $R^{42}$ is $(C_{1-6})$alkyl, $(C_{3-6})$cycloalkyl or $(C_{6\,or\,10})$aryl;

$R^4$ is H or from one to three substituents at any carbon atom of said chain D, said substituents each independently selected from the group consisting of: $(C_{1-6})$alkyl, $(C_{1-6})$haloalkyl, $(C_{1-6})$alkoxy, hydroxy, halo, amino, oxo, thio, and $(C_{1-6})$alkylthio;

and $R^C$ is hydroxy or —$NHSO_2R^S$ wherein $R^S$ is $(C_{1-6})$alkyl, $(C_{2-6})$alkenyl, $(C_{3-7})$cycloalkyl, $(C_{1-6})$alkyl-$(C_{3-7})$cycloalkyl, phenyl, naphthyl, pyridinyl, $(C_{1-4})$alkyl-phenyl, $(C_{1-4})$alkyl-naphthyl or $(C_{1-4})$alkyl-pyridinyl; each of which optionally being monosubstituted with nitro; and each of which optionally being mono-, di- or tri-substituted with substituents each independently selected from halogen, hydroxy, cyano, $(C_{1-6})$alkyl, $(C_{2-6})$alkenyl, O—$(C_{1-6})$alkyl, —CO—$NH_2$, —CO—NH$(C_{1-4})$alkyl, —CO—N$((C_{1-4})$alkyl$)_2$, —$NH_2$, —NH$(C_{1-4})$alkyl and —N$((C_{1-4})$alkyl$)_2$, wherein $(C_{1-6})$alkyl and O—$(C_{1-6})$alkyl are optionally substituted with one to three halogen atoms;

or $R^S$ is —N$(R^{N2})(R^{N1})$, wherein $R^{N1}$ and $R^{N2}$ are each independently selected from H, $(C_{1-6})$alkyl, $(C_{3-7})$cycloalkyl, $(C_{1-6})$alkyl-$(C_{3-7})$cycloalkyl, aryl and $(C_{1-6})$alkyl-aryl; wherein said $(C_{1-6})$alkyl, $(C_{3-7})$cycloalkyl, $(C_{1-6})$alkyl-$(C_{3-7})$cycloalkyl, aryl and $(C_{1-6})$alkyl-aryl are optionally substituted with one or more substituents each independently selected from halogen, $(C_{1-6})$alkyl, hydroxy, cyano, O—$(C_{1-6})$alkyl, —$NH_2$, —NH$(C_{1-4})$alkyl, —N$((C_{1-4})$alkyl$)_2$, —CO—$NH_2$, —CO—NH$(C_{1-4})$alkyl, —CO—N$((C_{1-4})$alkyl$)_2$, —COOH, and —COO$(C_{1-6})$alkyl; or $R^{N2}$ and $R^{N1}$ are linked, together with the nitrogen to which they are bonded, to form a 3- to 7-membered monocyclic saturated or unsaturated heterocycle or a 9- or 10-membered bicyclic saturated or unsaturated heterocycle, each of which optionally containing from one to three further heteroatoms each independently selected from N, S and O, and each of which being optionally substituted with one or more substituents each independently selected from halogen, $(C_{1-6})$alkyl, hydroxy, cyano, O—$(C_{1-6})$alkyl, —$NH_2$, —NH$(C_{1-4})$alkyl, —N$((C_{1-4})$alkyl$)_2$, —CO—$NH_2$, —CO—NH$(C_{1-4})$alkyl, —CO—N$((C_{1-4})$alkyl$)_2$, —COOH, and —COO$(C_{1-6})$alkyl;

or a pharmaceutically acceptable salt or ester thereof;

with the proviso that when W is N; and $L^0$ is H; one of $L^1$ or $L^2$ is H and the other $L^2$ or $L^1$ is halo or —O—$(C_{1-4})$alkyl; and $R^2$ is $(C_{6\,or\,10})$aryl or Het, wherein Het is a five-, six-, or seven-membered, saturated or unsaturated (including aromatic) heterocycle, containing from one to four heteroatoms each independently selected from nitrogen, oxygen and sulfur, said aryl or Het being substituted with $R^{24}$, wherein $R^{24}$ is selected from H, halo, $(C_{1-6})$alkyl, —$NH_2$, —NH$(C_{1-6})$alkyl, —NH, —NHCOO$(C_{1-6})$alkyl, —NHCOO$(C_{3-6})$cycloalkyl, —NHCO$(C_{1-6})$alkyl, —NHCO, and —NHCONR$^{21}$R$^{22}$ wherein $R^{21}$ is selected from H, $(C_{1-6})$alkyl and $(C_{3-6})$cycloalkyl and $R^{22}$ is selected from H and methyl; and $R^3$ is $NH_2$, or a group of formula —NH—$R^{31}$, wherein $R^{31}$ is —C(O)—B, —C(O)—OB, or —C(O)—NH—B, wherein B is $(C_{1-6})$alkyl optionally substituted with halo, or B is —$(CH_2)_p$—$(C_{3-7})$cycloalkyl wherein p is 0-4, or B is a tetrahydrofuran ring linked through the C3 or C4 position of the ring; and D is a 5 to 9-atom saturated or unsaturated alkylene chain optionally containing one to three heteroatoms each independently selected from O and S; and $R^4$ is H;

then $R^C$ is not —$NHSO_2R^S$, wherein $R^S$ is $(C_{1-6})$alkyl or unsubstituted $(C_{3-7})$cycloalkyl.

Included within the scope of this invention is a pharmaceutical composition comprising an anti-hepatitis C virally effective amount of a compound of formula 1, or a pharmaceutically acceptable salt or ester thereof, in admixture with at least one pharmaceutically acceptable carrier medium or auxiliary agent.

According to a further aspect of this embodiment the pharmaceutical composition according to this invention further comprises a therapeutically effective amount of at least one other antiviral agent.

Another important aspect of the invention involves a method of treating or preventing a hepatitis C viral infection in a mammal by administering to the mammal an anti-hepatitis C virally effective amount of a compound of formula 1, a pharmaceutically acceptable salt or ester thereof, or a composition as described above, alone or in combination with at least one other antiviral agent, administered together or separately.

Also within the scope of this invention is the use of a compound of formula 1, or a pharmaceutically acceptable salt or ester thereof, as described herein, for the manufacture of a medicament for the treatment or prevention of hepatitis C viral infection in a mammal.

A further aspect of the invention provides the use of a compound of formula 1, or a pharmaceutically acceptable salt or ester thereof, as described herein, in combination with at least one other antiviral agent, for the manufacture of a medicament for the treatment or prevention of hepatitis C viral infection in a mammal.

DETAILED DESCRIPTION OF PREFERRED EMBODIMENTS

Definitions

As used herein, the following definitions apply unless otherwise noted:

With reference to the instances where (R) or (S) is used to designate the absolute configuration of a substituent or asymmetric center of a compound of formula 1, the designation is done in the context of the whole compound and not in the context of the substituent or asymmetric center alone.

The designation "P1, P2, and P3" as used herein refer to the position of the amino acid residues starting from the C-terminus end of the peptide analogs and extending towards the N-terminus (i.e. P1 refers to position 1 from the C-terminus, P2: second position from the C-terminus, etc.) (see Berger A. & Schechter I., Transactions of the Royal Society London series B257, 249-264 (1970)).

As used herein the term "(1R,2S)-vinyl-ACCA" refers to a compound of formula:

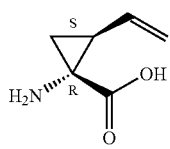

namely, (1R,2S) 1-amino-2-ethenylcyclopropanecarboxylic acid.

The term "$(C_{1-n})$alkyl" as used herein, either alone or in combination with another substituent, means acyclic, straight or branched chain alkyl substituents containing from 1 to n carbon atoms. "$(C_{1-6})$alkyl" includes, but is not limited to, methyl, ethyl, n-propyl, n-butyl, 1-methylethyl (i-propyl), 1-methylpropyl, 2-methylpropyl, 1,1-dimethylethyl (tert-butyl), pentyl and hexyl. The abbreviation Me denotes a methyl group.

The term "$(C_{2-n})$alkenyl", as used herein, wherein n is an integer, either alone or in combination with another radical, is intended to mean an unsaturated, acyclic straight or branched chain radical containing two to n carbon atoms, at least two of which are bonded to each other by a double bond. Examples of such radicals include, but are not limited to, ethenyl (vinyl), 1-propenyl, 2-propenyl, and 1-butenyl.

The term "$(C_{2-n})$alkynyl", as used herein, wherein n is an integer, either alone or in combination with another radical, is intended to mean an unsaturated, acyclic straight or branched chain radical containing two to n carbon atoms, at least two of which are bonded to each other by a triple bond. Examples of such radicals include, but are not limited to, ethynyl, 1-propynyl, 2-propynyl, and 1-butynyl.

As used herein, the term "alkylene," either alone or in combination with another 0.9-radical, means a divalent alkyl radical derived by removal of two hydrogen atoms from an aliphatic hydrocarbon containing one to ten carbon atoms which may optionally be unsaturated, so as to contain one or more double or triple bonds, or may additionally optionally contain one or more heteroatoms each independently selected from N, O and S. Examples of alkylene groups include, but are not limited to, —CH$_2$—, —CH$_2$CH$_2$—, —CH$_2$CH$_2$CH$_2$—, —CH$_2$CH(Me)—, —(CH$_2$)$_5$— CH=CH$_2$—, —(CH$_2$)$_3$—O—(CH$_2$)$_3$—, —(CH$_2$)$_2$—NH—(CH$_2$)$_4$—, and —(CH$_2$)$_3$—O—CH$_2$CH=CH$_2$—.

The term "$(C_{3-6})$cycloalkyl" as used herein, either alone or in combination with another substituent, means a cycloalkyl substituent containing from 3 to m carbon atoms and includes, but is not limited to, cyclopropyl, cyclobutyl, cyclopentyl, cyclohexyl and cycloheptyl.

The term "$(C_{1-n})$alkyl-$(C_{3-m})$cycloalkyl" as used herein means an alkyl radical containing 1 to n carbon atoms to which a cycloalkyl radical containing from 3 to m carbon atoms is directly linked; and includes, but is not limited to, cyclopropylmethyl, cyclopentylethyl, cyclohexylmethyl, 1-cyclohexylethyl, 2-cyclohexylethyl and cycloheptylpropyl.

The term "$(C_{6\ or\ 10})$aryl" as used herein, either alone or in combination with another radical, means either an aromatic monocyclic group containing 6 carbon atoms or an aromatic bicyclic group containing 10 carbon atoms. For example, aryl includes phenyl, 1-naphthyl or 2-naphthyl.

As used herein, the term "$(C_{1-n})$alkyl-aryl" means an alkyl radical containing 1 to n carbon atoms to which an aryl radical is bonded. Examples of $(C_{1-3})$alkyl-aryl include, but are not limited to, benzyl (phenylmethyl), 1-phenylethyl, 2-phenylethyl and phenylpropyl.

The term "O—$(C_{1-n})$alkyl" or "$(C_{1-n})$alkoxy" as used herein interchangeably, either alone or in combination with another radical, means the radical —O—$(C_{1-n})$alkyl wherein alkyl is as defined above containing up to n carbon atoms, and includes, but is not limited to, methoxy, ethoxy, propoxy, 1-methylethoxy, butoxy and 1,1-dimethylethoxy. The latter radical is known commonly as tert-butoxy.

As used herein, the term "—S—$(C_{1-n})$alkyl" or "$(C_{1-n})$alkylthio", used interchangeably, refers to a sulfur atom further bonded to an alkyl radical as defined above containing from 1 to n carbon atoms. Examples of $(C_{1-6})$alkylthio include, but are not limited to, methylthio (CH$_3$S—), ethylthio (CH$_3$CH$_2$S—), n-propylthio (CH$_3$CH$_2$CH$_2$S—), isopropylthio ((CH$_3$)$_2$CHS—), tert-butylthio ((CH$_3$)$_3$CS—), etc.

The term "$(C_{1-n})$haloalkyl" as used herein, means an alkyl radical as defined above wherein one or more hydrogen atoms have been replaced by halogen atoms. Examples of $(C_{1-6})$ haloalkyl include, but are not limited to, chloromethyl, bromomethyl, 2-chloroethyl and trifluoromethyl.

The term "halo" or "halogen" as used herein means a halogen substituent selected from fluoro, chloro, bromo and iodo.

The term "Het" as used herein, either alone or in combination with another substituent, means a monovalent substituent derived by removal of a hydrogen from a five-, six-, or seven-membered saturated or unsaturated (including aromatic) heterocycle containing from one to four heteroatoms each independently selected from nitrogen, oxygen and sulfur. Examples of suitable heterocycles include but are not limited to: tetrahydrofuran, thiophene, diazepine, isoxazole, thiazole, piperidine, dioxane, morpholine, pyrimidine and

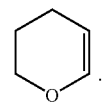

The term "Het" also includes a heterocycle as defined above fused to one or more other cycle, be it a heterocycle or any other cycle. One such example includes thiazolo[4,5-b]-pyridine.

Although generally covered under the term "Het", the term "heteroaryl" as used herein precisely defines an unsaturated heterocycle for which the double bonds form an aromatic system. Suitable examples of heteroaryl include but are not limited to: quinoline, indole, pyridine,

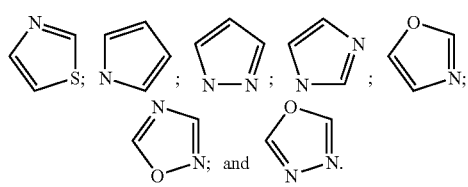

The term "pharmaceutically acceptable ester" as used herein, either alone or in combination with another substituent, means esters of the compound of formula I in which any of the carboxyl functions of the molecule, but preferably the carboxy terminus, is replaced by an alkoxycarbonyl function:

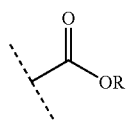

in which the R moiety of the ester is selected from alkyl (e.g. methyl, ethyl, n-propyl, t-butyl, n-butyl); alkoxyalkyl (e.g. methoxymethyl); alkoxyacyl (e.g. acetoxymethyl); aralkyl (e.g. benzyl); aryloxyalkyl (e.g. phenoxymethyl); aryl (e.g. phenyl), optionally substituted with halogen, $C_{1-4}$ alkyl or $C_{1-4}$ alkoxy. Other suitable prodrug esters can be found in Design of prodrugs, Bundgaard, H. Ed. Elsevier (1985). Such pharmaceutically acceptable esters are usually hydrolyzed in vivo when injected in a mammal and transformed into the acid form of the compound of formula 1. With regard to the esters described above, unless otherwise specified, any alkyl moiety present advantageously contains 1 to 16 carbon atoms, particularly 1 to 6 carbon atoms. Any aryl moiety present in such esters advantageously comprises a phenyl group. In particular the esters may be a ($C_{1-6}$)alkyl ester, an unsubstituted benzyl ester or a benzyl ester substituted with at least one halogen, ($C_{1-6}$)alkyl, ($C_{1-6}$)alkoxy, nitro or trifluoromethyl.

The term "pharmaceutically acceptable salt" means a salt of a compound of formula I which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. The term includes pharmaceutically-acceptable acid addition salts and pharmaceutically-acceptable base addition salts. Lists of suitable salts are found in, e.g., S. M. Birge et al., J. Pharm. Sci., 1977, 66, pp. 1-19.

The term "pharmaceutically-acceptable acid addition salt" means those salts which retain the biological effectiveness and properties of the free bases and which are not biologically or otherwise undesirable, formed with inorganic acids including but not limited to hydrochloric acid, hydrobromic acid, sulfuric acid, sulfamic acid, nitric acid, phosphoric acid, and the like, and organic acids including, but not limited to, acetic acid, trifluoroacetic acid, adipic acid, ascorbic acid, aspartic acid, benzenesulfonic acid, benzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, hexanoic acid, formic acid, fumaric acid, 2-hydroxyethanesulfonic acid (isethionic acid), lactic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, pivalic acid, propionic acid, pyruvic acid, salicylic acid, stearic acid, succinic acid, sulfanilic acid, tartaric acid, p-toluenesulfonic acid, undecanoic acid, and the like.

The term "pharmaceutically-acceptable base addition salt" means those salts which retain the biological effectiveness and properties of the free acids and which are not biologically or otherwise undesirable, formed with inorganic bases including, but not limited to, ammonia or hydroxide, carbonate, or bicarbonate of ammonium or a metal cation including, but not limited to, sodium, potassium, lithium, calcium, magnesium, iron, zinc, copper, manganese, aluminum, and the like. Particularly preferred are the ammonium, potassium, sodium, calcium, and magnesium salts. Salts derived from pharmaceutically-acceptable organic nontoxic bases include but are not limited to salts of primary, secondary, and tertiary amines, quaternary amine compounds, substituted amines including naturally occurring substituted amines, cyclic amines and basic ion-exchange resins, including, but not limited to, methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, methylglucamine, theobromine, purines, piperazine, piperidine, N-ethylpiperidine, tetramethylammonium compounds, tetraethylammonium compounds, pyridine, N,N-dimethylaniline, N-methylpiperidine, N-methylmorpholine, dicyclohexylamine, dibenzylamine, N,N-dibenzylphenethylamine, 1-ephenamine, N,N'-dibenzylethylenediamine, polyamine resins, and the like. Particularly preferred organic nontoxic bases are isopropylamine, diethylamine, ethanolamine, trimethylamine, dicyclohexylamine, choline, and caffeine.

The term "mammal" as it is used herein is meant to encompass humans, as well as non-human mammals which are susceptible to infection by hepatitis C virus including domestic animals, such as cows, pigs, horses, dogs and cats, and non-domestic animals.

The term "antiviral agent" as used herein means an agent (compound or biological) that is effective to inhibit the formation and/or replication of a virus in a mammal. This includes agents that interfere with either host or viral mechanisms necessary for the formation and/or replication of a virus in a mammal. Such agents can be selected from: another anti-HCV agent, HIV inhibitor, HAV inhibitor and HBV inhibitor.

Antiviral agents include, for example, ribavirin, amantadine, VX-497 (merimepodib, Vertex Pharmaceuticals), VX-498 (Vertex Pharmaceuticals), Levovirin, Viramidine, Ceplene (maxamine), XTL-001 and XTL-002 (XTL Biopharmaceuticals).

The term "other anti-HCV agent" as used herein means those agents that are effective for diminishing or preventing the progression of hepatitis C related symptoms of disease. Such agents can be selected from: immunomodulatory agents, inhibitors of HCV NS3 protease, inhibitors of HCV polymerase or inhibitors of another target in the HCV life cycle.

The term "immunomodulatory agent" as used herein means those agents (compounds or biologicals) that are effective to enhance or potentiate the immune system response in a mammal. Immunomodulatory agents include, for example, class I interferons (such as α-, β-, δ-, ω- and τ-interferons, consensus interferons and asialo-interferons), class II interferons (such as γ-interferons) and pegylated interferons.

The term "inhibitor of HCV NS3 protease" as used herein means an agent (compound or biological) that is effective to inhibit the function of HCV NS3 protease in a mammal. Inhibitors of HCV NS3 protease include, for example, those compounds described in WO 99/07733, WO 99/07734, WO 00/09558, WO 00/09543, WO 00/59929, WO 03/064416, WO 03/064455, WO 03/064456, WO 02/060926, WO 03/053349, WO 03/099316, WO 03/099274, WO 2004/032827 and US 2004/0077551 and the Vertex pre-development candidate identified as VX-950.

The term "inhibitor of HCV polymerase" as used herein means an agent (compound or biological) that is effective to inhibit the function of an HCV polymerase in a mammal. This includes, for example, inhibitors of HCV NS5B polymerase.

Inhibitors of HCV polymerase include non-nucleosides, for example, those compounds described in:

U.S. application Ser. No. 10/755,256 filed Jan. 12, 2004, herein incorporated by reference in its entirety (Boehringer Ingelheim), U.S. application Ser. No. 10/755,544 filed Jan. 12, 2004, herein incorporated by reference in its entirety (Boehringer Ingelheim), WO 04/005286 (Gilead), WO 04/002977 (Pharmacia), WO 04/002944 (Pharmacia), WO 04/002940 (Pharmacia), WO 03/101993 (Neogenesis), WO 03/099824 (Wyeth), WO 03/099275 (Wyeth), WO 03/099801 (GSK)), WO 03/097646 (GSK), WO 03/095441 (Pfizer), WO 03/090674 (Viropharma), WO 03/084953 (B&C Biopharm), WO 03/082265 (Fujisawa), WO 03/082848 (Pfizer), WO 03/062211 (Merck), WO 03/059356 (GSK), EP 1321463 (Shire), WO 03/040112 (Rigel), WO 03/037893 (GSK), WO 03/037894 (GSK), WO 03/037262 (GSK), WO 03/037895 (GSK), WO 03/026587 (BMS), WO 03/002518 (Dong Wha), WO 03/000254 (Japan Tobacco), WO 02/100846 A1 (Shire), WO 02/100851 A2 (Shire), WO 02/098424 A1 (GSK), WO 02/079187 (Dong Wha), WO Mar. 2, 20497 (Shionogi), WO 02/06246 (Merck), WO 01/47883 (Japan Tobacco), WO 01/85172 A1 (GSK), WO 01/85720 (GSK), WO 01/77091 (Tularik), WO 00/18231 (Viropharma), WO 00/13708 (Viropharma), WO 01/10573 (Viropharma) WO 00/06529 (Merck), EP 1 256 628 A2 (Agouron), WO 02/04425 (Boehringer Ingelheim) WO 03/007945 (Boehringer Ingelheim), WO 03/010140 (Boehringer Ingelheim) and WO 03/010141 (Boehringer Ingelheim). Furthermore other inhibitors of HCV polymerase also include nucleoside analogs, for example, those compounds described in: WO 04/007512 (Merck/Isis), WO 04/003000 (Idenix), WO 04/002999 (Idenix), WO 04/0002422 (Idenix), WO 04/003138 (Merck), WO 03/105770 (Merck), WO 03/105770 (Merck), WO 03/093290 (Genelabs), WO 03/087298 (Biocryst), WO 03/062256 (Ribapharm), WO 03/062255 (Ribapharm), WO 03/061385 (Ribapharm), WO 03/026675 (Idenix), WO 03/026589 (Idenix), WO 03/020222 (Merck), WO 03/000713 (Glaxo), WO 02/100415 (Hoffmann-La Roche), WO 02/1094289 (Hoffmann-La Roche), WO 02/051425 (Mitsubishi), WO 02/18404 (Hoffmann-La Roche), WO 02/069903 (Biocryst Pharmaceuticals Inc.), WO 02/057287 (Merck/Isis), WO 02/057425 (Merck/Isis), WO 01/90121 (Idenix), WO 01/60315 (Shire) and WO 01/32153 (Shire).

Specific examples of inhibitors of an HCV polymerase, include JTK-002, JTK-003 and JTK-109 (Japan Tobacco).

The term "inhibitor of another target in the HCV life cycle" as used herein means an agent (compound or biological) that is effective to inhibit the formation and/or replication of HCV in a mammal other than by inhibiting the function of the HCV NS3 protease. This includes agents that interfere with either host or HCV viral mechanisms necessary for the formation and/or replication of HCV in a mammal.

Inhibitors of another target in the HCV life cycle include, for example, agents that inhibit a target selected from a helicase, a NS2/3 protease and an internal ribosome entry site (IRES). Specific examples of inhibitors of another target in the HCV life cycle include ISIS-14803 (ISIS Pharmaceuticals).

The term "HIV inhibitor" as used herein means an agent (compound or biological) that is effective to inhibit the formation and/or replication of HIV in a mammal. This includes agents that interfere with either host or viral mechanisms necessary for the formation and/or replication of HIV in a mammal. HIV inhibitors include, for example, nucleoside inhibitors, non-nucleoside inhibitors, protease inhibitors, fusion inhibitors and integrase inhibitors.

The term "HAV inhibitor" as used herein means an agent (compound or biological) that is effective to inhibit the formation and/or replication of HAV in a mammal. This includes agents that interfere with either host or viral mechanisms necessary for the formation and/or replication of HAV in a mammal. HAV inhibitors include Hepatitis A vaccines, for example, Havrix® (GlaxoSmithKline), VAQTA® (Merck) and Avaxim® (Aventis Pasteur).

The term "HBV inhibitor" as used herein means an agent (compound or biological) that is effective to inhibit the formation and/or replication of HBV in a mammal. This includes agents that interfere with either host or viral mechanisms necessary for the formation and/or replication of HBV in a mammal. HBV inhibitors include, for example, agents that inhibit HBV viral DNA polymerase or HBV vaccines. Specific examples of HBV inhibitors include Lamivudine (Epivir-HBV®), Adefovir Dipivoxil, Entecavir, FTC (Coviracil®), DAPD (DXG), L-FMAU (Clevudine®), AM365 (Amrad), Ldt (Telbivudine), monoval-LdC (Valtorcitabine), ACH-126,443 (L-Fd4C) (Achillion), MCC478 (Eli Lilly), Racivir (RCV), Fluoro-L and D nucleosides, Robustaflavone, ICN 2001-3 (ICN), Bam 205 (Novelos), XTL-001 (XTL), Imino-Sugars (Nonyl-DNJ) (Synergy), HepBzyme; and immunomodulator products such as: interferon alpha 2b, HE2000 (Hollis-Eden), Theradigm (Epimmune), EHT899 (Enzo Biochem), Thymosin alpha-1 (Zadaxin®), HBV DNA vaccine (PowderJect), HBV DNA vaccine (Jefferon Center), HBV antigen (OraGen), BayHep B® (Bayer), Nabi-HB® (Nabi) and Anti-hepatitis B (Cangene); and HBV vaccine products such as the following: Engerix B, Recombivax HB, GenHevac B, Hepacare, Bio-Hep B, TwinRix, Comvax, Hexavac.

The term "class I interferon" as used herein means an interferon selected from a group of interferons that all bind to receptor type 1. This includes both naturally and synthetically produced class I interferons. Examples of class I interferons include α-, β-, δ-, ω- and τ-interferons, consensus interferons, asialo-interferons and pegylated forms thereof.

The term "class II interferon" as used herein means an interferon selected from a group of interferons that all bind to receptor type II. Examples of class II interferons include γ-interferons.

Specific preferred examples of some of these agents are listed below:
  antiviral agents: ribavirin and amantadine;
  immunomodulatory agents: class I interferons, class II interferons or pegylated forms thereof;
  HCV polymerase inhibitors: nucleoside analogs and non-nucleosides;
  inhibitor of another target in the HCV life cycle that inhibits a target selected from: NS3 helicase, NS2/3 protease or internal ribosome entry site (IRES);
  HIV inhibitors: nucleoside inhibitors, non-nucleoside inhibitors, protease inhibitors, fusion inhibitors and integrase inhibitors; or
  HBV inhibitors: agents that inhibit viral DNA polymerase or is an HBV vaccine.

As discussed above, combination therapy is contemplated wherein a compound of formula 1, or a pharmaceutically acceptable salt thereof, is co-administered with at least one additional agent selected from: an antiviral agent, an immunomodulatory agent, an inhibitor of HCV polymerase, another inhibitor of HCV NS3 protease, an inhibitor of another target in the HCV life cycle, an HIV inhibitor, an HAV inhibitor and an HBV inhibitor. Examples of such agents are provided in the Definitions section above. These additional agents may be combined with the compounds of this invention to create a single pharmaceutical dosage form. Alternatively these additional agents may be separately administered to the patient as part of a multiple dosage form, for example, using a kit. Such additional agents may be administered to the patient prior to, concurrently with, or following the administration of a compound of formula 1, or a pharmaceutically acceptable salt thereof.

As used herein, the term "treatment" means the administration of a compound or composition according to the present invention to alleviate or eliminate symptoms of the hepatitis C disease and/or to reduce viral load in a patient.

As used herein, the term "prevention" means the administration of a compound or composition according to the present invention post-exposure of the individual to the virus but before the appearance of symptoms of the disease, and/or prior to the detection of the virus in the blood.

As used herein, the designation whereby a bond to a substituent R is drawn as emanating from the center of a ring, such as, for example,

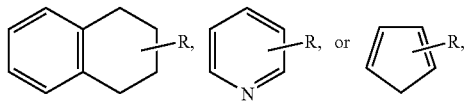

means that the substituent R may be attached to any free position on the ring that would otherwise be substituted with a hydrogen atom, unless specified otherwise.

The following sign - - - or → are used interchangeably in sub-formulas to indicate the bond which is connected to the rest of the molecule as defined.

Preferred Embodiments

In the following preferred embodiments, groups and substituents of the compounds according to this invention are described in detail.

According to one embodiment, compounds of formula I are provided:

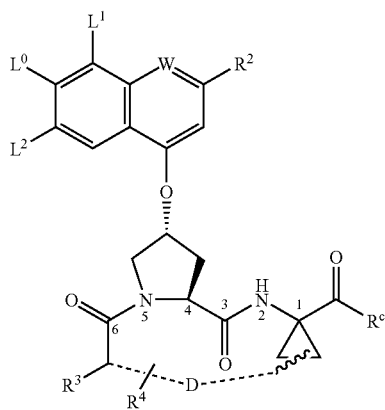

wherein W is CH or N, $L^0$ is H, —OH, —O—$(C_{1-4})$alkyl, —NH$_2$, —NH($C_{1-4}$-alkyl) or —N($C_{1-4}$-alkyl)$_2$;

$L^1$, $L^2$ are each independently halogen, $(C_{1-4})$alkyl, —O—$(C_{1-4})$alkyl, or —S—$(C_{1-4})$alkyl (in any oxidized state); and either $L^1$ or $L^2$ (but not both at the same time) may also be H; or $L^0$ and $L^1$ or $L^0$ and $L^2$ may be covalently bonded to form, together with the two C-atoms to which they are linked, a 4-, 5- or 6-membered carbocyclic ring wherein one —CH$_2$-group and, in the case of 5- or 6-membered ring, one or two —CH$_2$-groups not being directly linked to each other, may be replaced each independently by —O— or NR$^a$ to form a heterocyclic ring wherein R$^a$ is H or $(C_{1-4})$alkyl, and wherein said carbo- or heterocyclic ring is optionally mono- or di-substituted with $(C_{1-4})$alkyl;

$R^2$ is $(C_{6 \text{ or } 10})$aryl or Het, wherein Het is a five-, six-, or seven-membered, saturated or unsaturated heterocycle, containing from one to four heteroatoms each independently selected from nitrogen, oxygen and sulfur, said aryl or Het being substituted with $R^{24}$, wherein $R^{24}$ is H, halo, $(C_{1-6})$alkoxy, $(C_{3-6})$cycloalkoxy or NO$_2$; or $R^{24}$ is $R^{20}$, —NHCOR$^{20}$, —NHCOOR$^{20}$, —NHR$^{21}$ or —NHCONR$^{21}$R$^{22}$, wherein $R^{20}$ is selected from $(C_{1-6})$alkyl, $(C_{3-7})$cycloalkyl and $(C_{1-4})$alkyl-$(C_{3-7})$cycloalkyl, wherein said cycloalkyl and alkyl-cycloalkyl may be mono-, di- or tri-substituted with $(C_{1-3})$alkyl;

$R^{21}$ is H or has one of the meanings of $R^{20}$ as defined above; and $R^{22}$ is H or methyl;

$R^3$ is hydroxy, NH$_2$, or a group of formula —NH—R$^3$, wherein R$^{31}$ is $(C_{6 \text{ or } 10})$aryl, heteroaryl, —C(O)—B, —C(O)—OB, or —C(O)—NH—B, wherein B is $(C_{1-10})$alkyl, $(C_{3-7})$cycloalkyl, or $(C_{1-4})$alkyl-$(C_{3-7})$cycloalkyl, a) wherein said cycloalkyl and alkyl-cycloalkyl may be mono-, di- or tri-substituted with $(C_{1-3})$alkyl;

b) wherein said alkyl, cycloalkyl and alkyl-cycloalkyl may be mono- or di-substituted with substituents each independently selected from hydroxy and O—$(C_{1-6})$alkyl;

c) wherein all said alkyl groups may be mono-, di- or tri-substituted with halogen; and d) wherein in said cycloalkyl groups being 5-, 6- or 7-membered, one or two —CH$_2$-groups not being directly linked to each other may be replaced by —O—;

D is a 5 to 10-atom saturated or unsaturated alkylene chain optionally containing one to three heteroatoms each independently selected from: O, S, or N—R$^{41}$, wherein R$^{41}$ is H, $(C_{1-6})$alkyl, $(C_{3-6})$cycloalkyl, or —C(O)—R$^{42}$, wherein R$^{42}$ is $(C_{1-6})$alkyl, or $(C_{6 \text{ or } 10})$aryl;

$R^4$ is H or from one to three substituents at any carbon atom of said chain D, said substituents each independently selected from the group consisting of: $(C_{1-6})$alkyl, $(C_{1-6})$haloalkyl, $(C_{1-6})$alkoxy, hydroxy, halo, amino, oxo, thio, and $(C_{1-6})$alkylthio;

and $R^C$ is hydroxy or —NHSO$_2$R$^S$ wherein R$^S$ is $(C_{1-6})$alkyl, $(C_{3-7})$cycloalkyl, $(C_{1-6})$alkyl-$(C_{3-7})$cycloalkyl, phenyl, naphthyl, pyridinyl, $(C_{1-4})$alkyl-phenyl, $(C_{1-4})$alkyl-naphthyl or $(C_{1-4})$alkyl-pyridinyl, each of which optionally being mono-, di- or tri-substituted with substituents each independently selected from: halogen, hydroxy, cyano, $(C_{1-4})$alkyl, O—$(C_{1-6})$alkyl, —CO—NH$_2$, —CO—NH$(C_{1-4})$alkyl), —CO—N$(C_{1-4}$-alkyl)$_2$, —NH$_2$, —NH$(C_{1-4}$-alkyl) and —N$(C_{1-4}$-alkyl)$_2$, and each of which optionally being monosubstituted with nitro;

or R$^S$ can be further selected from: —NH$(C_{1-6})$alkyl, N$((C_{1-6})$alkyl)$_2$, -Het,

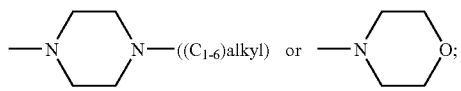

or a pharmaceutically acceptable salt or ester thereof;
with the proviso that
when W is N; and
$L^0$ is H; one of $L^1$ or $L^2$ is H and the other $L^2$ or $L^1$ is halo or —O—$(C_{1-4})$alkyl; and
$R^2$ is $(C_{6\ or\ 10})$aryl or Het, wherein Het is a five-, six-, or seven-membered, saturated or unsaturated (including aromatic) heterocycle, containing from one to four heteroatoms each independently selected from nitrogen, oxygen and sulfur, said aryl or Het being substituted with $R^{24}$,
wherein $R^{24}$ is selected from H, halo, $(C_{1-6})$alkyl, —$NH_2$, —NH$(C_{1-6})$alkyl, —NH, —NHCOO$(C_{1-6})$alkyl, —NHCOO, —NHCO$(C_{1-6})$alkyl, —NHCO, and —NHCONR$^{21}$R$^{22}$ wherein $R^{21}$ is selected from H, $(C_{1-6})$alkyl and (Cm)cycloalkyl and $R^{22}$ is selected from H and methyl; and $R^3$ is $NH_2$, or a group of formula —NH—$R^{31}$, wherein $R^{31}$ is —C(O)—B, —C(O)—OB, or —C(O)—NH—B, wherein B is $(C_{1-6})$alkyl optionally substituted with halo, or B is —$(CH_2)_p$—$(C_{3-7})$cycloalkyl wherein p is 0-4, or B is a tetrahydrofuran ring linked through the C3 or C4 position of the ring; and D is a 5 to 9-atom saturated or unsaturated alkylene chain optionally containing one to three heteroatoms each independently selected from O and S; and $R^4$ is H;

then $R^C$ is not —NHSO$_2$R$^S$, wherein $R^S$ is $(C_{1-6})$alkyl or unsubstituted $(C_{3-7})$cycloalkyl.

Included in the preferred embodiments of the invention are compounds of formula I wherein:

$R^3$:

Preferred embodiments of the present invention include compounds of formula I as described above, wherein the $R^3$ moiety is preferably an amide of formula NH—C(O)—B, a urea of formula NH—C(O)—NH—B, or a carbamate of formula NH—C(O)—O—B, wherein B is as defined herein. More preferably, $R^3$ is a urea or a carbamate.

D:

Preferred embodiments of the present invention include compounds of formula 1, wherein linker D is a 6 to 8 atom saturated or unsaturated alkylene chain. More preferably, linker D is 7 atom chain.

Preferably, the D chain contains one or two heteroatoms each independently selected from: O, S, NH, N—$(C_{1-6})$alkyl and N—C(=O)—$(C_{1-6})$alkyl. More preferably, the D chain optionally contains one heteroatom selected from: NH, and N—C(=O)—$(C_{1-6})$alkyl, most preferably N—C(=O)CH$_3$, and is positioned at atom 10 of the chain. Most preferably, the chain containing a nitrogen atom is saturated.

Alternatively, D contains one heteroatom selected from: O and S. Preferably, when D is 7 atoms in length, the O or S atom is at position 9 of the chain. Preferably, this chain is substituted with $R^4$, wherein $R^4$ is H or $(C_{1-6})$alkyl. More preferably, $R^4$ is H or methyl. Even more preferably, $R^4$ is H or 8-(S)-Me. Most preferably, D is saturated.

Alternatively, D contains one double bond at position 11,12. Preferably, this double bond is trans.

Alternatively, D is an all carbon saturated or unsaturated alkylene chain. In this case, D is preferably saturated and is 7 atom in length. More preferably, D is substituted with $R^4$, wherein $R^4$ is H, oxo, thio, hydroxy, $(C_{1-6})$alkylthio, alkoxy or alkyl. More preferably, $R^4$ is H or $(C_{1-6})$alkyl. Even more preferably, $R^4$ is H or methyl. Most preferably, $R^4$ is H or 10-(S)-Me.

Alternatively, D is an all carbon alkylene chain containing preferably one double bond and is 7 atoms in length. More preferably, this double bond is at position 13,14 of the chain. Most preferably, this double bond is cis. Preferably, this D chain is substituted with $R^4$, wherein $R^4$ is H, oxo, hydroxy, alkoxy or $(C_{1-6})$alkyl. More preferably, $R^4$ is H or $(C_{1-6})$alkyl. Even more preferably, $R^4$ is H or methyl. Most preferably, $R^4$ is H or 10-(S)-Me.

Also included in the preferred embodiments of the invention are compounds of formula I':

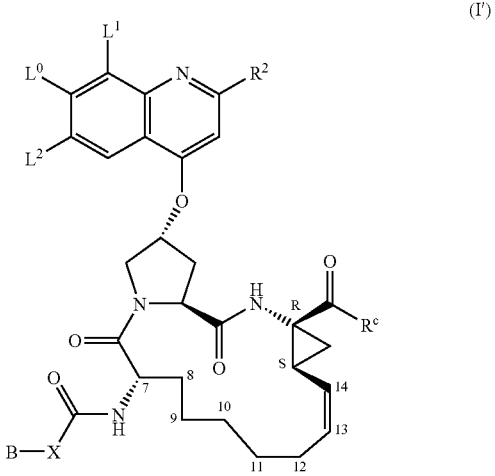

(I')

wherein:
X is O or NH; and B, $L^0$, $L^1$, $L^2$, $R^2$ and $R^C$ are as defined herein;
with the proviso that
when $L^0$ is H; one of $L^1$ or $L^2$ is H and the other $L^2$ or $L^1$ is halo or —O—$(C_{1-4})$alkyl; and
$R^2$ is $(C_{6\ or\ 10})$aryl or Het, wherein Het is a five-, six-, or seven-membered, saturated or unsaturated (including aromatic) heterocycle, containing from one to four heteroatoms each independently selected from nitrogen, oxygen and sulfur, said aryl or Het being substituted with $R^{24}$,
wherein $R^{24}$ is selected from H, halo, $(C_{1-6})$alkyl, —$NH_2$, —NH$(C_{1-6})$alkyl, —NH$(C_{3-6})$cycloalkyl, —NHCOO $(C_{1-6})$alkyl, —NHCOO$(C_{3-6})$cycloalkyl, —NHCO $(C_{1-6})$alkyl, —NHCO$(C_{3-6})$cycloalkyl, and —NHCONR$^{21}$R$^{22}$ wherein $R^{21}$ is selected from H, $(C_{1-6})$alkyl and $R^{22}$ is selected from H and methyl; and
B is $(C_{1-6})$alkyl optionally substituted with halo, or B is —$(CH_2)_p$—$(C_{3-7})$cycloalkyl wherein p is 0-4, or B is a tetrahydrofuran ring linked through the C3 or C4 position of the ring;
then $R^C$ is not —NHSO$_2$R$^S$, wherein $R^S$ is $(C_{1-6})$alkyl or unsubstituted $(C_{3-7})$cycloalkyl.

R²:

Preferably R² is phenyl or Het wherein said Het is selected from the group consisting of:

[Structures: thiazole-R²⁴, thiazole-R²⁴, pyrrole-R²⁴, pyrazole-R²⁴, pyrazole-R²⁴, imidazole-R²⁴, imidazole-R²⁴, oxazole-R²⁴, oxadiazole-R²⁴, oxadiazole-R²⁴, pyridine-R²⁴, and dihydropyran-R²⁴]

More preferably R² is phenyl or Het wherein said Het is selected from the group consisting of:

[Structures: thiazole-R²⁴, thiazole-R²⁴, pyrrole-R²⁴, pyrazole-R²⁴, imidazole-R²⁴, imidazole-R²⁴, and pyridine-R²⁴]

Most preferably R² is Het wherein said Het is selected from the group consisting of:

[Structures: thiazole-R²⁴, thiazole-R²⁴; and pyrazole-R²⁴]

Preferably, R²⁴ is as defined hereinbelow.

Further included in the preferred embodiments of the invention are compounds of formula IA:

(IA)

[Chemical structure of formula IA]

wherein

B is $(C_{1-10})$alkyl, $(C_{3-7})$cycloalkyl or $(C_{1-4})$alkyl-$(C_{3-7})$cycloalkyl,
  a) wherein each said alkyl, cycloalkyl, and alkyl-cycloalkyl may be mono-, di- or tri-substituted with $(C_{1-3})$alkyl; and
  b) wherein each said alkyl, cycloalkyl, and alkyl-cycloalkyl may be mono- or di-substituted with substituents each independently selected from hydroxy and O—$(C_{1-6})$alkyl; and
  c) wherein each of said alkyl groups may be mono-, di- or tri-substituted with halogen; and
  d) wherein in each of said cycloalkyl groups being 5-, 6- or 7-membered, one or two —CH₂-groups not being directly linked to each other may be replaced by —O—;

X is O or NH;

L⁰ is H, —OH, —O—$(C_{1-4})$alkyl, —NH₂, —NH$(C_{1-4})$alkyl or —N($(C_{1-4})$alkyl)₂;

L¹, L² are each independently halogen, $(C_{1-4})$alkyl, $(C_{2-4})$alkynyl, —O—$(C_{1-4})$alkyl, —S—$(C_{1-4})$alkyl, —SO—$(C_{1-4})$alkyl, or —SO₂-$(C_{1-4})$alkyl; and
either L¹ or L² (but not both at the same time) may also be H; or L⁰ and L¹ or
L⁰ and L² may be covalently bonded to form, together with the two C-atoms to which they are linked, a 4-, 5- or 6-membered carbocyclic ring wherein one —CH₂-group and, in the case of 5- or 6-membered ring, one or two —CH₂-groups not being directly linked to each other, may be replaced each independently by —O— or NRᵃ to form a heterocyclic ring wherein Rᵃ is H or $(C_{1-4})$alkyl, and wherein said carbo- or heterocyclic ring is optionally mono- or di-substituted with $(C_{1-4})$alkyl;

R²⁴ is R²⁰, —NHCOR²⁰, —NHCOOR²⁰, —NHR²¹ or —NHCONR²¹R²², wherein
  R²⁰ is selected from $(C_{1-6})$alkyl, $(C_{3-7})$cycloalkyl and $(C_{1-4})$alkyl-$(C_{3-7})$cycloalkyl, wherein said cycloalkyl and alkyl-cycloalkyl may be mono-, di- or tri-substituted with $(C_{1-3})$alkyl;
  R²¹ is H or R²⁰ as defined above,
  R²² is H or methyl; and Rᶜ is hydroxy or —NHSO₂Rˢ wherein Rˢ is $(C_{1-6})$alkyl, $(C_{2-4})$alkenyl, $(C_{3-7})$cycloalkyl, $(C_{1-6})$alkyl-$(C_{3-7})$cycloalkyl, phenyl, naphthyl, pyridinyl, $(C_{1-4})$alkyl-phenyl, $(C_{1-4})$alkyl-naphthyl or $(C_{1-4})$alkyl-pyridinyl; each of which optionally being monosubstituted with nitro; and each of which optionally being mono-, di- or tri-substituted with substituents each independently selected from halogen, hydroxy, cyano, $(C_{1-6})$alkyl, $(C_{2-6})$alkenyl, O—$(C_{1-6})$alkyl, —CO—NH$_2$, —CO—NH$(C_{1-4})$alkyl, —CO—N$((C_{1-4})$alkyl$)_2$, —NH$_2$, —NH$(C_{1-4})$alkyl and —N$((C_{1-4})$alkyl$)_2$, wherein $(C_{1-6})$alkyl and O—$(C_{1-6})$alkyl are optionally substituted with one to three halogen atoms;

or $R^S$ is —N$(R^{N2})(R^{N1})$, wherein $R^{N1}$ and $R^{N2}$ are each independently selected from H, $(C_{1-6})$alkyl, $(C_{3-7})$cycloalkyl, $(C_{1-6})$alkyl-$(C_{3-7})$cycloalkyl, aryl and $(C_{1-6})$alkyl-aryl; wherein said $(C_{1-6})$alkyl, $(C_{3-7})$cycloalkyl, $(C_{1-6})$alkyl-$(C_{3-7})$cycloalkyl, aryl and $(C_{1-6})$alkyl-aryl are each optionally substituted with one or more substituents each independently selected from halogen, $(C_{1-6})$alkyl, hydroxy, cyano, O—$(C_{1-6})$alkyl, —NH$_2$, —NH$(C_{1-4})$alkyl, —N$((C_{1-4})$alkyl$)_2$, —CO—NH$_2$, —CO—NH$(C_{1-4})$alkyl, —CO—N$((C_{1-4})$alkyl$)_2$, —COOH, and —COO$(C_{1-6})$alkyl; or $R^{N2}$ and $R^{N1}$ are linked, together with the nitrogen to which they are bonded, to form a 3- to 7-membered monocyclic saturated or unsaturated heterocycle or a 9- or 10-membered bicyclic saturated or unsaturated heterocycle, each of which optionally containing from one to three further heteroatoms each independently selected from N, S and O, and each of which being optionally substituted with one or more substituents each independently selected from halogen, $(C_{1-6})$alkyl, hydroxy, cyano, O—$(C_{1-6})$alkyl, —NH$_2$, —NH$(C_{1-4})$alkyl, —N$((C_{1-4})$alkyl$)_2$, —CO—NH$_2$, —CO—NH$(C_{1-4})$alkyl, —CO—N$((C_{1-4})$alkyl$)_2$, —COOH, and —COO$(C_{1-6})$alkyl;

or a pharmaceutically acceptable salt or ester thereof;

with the proviso that when $L^0$ is H; one of $L^1$ or $L^2$ is H and the other $L^2$ or $L^1$ is halo or —O—$(C_{1-4})$alkyl; and $R^{24}$ is selected from H, halo, $(C_{1-4})$alkyl, —NH$_2$, —NH$(C_{1-6})$alkyl, —NH$(C_{3-6})$cycloalkyl, —NHCOO$(C_{1-6})$alkyl, —NHCOO, —NHCO$(C_{1-6})$alkyl, —NHCO$(C_{3-6})$cycloalkyl, and —NHCONR$^{21}$R$^{22}$ wherein R$^{21}$ is selected from H, $(C_{1-6})$alkyl and R$^{22}$ is selected from H and methyl; and B is $(C_{1-6})$alkyl optionally substituted with halo, or B is —$(CH_2)_p$—$(C_{3-7})$cycloalkyl wherein p is 0-4, or B is a tetrahydrofuran ring linked through the C3 or C4 position of the ring;

then $R^C$ is not —NHSO$_2$R$^S$, wherein R$^S$ is $(C_{1-6})$alkyl or unsubstituted $(C_{3-7})$cycloalkyl.

With respect to compounds of formula I and IA as defined above,

B is preferably selected from $(C_{2-8})$alkyl, $(C_{3-7})$cycloalkyl and $(C_{1-3})$alkyl-$(C_{3-7})$cycloalkyl, a) wherein said alkyl, cycloalkyl, and alkyl-cycloalkyl may be mono-, di- or tri-substituted with $(C_{1-3})$alkyl; and b) wherein said alkyl, cycloalkyl and alkyl-cycloalkyl may be mono- or di-substituted with substituents each independently selected from hydroxy and O—$(C_{1-4})$alkyl; and c) wherein each of said alkyl groups may be mono-, di- or tri-substituted with fluorine or mono-substituted with chlorine or bromine; and d) wherein in each of said cycloalkyl groups being 5-, 6- or 7-membered, one or two —CH$_2$-groups not being directly linked to each other may be replaced by —O— such that the O-atom is linked to the group X via at least two C-atoms.

More preferably, B is selected from ethyl, n-propyl, i-propyl, n-butyl, 1-methylpropyl, 2-methylpropyl, tert-butyl, cyclopropyl, cyclobutyl, cyclopentyl and cyclohexyl, a) wherein each of said groups is optionally substituted with 1 to 3 substituents each independently selected from methyl and ethyl;

b) wherein each of said groups is optionally mono- or di-substituted with substituents each independently selected from hydroxy, methoxy and ethoxy; and c) wherein each of said alkyl groups may be mono-, di- or tri-substituted with fluorine or mono-substituted with chlorine or bromine; and d) wherein in each of said cycloalkyl groups being 5-, 6- or 7-membered, one or two —CH$_2$-groups not being directly linked to each other may be replaced by —O— such that the O-atom is linked to the group X via at least two C-atoms.

B is even more preferably selected from ethyl, 1-methylethyl, 1,1-dimethylethyl, propyl, 1-methylpropyl, 2-methylpropyl, 1,1-dimethylpropyl, 1,2-dimethylpropyl, 2,2-dimethylpropyl, 1,1,2-trimethylpropyl, 1,2,2-trimethylpropyl, 1-ethylpropyl, 1-ethyl-2-methylpropyl, 1-(1-methylethyl)-2-methylpropyl, 1-ethyl-2,2-dimethylpropyl, butyl, 1-methylbutyl, 2-methylbutyl, 3-methylbutyl, 1,2-dimethylbutyl, 1,1-dimethylbutyl, 1,3-dimethylbutyl, 2,2-dimethylbutyl, 2,3-dimethylbutyl, 3,3-dimethylbutyl, 1,2,2-trimethylbutyl, 1,2,3-trimethylbutyl, 2,2,3-trimethylbutyl, 2,3,3-trimethylbutyl and 2,2,3-trimethylbutyl, whereby these alkyl groups may be substituted with chlorine or bromine, or with 1, 2 or 3 fluorine substituents. Examples of preferred fluorinated alkyl groups include, but are not limited to, 2-fluoroethyl, 3-fluoropropyl and 3,3,3-trifluoropropyl.

In addition, even more preferably, B is cyclopropyl, cyclobutyl, cyclopentyl, or cyclohexyl or is selected from the following formulas, wherein one or two CH$_2$-groups of a cycloalkyl group is replaced by oxygen:

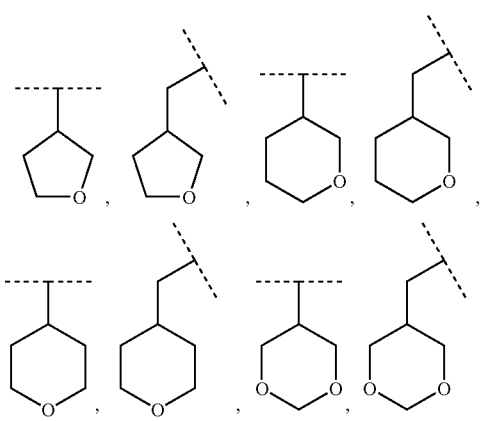

From the above list, cycloalkyl and alkyl-cycloalkyl groups optionally comprising 1 or 2 O-atoms are optionally substituted with 1, 2 or 3 methyl groups. Especially those cycloalkyl groups, optionally comprising 1 or 2 O-atoms, are preferred, wherein the α-C-atom is substituted with methyl.

Further examples of preferred substituted cyclic groups are

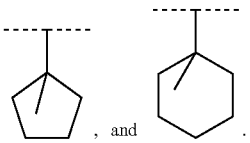, and

Yet more preferably B is selected from tert-butyl, cyclopropyl, cyclobutyl, cyclopentyl, cyclohexyl, 1-methylcyclopentyl and 1-methylcyclohexyl.

Most preferably B is cyclopentyl.

According to one embodiment of this invention X is O.

According to another embodiment of this invention X is NH.

$L^0$ is preferably selected from H, —OH, —OCH$_3$, —OC$_2$H$_5$, —OC$_3$H$_7$, —OCH(CH$_3$)$_2$, —NHCH$_3$, —NHC$_2$H$_5$, —NHC$_3$H$_7$, —NHCH(CH$_3$)$_2$, —N(CH$_3$)$_2$, —N(CH$_3$)C$_2$H$_5$, —N(CH$_3$)C$_3$H$_7$ and —N(CH$_3$)CH(CH$_3$)$_2$.

More preferably, $L^0$ is selected from H, —OH, —OCH$_3$ and —N(CH$_3$)$_2$.

Most preferably, $L^0$ is —OCH$_3$. Alternatively most preferably, $L^0$ is H.

$L^1$ and $L^2$ are preferably each independently selected from: halogen, —CH$_3$, —C≡CH, —OCH$_3$, —OC$_2$H$_5$, —SMe, —SOMe, and SO$_2$Me whereby either $L^1$ or $L^2$, but not both at the same time, may be H.

More preferably $L^1$ is CH$_3$; —C≡CH, —F, —Cl, —Br, —OMe, —SMe, or —SO$_2$Me; and $L^2$ is H.

Therefore, even more preferably $L^0$ is —OCH$_3$; $L^1$ is CH$_3$, —F, —Cl, —Br or —OMe; and $L^2$ is H.

In an alternative even more preferable embodiment, $L^0$ is H; $L^1$ is CH$_3$, —C≡CH, —F, —Cl, —Br, —OMe, —SMe, or —SO$_2$Me; and $L^2$ is H.

Most preferably within the scope of this embodiment, $L^0$ is H; $L^1$ is CH$_3$, —C≡CH, —SMe, or —SO$_2$Me; and $L^2$ is H.

In the case $L^0$ and $L^1$ are covalently bonded to form together with the quinoline residue to which they are linked a ring system, this ring system is preferably selected from:

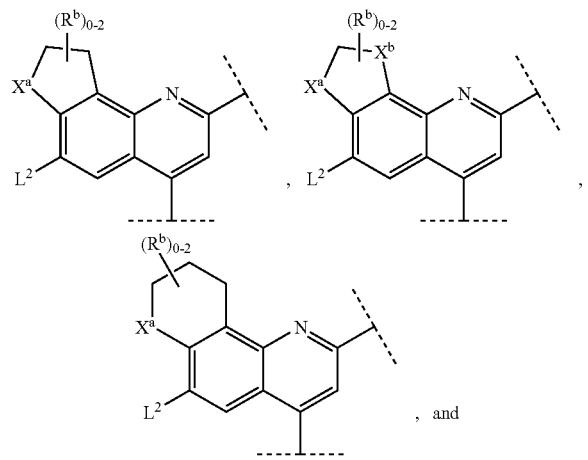

wherein $X^a$, $X^b$ are each independently selected from CH$_2$, O and NR$^a$; most preferably O;

$R^a$ is each independently H or (C$_{1-4}$)alkyl;

$R^b$ is each independently (C$_{1-4}$)alkyl;

$L^2$ is as defined; preferably H or methyl, particularly H.

In the case $L^0$ and $L^2$ are covalently bonded to form together with the quinoline residue to which they are linked a ring system, this ring system is preferably selected from:

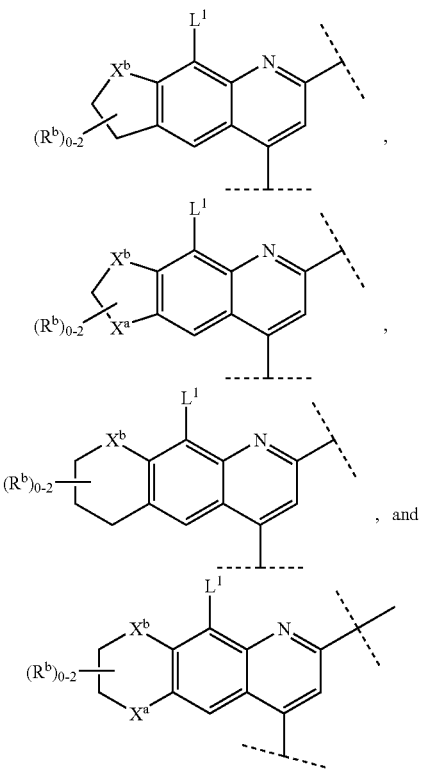

wherein $X^a$, $X^b$ are each independently selected from CH$_2$, O and NR$^a$; most preferably O;

$R^a$ is each independently H or (C$_{1-4}$)alkyl;

$R^b$ is each independently (C$_{1-4}$)alkyl;

$L^1$ is as defined; preferably H or methyl, particularly H.

More preferably, $L^0$ and $L^1$ are covalently bonded to form, together with the quinoline residue to which they are linked, a ring system which is selected from:

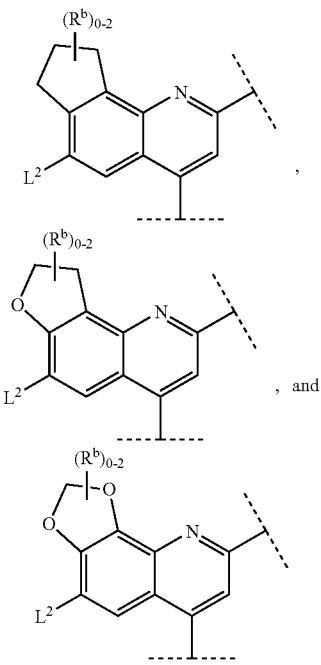

wherein each $R^b$ is independently $(C_{1-4})$alkyl and $L^2$ is as defined; preferably H or methyl, particularly H.

Most preferably, $L^0$ and $L^1$ are covalently bonded to form together with the quinoline residue to which they are linked a ring system selected from

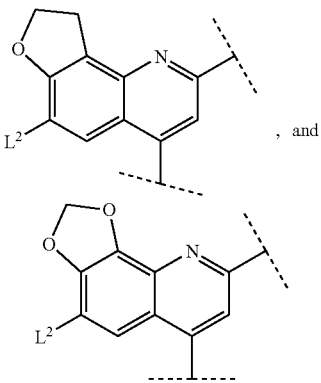

wherein $L^2$ is H or —CH$_3$, preferably H.
$R^{24}$ is preferably selected from $R^{20}$, —NHCOR$^{20}$, —NHCOOR$^{20}$, —NHR$^{21}$ and —NHCONR$^{21}R^{22}$;
 wherein $R^{20}$ is selected from $(C_{1-6})$alkyl, $(C_{3-7})$cycloalkyl, and $(C_{1-3})$alkyl-$(C_{3-7})$cycloalkyl, wherein said cycloalkyl and alkyl-cycloalkyl may be mono-, di- or tri-substituted with $(C_{1-3})$alkyl; and
 $R^{21}$ is H or $R^{20}$ as defined above; and
 $R^{22}$ is H or methyl; most preferably H.
More preferably, $R^{24}$ is $R^{20}$, —NHCOR$^{20}$, —NHCOOR$^{20}$, —NHR$^{21}$ or —NHCONR$^{21}R^{22}$, wherein
$R^{20}$ is selected from methyl, ethyl, n-propyl, i-propyl, n-butyl, 1-methylpropyl, 2-methylpropyl, tert-butyl, 2,2-dimethylpropyl, 1,1-dimethylpropyl, 1,2-dimethylpropyl, 1,2,2-trimethylpropyl; cyclopropyl, cyclobutyl, cyclopentyl, cyclohexyl, cyclopropyl-methyl, cyclobutylmethyl, cyclopentylmethyl, and cyclohexylmethyl, each of said cycloalkyl and alkyl-cycloalkyl groups being optionally substituted with 1 to 3 substituents each independently selected from methyl and ethyl, in particular methyl; and
$R^{21}$ is H or $R^{20}$ as defined above; and
$R^{22}$ is H or methyl; most preferably H.
Most preferably $R^{24}$ is —NHCOR$^{20}$, —NHCOOR$^{20}$, or —NHR$^{21}$, wherein $R^{20}$ and $R^{21}$ are defined as hereinbefore.
Preferably, $R^{24}$ is selected from:
a) amino, N-methylamino, N-ethylamino, N-propylamino, N-(1-methylethyl)amino, N-(1,1-dimethylethyl)amino, N-(2-methylpropyl)amino, N-(1-methylpropyl)amino, N-(2,2-dimethylpropyl)amino, N-(1,2-dimethylpropyl)amino, N-(1,1-dimethylpropyl)amino, N-cyclopropylamino, N-cyclobutylamino-, N-cyclopentylamino-, N-cyclohexylamino-, N-(cyclopropylmethyl)amino, N-cyclobutylmethyl)amino, N-(cyclopentylmethyl)amino, and N-(cyclohexylmethyl)amino;
b) methylcarbonylamino, ethylcarbonylamino, 1-methylethylcarbonylamino, 1,1-dimethylethylcarbonylamino, propylcarbonylamino, 2-methylpropylcarbonyl-amino, 1-methylpropylcarbonylamino, 2,2-dimethylpropylcarbonylamino, 1,2-dimethylpropylcarbonylamino, 1,1-dimethylpropylcarbonylamino, cyclopropylcarbonylamino, cyclobutylcarbonylamino, cyclopentylcarbonylamino, cyclohexylcarbonylamino, cyclopropylmethylcarbonylamino, cyclobutylmethylcarbonylamino, cyclopentylmethylcarbonylamino, and cyclohexylmethylcarbonylamino; and
c) methoxycarbonylamino, ethoxycarbonylamino, 1-methylethoxycarbonylamino, propoxycarbonylamino, tert-butoxycarbonylamino, cyclopropyloxycarbonylamino, cyclobutyloxycarbonylamino, cyclopentyloxycarbonylamino, cyclohexyloxycarbonylamino, cyclopropylmethoxycarbonylamino, cyclobutylmethoxycarbonylamino, cyclopentylmethoxycarbonylamino, and cyclohexylmethoxycarbonylamino;
wherein all said cycloalkyl or alkyl-cycloalkyl groups may be mono- or disubstituted with methyl.
Preferably, $R^{20}$ and $R^{21}$ are each independently selected from: methyl, ethyl, n-propyl, i-propyl, n-butyl, 1-methylpropyl, 2-methylpropyl, tert-butyl, 2,2-dimethylpropyl, 1,1-dimethylpropyl, 1,2-dimethylpropyl, 1,2,2-trimethylpropyl, cyclopropyl, cyclobutyl, cyclopentyl, cyclohexyl, cyclopropylmethyl, cyclobutylmethyl, cyclopentylmethyl, and cyclohexylmethyl, each of said cycloalkyl or alkyl-cycloalkyl groups optionally being mono- or di-substituted with methyl or ethyl.
More preferably, $R^{20}$ and $R^{21}$ are each independently selected from: methyl, ethyl, n-propyl, i-propyl, 2,2-dimethylpropyl and cyclopentylmethyl.
According to a preferred embodiment, the group $R^C$ is hydroxy.
According to an alternative preferred embodiment, $R^C$ is —NHSO$_2R^S$ wherein $R^S$ is methyl, ethyl, n-propyl, i-propyl, n-butyl, 1-methylpropyl, 2-methylpropyl, tert-butyl, ethenyl, 1-propenyl, 2-propenyl, cyclopropyl, cyclobutyl, cyclopentyl, cyclohexyl, cyclopropylmethyl, cyclobutylmethyl, cyclopentylmethyl, cyclohexylmethyl, phenyl, naphthyl, pyridinyl, phenylmethyl, naphthylmethyl or pyridinylmethyl;
a) each of which optionally being mono-, di- or tri-substituted with substituents each independently selected from fluorine, methyl, ethyl and propyl; and b) each of which optionally being mono- or disubstituted with substituents each independently selected from hydroxy, trifluoromethyl, methoxy and trifluoromethoxy; and
c) each of which optionally being monosubstituted with a substituent selected from chlorine, bromine, cyano, nitro, ethenyl, 1-propenyl, 2-propenyl, —CO—NH$_2$, —CO—NHCH$_3$, —CO—N(CH$_3$)$_2$, —NH$_2$, —NH(CH$_3$) and —N(CH$_3$)$_2$; or R$^S$ is —N(R$^{N2}$)(R$^{N1}$),
wherein R$^{N1}$ and R$^{N2}$ are each independently selected from H, (C$_{1-4}$)alkyl, (C$_{3-7}$)cycloalkyl, (C$_{1-3}$)alkyl-(C$_{3-7}$)cycloalkyl, phenyl, and (C$_{1-3}$)alkyl-phenyl; wherein said (C$_{1-4}$)alkyl, (C$_{3-7}$)cycloalkyl, (C$_{1-3}$)alkyl-(C$_{3-7}$)cycloalkyl, phenyl and (C$_{1-3}$)alkyl-phenyl are optionally substituted with one, two or three substituents each independently selected from halogen, (C$_{1-6}$)alkyl, hydroxy, cyano, O—(C$_{1-6}$)alkyl, —NH$_2$, —NH(C$_{1-4}$)alkyl, —N((C$_{1-4}$)alkyl)$_2$, —CO—NH$_2$, —CO—NH(C$_{1-4}$)alkyl, —CO—N((C$_{1-4}$)alkyl)$_2$, —COOH, and —COO(C$_{1-6}$)alkyl; or R$^{N2}$ and R$^{N1}$ are linked, together with the nitrogen to which they are bonded, to form a 5 or 6-membered monocyclic heterocycle which may be saturated or unsaturated, optionally containing from one to three further heteroatoms each independently selected from N, S and O, and optionally substituted with one, two or three substituents each independently selected from halogen, (C$_{1-6}$)alkyl, hydroxy, cyano, O—(C$_{1-6}$)alkyl, —NH$_2$, —NH(C$_{1-4}$)alkyl, —N((C$_{1-4}$)alkyl)$_2$, —CO—NH$_2$, —CO—NH(C$_{1-4}$)alkyl, —CO—N((C$_{1-4}$)alkyl)$_2$, —COOH, and —COO(C$_{1-6}$)alkyl.

More preferably within the scope of this embodiment, the group R$^C$ is selected from —NHSO$_2$-methyl, —NHSO$_2$-ethyl, —NHSO$_2$-(1-methyl)ethyl, —NHSO$_2$-propyl, —NHSO$_2$-cyclopropyl, —NHSO$_2$—CH$_2$-cyclopropyl, —NHSO$_2$-(1-methylcyclopropyl), —NHSO$_2$-cyclobutyl, —NHSO$_2$-cyclopentyl, —NHSO$_2$-phenyl and —NHSO$_2$N(CH$_3$)$_2$.

Most preferably, the group R$^C$ is selected from —NHSO$_2$-cyclopropyl, —NHSO$_2$-(1-methylcyclopropyl) and —NHSO$_2$N(CH$_3$)$_2$.

Therefore, a preferred embodiment of the invention includes compounds of formula IA:

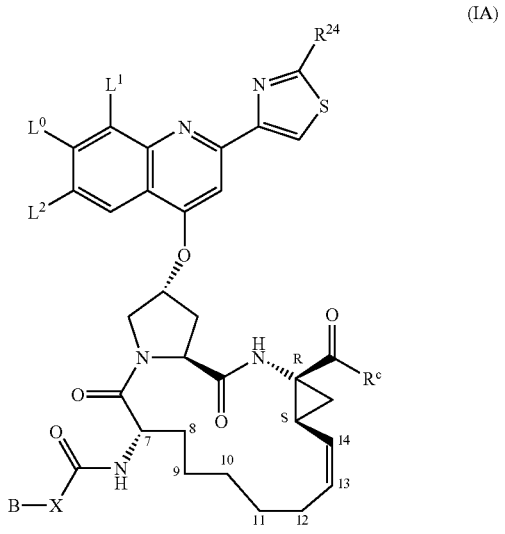

(IA)

wherein
B is cyclopentyl;
X is O or NH;
L$^0$ is —OCH$_3$; L$^1$ is CH$_3$, —F, —Cl, —Br or —OMe; and L$^2$ is H;
R$^{24}$ is —NHCOR$^{20}$, —NHCOOR$^{20}$, or —NHR$^2$, wherein R$^{20}$ and R$^{21}$ are each independently selected from: methyl, ethyl, n-propyl, i-propyl, 2,2-dimethylpropyl and cyclopentylmethyl; and
R$^C$ is hydroxy.

An alternative preferred embodiment of the invention includes compounds of formula IA:

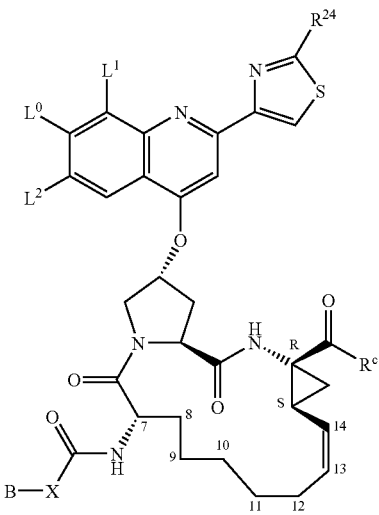

(IA)

wherein
B is cyclopentyl;
X is O or NH;
L$^0$ is —OCH$_3$; L$^1$ is CH$_3$, —F, —Cl, —Br or —OMe; and L$^2$ is H;
R$^{24}$ is —NHCOR$^{20}$, —NHCOOR$^{20}$, or —NHR$^{21}$, wherein R$^{20}$ and R$^{21}$ are each independently selected from: methyl, ethyl, n-propyl, i-propyl, 2,2-dimethylpropyl and cyclopentylmethyl; and
R$^C$ is —NHSO$_2$-cyclopropyl, —NHSO$_2$-(1-methylcyclopropyl) or —NHSO$_2$N(CH$_3$)$_2$.

Another alternative preferred embodiment of the invention includes compounds of formula IA:

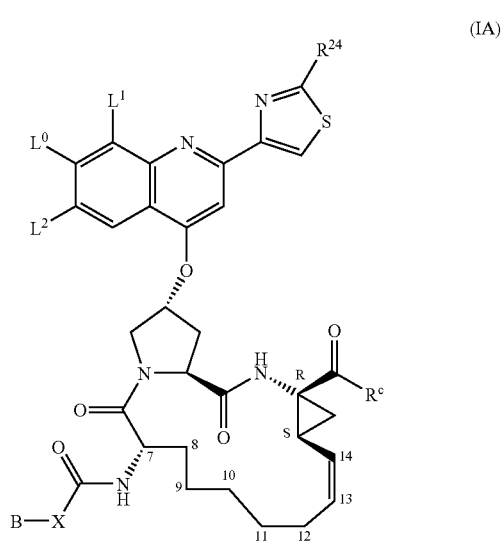

(IA)

wherein
B is cyclopentyl;
X is O or NH;
$L^0$ is H; $L^1$ is $CH_3$, —C≡CH, —F, —Cl, —Br, —OMe, —SMe, or —$SO_2$Me; and $L^2$ is H;
$R^{24}$ is —$NHCOR^{20}$, —$NHCOOR^{20}$, or —$NHR^{21}$, wherein $R^{20}$ and $R^{21}$ are each independently selected from: methyl, ethyl, n-propyl, i-propyl, 2,2-dimethylpropyl and cyclopentylmethyl; and
$R^C$ is hydroxy.

Still another alternative preferred embodiment of the invention includes compounds of formula IA:

(IA)

wherein
B is cyclopentyl;
X is O or NH;
$L^0$ is H; $L^1$ is $CH_3$, —C CH, —F, —Cl, —Br, —OMe, —SMe, or —$SO_2$Me; and $L^2$ is H;
$R^{24}$ is —$NHCOR^{20}$, —$NHCOOR^{20}$, or —$NHR^{21}$, wherein $R^{20}$ and $R^{21}$ are each independently selected from: methyl, ethyl, n-propyl, i-propyl, 2,2-dimethylpropyl and cyclopentylmethyl; and
$R^C$ is —$NHSO_2$-cyclopropyl, —$NHSO_2$-(1-methylcyclopropyl) or —$NHSO_2N(CH_3)_2$;
with the proviso that
when $L^1$ is —F, —Cl, —Br or —OMe; and
$R^{24}$ is —$NHCOR^{20}$, —$NHCOOR^{20}$, or —$NHR^{21}$, wherein $R^{20}$ and $R^{21}$ are each independently selected from: methyl, ethyl, n-propyl, i-propyl and 2,2-dimethylpropyl;
then $R^C$ is not —$NHSO_2$-cyclopropyl.

Examples of most preferred compounds according to this invention are each single compound listed in the following Tables 1 to 3.

As discussed above, included within the scope of this invention is a pharmaceutical composition comprising an anti-hepatitis C virally effective amount of a compound of formula 1, or a pharmaceutically acceptable salt or ester thereof, in admixture with at least one pharmaceutically acceptable carrier medium or auxiliary agent.

According to a further aspect of this embodiment the pharmaceutical composition according to this invention further comprises a therapeutically effective amount of at least one other antiviral agent.

According to an alternate embodiment, the pharmaceutical composition of this invention may additionally comprise at least one other anti-HCV agent. Examples of anti-HCV agents include, α-(alpha), β- (beta), δ- (delta), γ- (gamma), ω- (omega) or τ-(tau) interferon, pegylated α-interferon, ribavirin and amantadine.

According to another alternate embodiment, the pharmaceutical composition of this invention may additionally comprise at least one other inhibitor of HCV NS3 protease.

According to another alternate embodiment, the pharmaceutical composition of this invention may additionally comprise at least one inhibitor of HCV polymerase.

According to yet another alternate embodiment, the pharmaceutical composition of this invention may additionally comprise at least one inhibitor of other targets in the HCV life cycle, including but not limited to, helicase, NS2/3 protease or internal ribosome entry site (IRES).

The pharmaceutical composition of this invention may be administered orally, parenterally or via an implanted reservoir. Oral administration or administration by injection is preferred. The pharmaceutical composition of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra-articular, intrasynovial, intrasternal, intrathecal, and intralesional injection or infusion techniques.

The pharmaceutical composition may be in the form of a sterile injectable preparation, for example, as a sterile injectable aqueous or oleaginous suspension.

This suspension may be formulated according to techniques known in the art using suitable dispersing or wetting agents (such as, for example Tween 80) and suspending agents.

The pharmaceutical composition of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

Other suitable vehicles or carriers for the above noted formulations and compositions can be found in standard pharmaceutical texts, e.g. in "Remington's Pharmaceutical Sciences", The Science and Practice of Pharmacy, $19^{th}$ Ed. Mack Publishing Company, Easton, Pa., (1995).

Dosage levels of between about 0.01 and about 100 mg/kg body weight per day, preferably between about 0.1 and about 50 mg/kg body weight per day of the protease inhibitor compound described herein are useful in a monotherapy for the prevention and treatment of HCV mediated disease. Typically, the pharmaceutical composition of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician. Generally, treatment is initiated with small dosages substantially less than the optimum dose of the peptide. Thereafter, the dosage is increased by small increments until the optimum effect under the circumstances is reached. In general, the compound is most desirably administered at a concentration level that will generally afford antivirally effective results without causing any harmful or deleterious side effects.

When the composition of this invention comprises a combination of a compound of formula I and one or more additional therapeutic or prophylactic agent, both the compound and the additional agent should be present at dosage levels of between about 10 to 100%, and more preferably between about 10 and about 80% of the dosage normally administered in a monotherapy regimen.

When these compounds, including their pharmaceutically acceptable salts and esters thereof, are formulated together with a pharmaceutically acceptable carrier, the resulting composition may be administered in vivo to mammals, such as man, to inhibit HCV NS3 protease or to treat or prevent HCV virus infection. Such treatment may also be achieved using a compound of this invention in combination with another antiviral agent. Preferred other antiviral agents are described within the Definitions section and the section of preferred pharmaceutical compositions according to this invention and include, but are not limited to: α-(alpha), β-(beta), δ-(delta), ω-(omega), γ-(gamma) or τ-(tau)-interferon, ribavirin, amantadine; other inhibitors of HCV NS3 protease; inhibitors of HCV polymerase; inhibitors of other targets in the HCV life cycle, which include but not limited to, helicase, NS2/3 protease, or internal ribosome entry site (IRES); or combinations thereof. The additional agents may be combined with compounds of this invention to create a single dosage form. Alternatively these additional agents may be separately administered to a mammal as part of a multiple dosage form.

Accordingly, another embodiment of this invention provides a method of inhibiting HCV NS3 protease activity in a mammal by administering a compound of the formula I, including a pharmaceutically acceptable salt or ester thereof.

In a preferred embodiment, this method is useful in decreasing the NS3 protease activity of the hepatitis C virus infecting a mammal.

As discussed above, combination therapy is contemplated wherein a compound of formula 1, or a pharmaceutically acceptable salt or ester thereof, is co-administered with at least one additional antiviral agent. Preferred antiviral agents are described hereinbefore and examples of such agents are provided in the Definitions section. These additional agents may be combined with the compounds of this invention to create a single pharmaceutical dosage form. Alternatively these additional agents may be separately administered to the patient as part of a multiple dosage form, for example, using a kit. Such additional agents may be administered to the patient prior to, concurrently with, or following the administration of a compound of formula 1, or a pharmaceutically acceptable salt or ester thereof.

A compound of formula 1, or a pharmaceutically acceptable salt or ester thereof, set forth herein may also be used as a laboratory reagent. Furthermore a compound of this invention, including a pharmaceutically acceptable salt or ester thereof, may also be used to treat or prevent viral contamination of materials and therefore reduce the risk of viral infection of laboratory or medical personnel or patients who come in contact with such materials (e.g. blood, tissue, surgical instruments and garments, laboratory instruments and garments, and blood collection apparatuses and materials).

A compound of formula 1, including a pharmaceutically acceptable salt or ester thereof, set forth herein may also be used as a research reagent. A compound of formula 1, including a pharmaceutically acceptable salt or ester thereof, may also be used as positive control to validate surrogate cell-based assays or in vitro or in vivo viral replication assays.

Methodology

In general, the compound of formula I and intermediates therefore are prepared by known methods using reaction conditions which are known to be suitable for the reactants. Several such methods are disclosed in WO 00/09543, WO 00/09558 and WO 00/59929 incorporated herein by reference.

Particularly, the synthesis of the P3 fragment ((2S)-N-protected-amino non-8-enoic acid) and the P1 fragment ((1R, 2S) 1- amino-2-ethenylcyclopropanecarboxylic acid) have been described in detail in WO 00/59929.

I. General Multi-Step Synthetic Method

In general, the present invention is directed to compounds of formula I which can be prepared by a general multi-step synthetic method. Specifically, compounds of the following formula I are prepared by the following process:

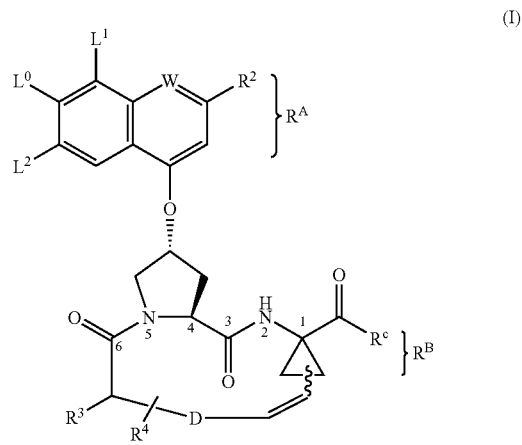

wherein W, $L^0$, $L^1$, $L^2$, $R^2$, $R^3$, $R^4$, D and $R^C$ are as defined herein, said process comprising the following steps:

(i) reacting a compound of formula II:

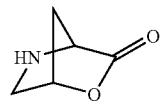
(II)

or a salt thereof, with a compound of formula III:

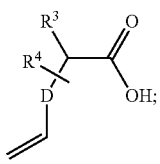
(III)

(ii) reacting the resulting compound of formula IV obtained in step (i):

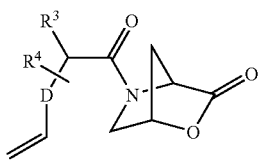
(IV)

with an aminocyclopropane compound of formula V

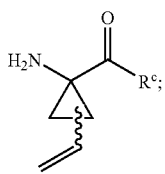
(V)

(iii) reacting the resulting compound of formula VI obtained in step (ii):

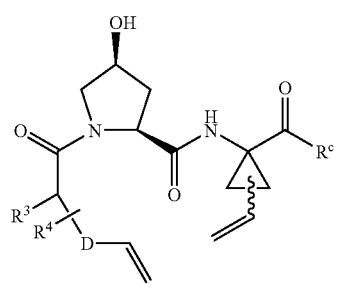
(VI)

with a compound of formula VII:

V-SO$_2$—R$^{12}$ (VII)

wherein V represents a suitable leaving group and R$^{12}$ is selected from p-tolyl, p-bromophenyl, p-nitrophenyl, methyl, trifluoromethyl, perfluorobutyl and 2,2,2-trifluoroethyl;

(iv) cyclizing of the resulting diene compound of formula VIII obtained in step (iii):

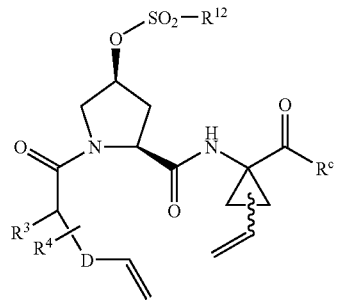
(VIII)

in the presence of a ruthenium catalyst; and (v) reacting the resulting compound of formula IX obtained in step (iv):

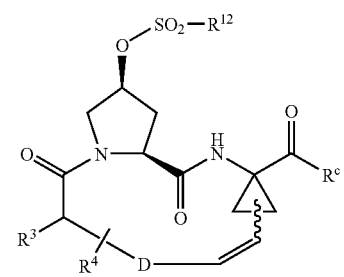
(IX)

with a compound of formula X:

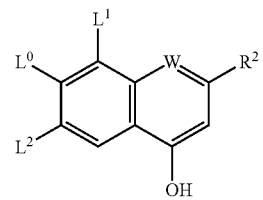
(X)

to obtain a compound of formula I:

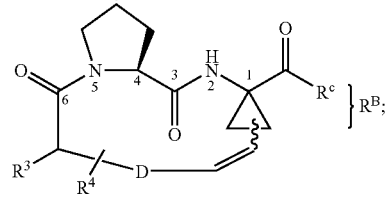
(I)

and when $R^C$ is a carboxylic acid ester group in the resulting compound of formula 1, optionally subjecting the compound of formula I to hydrolysis conditions to obtain a compound of formula I wherein $R^C$ is a carboxylic acid group.

II. Sulfonamides and Sulfamides

Compounds of formula I wherein $R^C$ is —NHSO$_2$R$^S$ as defined herein are prepared by coupling the corresponding acid of formula I (i.e. $R^C$ is hydroxy) with an appropriate sulfonamide of formula $R^S$ SO$_2$NH$_2$ in the presence of a coupling agent under standard conditions. Although several commonly used coupling agents can be employed, TBTU and HATU have been found to be practical. The sulfonamides or sulfamides are available commercially or can be prepared by known methods or by procedures described in the following examples.

III. Alternative Methodology

The following scheme provides an alternative process using known methods for preparing a key intermediate of formula 1-8 from acyclic intermediates:

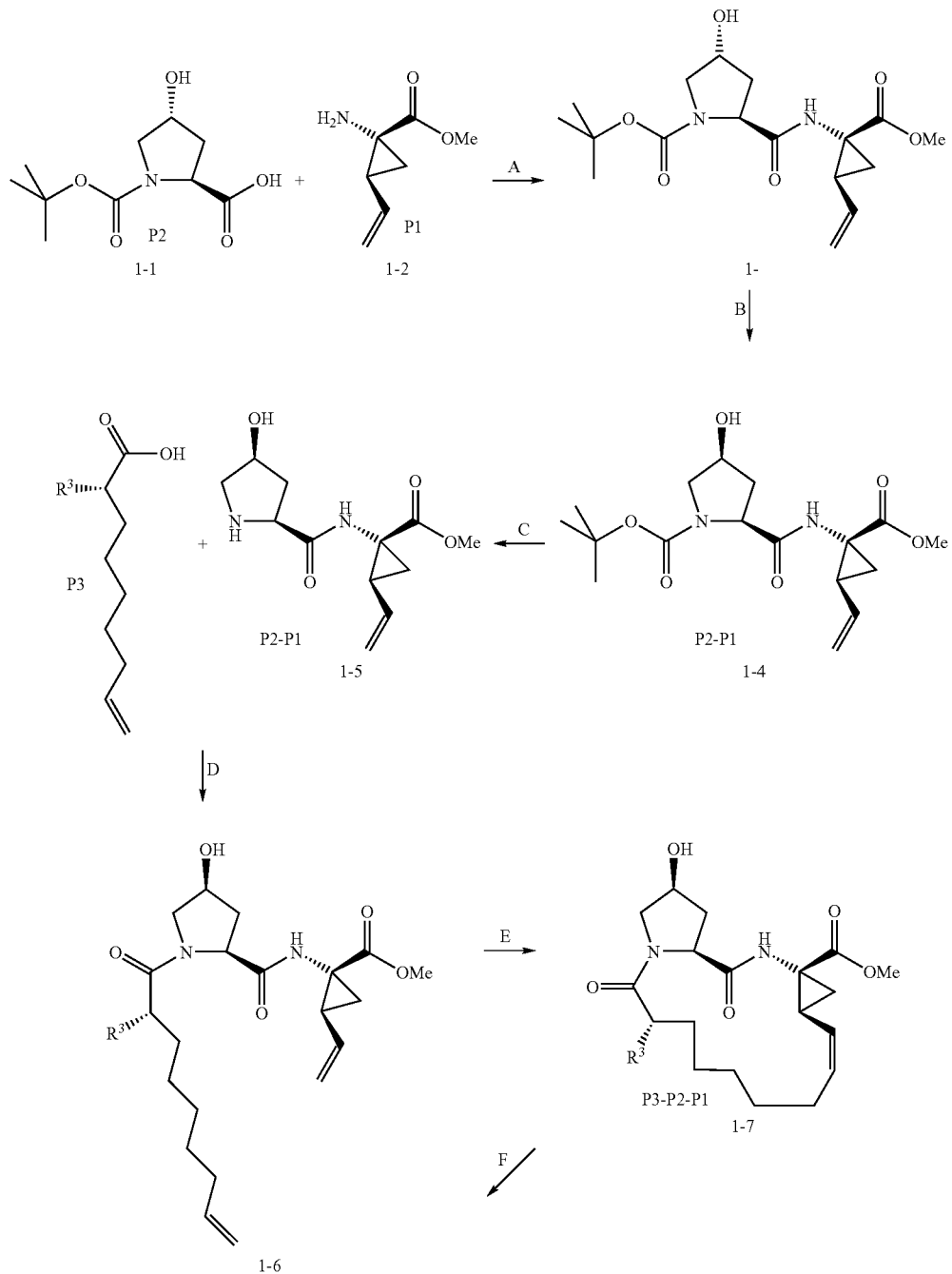

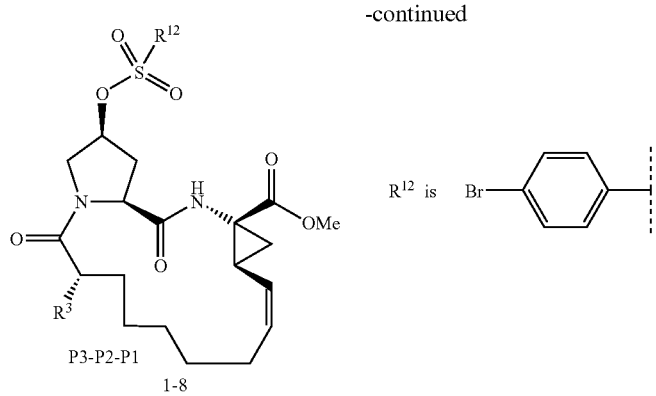

Steps A, C, D: Briefly, the P1, P2, and P3 moieties can be linked by well known peptide coupling techniques generally disclosed in WO 00/09543 & WO 00/09558.

Step B: This step involves the inversion of configuration of the 4-hydroxy substituent. There are several ways in which this can be accomplished as will be recognized by persons skilled in the art. One example of a convenient method is the well known Mitsunobu reaction (Mitsunobu *Synthesis* 1981, January, 1-28; Rano et al. *Tet. Lett.* 1994, 36, 3779-3792; Krchnak et al. *Tet Lett.* 1995, 36, 6193-6196).

Step E: The formation of the macrocycle can be carried out via an olefin metathesis using a Ru-based catalyst such as the one reported by Miller, S. J.; Blackwell, H. E.; Grubbs, R. H. *J. Am. Chem. Soc.* 1996, 118, 9606-9614 (a); Kingsbury, J. S.; Harrity, J. P. A.; Bonitatebus, P. J.; Hoveyda, A. H. *J. Am. Chem. Soc.* 1999, 121, 791-799 (b) and Huang, J.; Stevens, E. D.; Nolan, S. P.; Petersen, J. L.; *J. Am. Chem. Soc.* 1999, 121, 2674-2678 (c) or as described in WO 00/59929. It will also be recognized that catalysts containing other transition metals such as Mo can be used for this reaction.

(a)

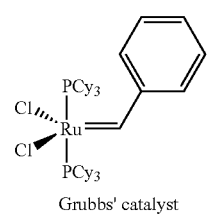

Grubbs' catalyst (b)

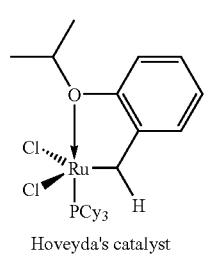

Hoveyda's catalyst (c)

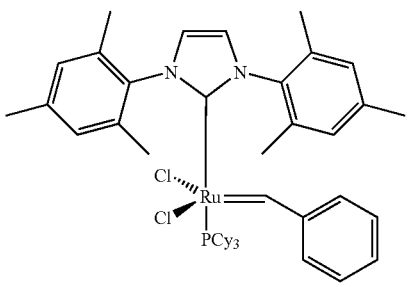

Nolan's catalyst

Step F: Conversion of the hydroxyl group of the proline to a suitable leaving group (i.e. brosylate) was carried out by reacting the free OH with the corresponding halo-derivative (i.e. 4-bromobenzenesulfonyl chloride), to give intermediate 1-8, wherein $R^{12}$ is p-bromophenyl.

Subsequent conversion of the key intermediate of formula 1-8 to the compounds of formula I of this invention is disclosed in detail in the examples hereinafter.

IV. Introduction of the Quinoline Moiety to Form Compounds of General Formula (I'):

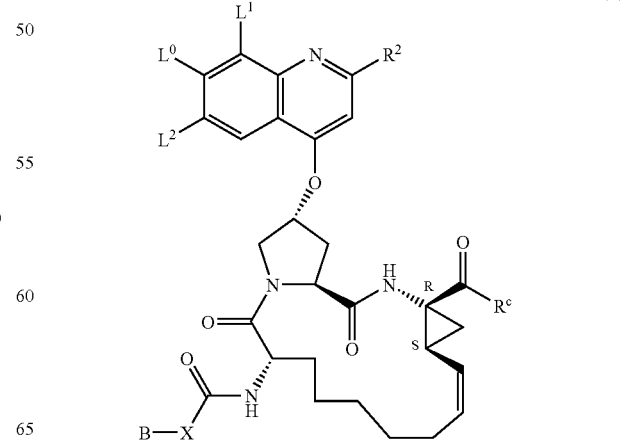

said process comprising reacting a macrocyclic compound of formula (IXa or 1-8) with a compound of formula (Xa):

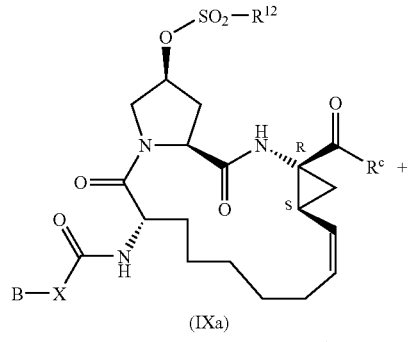

(IXa)

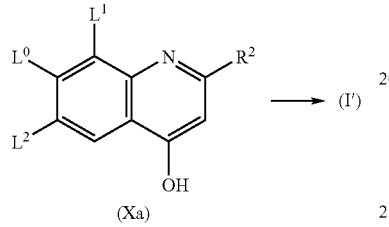

(Xa)

and when $R^C$ is a carboxylic acid ester group in the resulting compound of formula (I'), optionally subjecting the compound of formula (I') to hydrolysis conditions to obtain a compound of formula I wherein $R^C$ is a carboxylic acid group.

Compounds of formula (IXa) and (Xa) are mixed in a polar non-protic organic solvent (such as THF, dioxane, dicholoromethane, chloroform, N-methylpyrrolidone, dimethyl sulfoxide, dimethylformamide, acetone, or methylisobutylketone) in the presence of an inorganic or organic base (such as cesium carbonate, or DBU) at 40° C. to 100° C. until completion of reaction. Aqueous workup followed by crystallization from a suitable solvent such as ethyl acetate-heptane or ethyl acetate/methyl cyclohexane provides the compounds of formula (I').

V. Synthesis of Compounds of Formula (IA)

Compounds where $R^2$ is 2-amino-4-thiazolyl derivatives can be synthesized according to the following scheme 2:

SCHEME 2

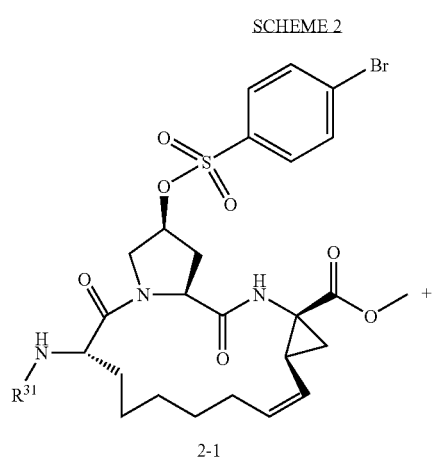

2-1

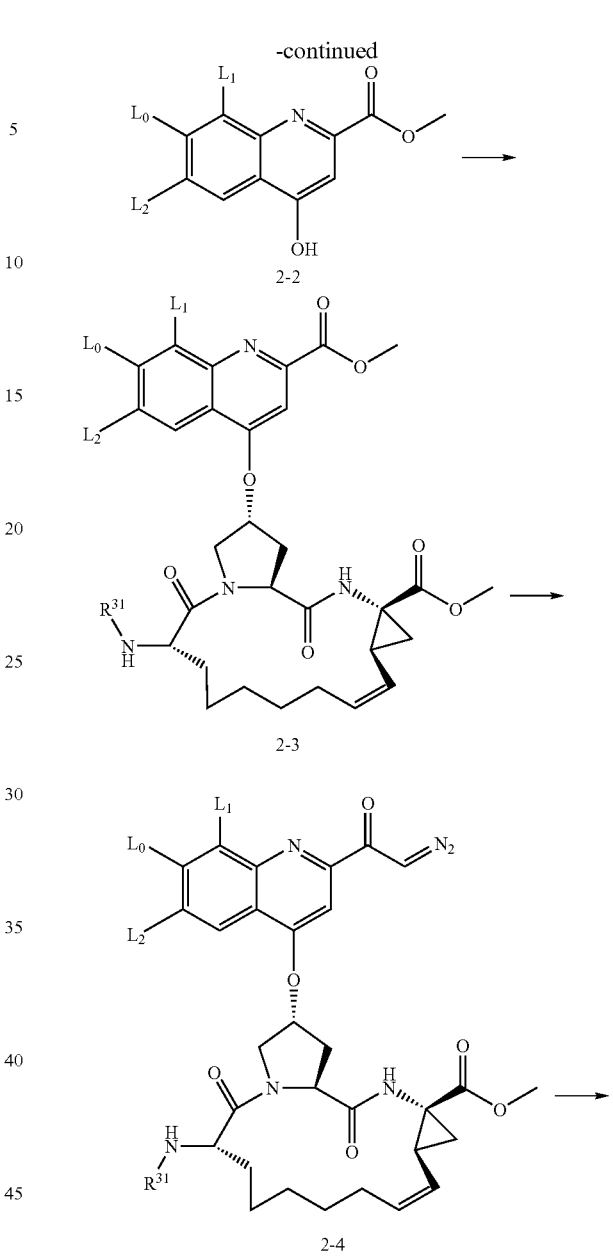

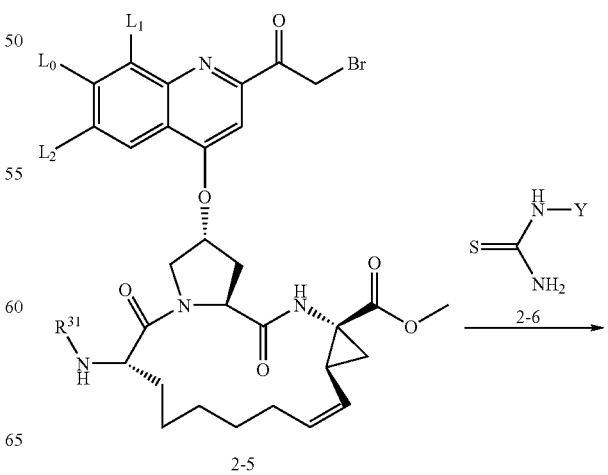

2-5

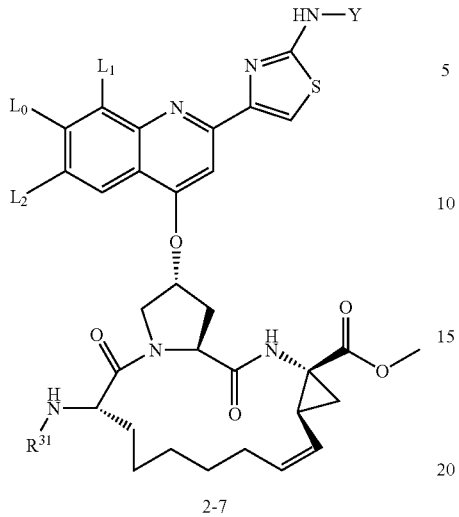

2-7 wherein $L^0$, $L^1$, $L^2$ and $R^{31}$ are as defined herein and Y is selected from —$COR^{20}$, —$COOR^{20}$, $R^{21}$, and —$CONR^{21}R^{22}$, wherein $R^{20}$, $R^{21}$ and $R^{22}$ are as defined herein. Thioureas of formula 2-6 are commercially available or are prepared according to procedures described in International Patent Application WO 03/064416. The methyl ester intermediate 2-7 may be converted to compounds of formula I wherein $R^C$ is hydroxy under standard hydrolysis conditions, preferably basic hydrolysis conditions, well known to one skilled in the art. These compounds of formula I wherein $R^C$ is hydroxy may be further converted to compounds of formula I wherein $R^C$ is —$NHSO_2R^8$ as defined herein as described hereinbefore.

VI. Synthesis of P2 Substituents:

The hydroxyquinolines of formula (Xa or 2-2) used as starting material may be synthesized from commercially available materials using the techniques described in International Patent Applications WO 00/59929, WO 00/09543, WO 00/09558 and U.S. Pat. No. 6,323,180 B1.

In general, synthesis of 2-carbomethoxy-4-hydroxy-quinoline derivatives from the corresponding anilines was carried out according to the procedure of: Unangst, P. C.; Connor, D. T. *J. Heterocyc. Chem.* 29, 5, 1992, 1097-1100. The procedure is shown in scheme 3 below:

SCHEME 3

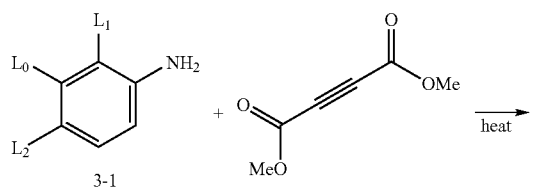

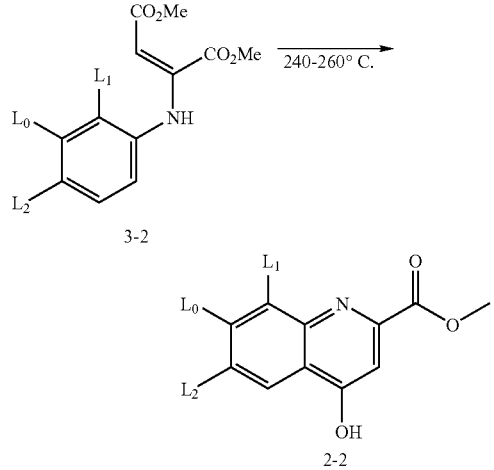

Briefly, appropriately substituted anilines at the 2, 3 and/or 4 position are allowed to react with dimethyl acetylenedicarboxylate and the resulting enamine is heated at high temperatures to effect the cyclization.

The corresponding anilines are commercially available or may require some well known chemical transformations. For example 1 f the nitrobenzene is commercially available, it can be converted to the corresponding aniline by using one of several possible reducing agents well known to those skilled in the art. Also if the carboxylic acid is commercially available, it can be transformed into the corresponding aniline via a Curtius rearrangement.

Further details of the invention are illustrated in the following examples which are understood to be non-limiting with respect to the appended claims. Other specific ways of synthesis or resolution of the compounds of this invention can be found in WO 00/09543; WO 00/09558 & WO 00/59929 and in co-pending application Ser. No. 09/368,670, all of which are hereby incorporated by reference.

EXAMPLES

Temperatures are given in degrees Celsius. Solution percentages express a weight to volume relationship, and solution ratios express a volume to volume relationship, unless stated otherwise. Nuclear magnetic resonance (NMR) spectra were recorded on a Bruker 400 MHz spectrometer; the chemical shifts (δ) are reported in parts per million and are referenced to the internal deuterated solvent unless otherwise indicated. The NMR spectra of all final compounds (inhibitors) was recorded in DMSO-$d_6$. Flash column chromatography was carried out on silica gel ($SiO_2$) according to Still's flash chromatography technique (W. C. Still et al., *J. Org. Chem.*, 1978, 43, 2923).

Abbreviations used in the examples include Boc: tert-butyloxycarbonyl [Me$_3$COC(O)]; BSA: bovine serum albumin; CHAPS: 3-[(3-cholamidopropyl)-dimethylammonio]-1-propanesulfonate; DCHA: dicyclohexylamine; $CH_2Cl_2$=DCM: methylene chloride; DEAD: diethylazodicarboxylate; DIAD: diisopropylazodicarboxylate; DIPEA: diisopropylethylamine; DMAP: dimethylaminopyridine; DMF: N,N-dimethylformamide; DMSO: dimethylsulfoxide; (S,S)-Et-DUPHOS Rh (COD)OTf: (+)-1,2-bis (2S,5S)-2,5-diethylphospholano)benzene(cyctooctadiene)rhodinium(1) trifluoromethanesulfonate; EDC: 1-ethyl-3-[3-(dimethylamino)propyl]carbodiimide; EtOH: ethanol; EtOAc: ethyl acetate; ESMS: electrospray mass spectrometry; HATU: O-(7-azabenzotriazol-1-yl)-1,1,3,3-tetramethyluronium hexafluorophosphate; HPLC: high performance liquid chromatography; MS: mass spectrometry; MALDI-TOF: Matrix Assisted Laser Disorption Ionization-Time of Flight, FAB: Fast Atom Bombardment; mCPBA: meta-chloroperbenzoic acid; MCH: methylcyclohexane; Me: methyl; MeOH: methanol; MIBK: methyl isobutyl ketone; NMP: N-methylpyrrolidone; R.T.: room temperature (18°-22°); SHE: sodium 2-ethylhexanoate; TBTU: 2-(1H-benzotriazole-1-yl)-1,1,3,3-tetramethyluronium tetrafluoroborate; TFA: trifluoroacetic acid; THF: tetrahydrofuran; TLC: thin layer chromatography; Tris/HCl: tris(hydroxymethyl)aminomethane hydrochloride.

Example 1

Synthesis of INRF12 Brosylate Intermediate

Step 1: Introduction of the Boc-protectinq Group: Synthesis of INRF2

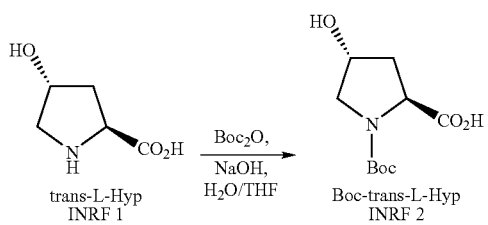

The amino-protection was done with the Boc-protecting group. INRF 1 (trans-4-hydroxy L-proline) (249.8 g, 1.905 mol) was dissolved in water (375 mL) and 45% sodium hydroxide solution (203 g, 2.286 mol). To ensure good phase transfer, tert-butanol (106 g) was added. In a different procedure, acetone was used instead of THF/tert-butanol. The reaction mixture was heated to 50° C. and the anhydride $Boc_2O$ (424 g, 1.943 mol) was dissolved in THF (425 mL, or acetone) is slowly added. The reaction is exothermic and generates gas ($CO_2$) as the $Boc_2O$ was added. If the reaction does not proceed as wanted, catalytic amounts of DMAP (2.3 g, 19 mmol) can be added. After the addition of the $Boc_2O$, the reaction mixture is kept 0.5-1 h at 50° C., and the THF was removed by partial distillation. The pH of the remaining solution was adjusted to about pH3 with concentrated HCl (204 g, 2.076 mol) and the product was then extracted with MIBK (1 liter) and again with MIBK (375 mL). The organic layer was heated and some of the solvent was distilled off to remove traces of water. The product was crystallized from this solution by adding MCH (1.25 L), isolated by filtration, washed twice with MCH (375 mL) and dried overnight at 40° C.

Yield: 77-78%, colorless crystals, $F_p$=126-128° C.

Step 2: Formation of the Lactone; Synthesis of PDIG0016

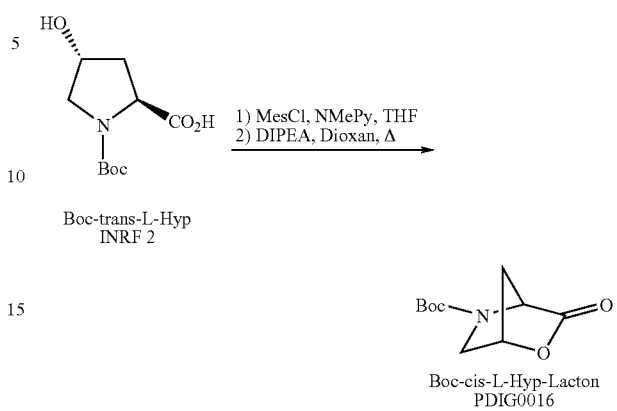

INRF 2 (416.3 g, 1.8 mol) is dissolved in THF (2.08 L) and cooled with ice to a temperature from about −5 to −10° C. Mesylchloride (392 g, 3.4 mol) and N-methylpyrrolidine (429 g, 5 mol) is added and the mixture stirred for about 1½ h at about −5° C. The mixture is washed with water and heated to reflux. Dioxane (2.08 L) is poured in and the THF is distilled off. After cooling down to room temperature, DIPEA (233 g, 1.8 mol) is added and the mixture is heated to reflux. After 1 h part of the solvent (830 mL) is distilled off, cooled to ambient temperature and a $KHSO_4$-solution (14.4 g in 2.08 L water) is poured in and the solution is allowed to cool down to room temperature. The resulting crystals are isolated by filtration, washed with water and dried overnight at 45° C.

Yield: 78-82%, colorless needles, $F_p$=111° C.

Step 3: Deprotection of the Lactone: Synthesis of PDIG0017MS

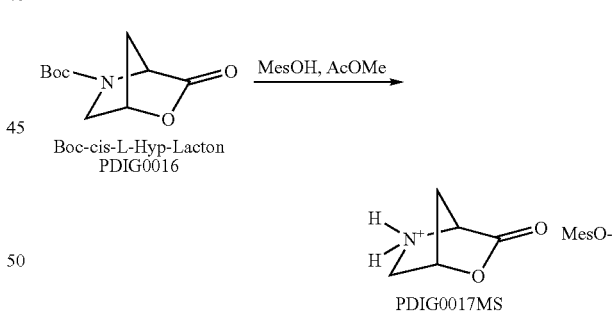

The lactone PDIG0016 (267 g, 1.25 mol) is dissolved in Methyl-isobutylketone (1467 mL). The suspension is heated up to 50° C. until the lactone is completely dissolved and a part of the solvent (130 mL) is distilled off to remove traces of water.

Methanesulfonic acid (240 g, 2.5 mol) is added slowly to the reaction mixture. During the addition gas is evolved ($CO_2$, Isobutene). The reaction mixture is allowed to cool to room temperature and the resulting crystals are isolated by filtration, washed twice with acetone (each 400 mL) and dried overnight at 40° C.

Yield: 93-98%, colorless crystals, 208-210° C.

Step 4: Coupling with INRF 15: Synthesis of the Dipeptide PDIG0027

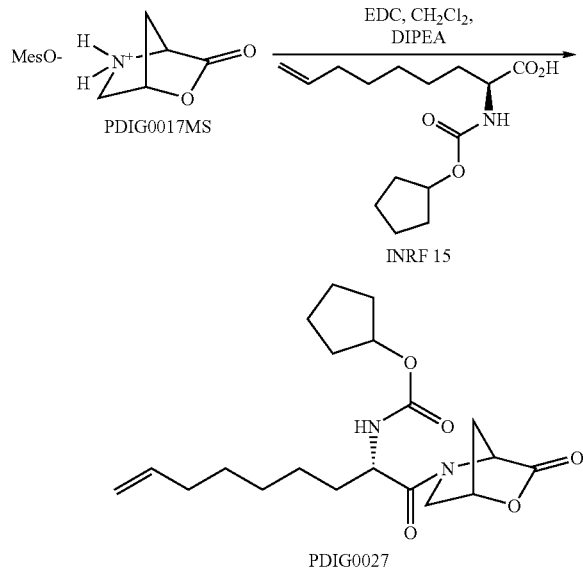

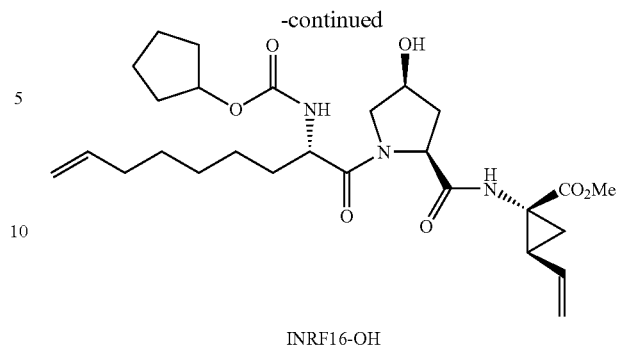

First, INRF15.DCHA has to be released. Therefore, INRF15DCHA (61.4 g, 132 mmol) is dissolved in toluene (160 mL) and the resulting solution is washed with diluted sulfuric acid (5.3 g in 80 mL water) and water (80 mL). After phase separation, the solution is treated with charcoal and filtered and the resulting solution stored at room temperature.

The deprotected lactone PDIG0017MS (24.9 g, 119 mmol) and EDC.HCl (26.8 g, 140 mmol) are suspended in dichloromethane (140 mL) and cooled to room temperature. The suspension is treated with the INRF15-solution generated before. To this suspension, di-isopropylethylamine (Hünigs-Base, 16.3 g, 130 mmol) is slowly added while the reaction is kept under nitrogen at temperatures below 20° C.

The suspension is filtered, and the resulting solution is washed with water (80 mL), diluted acetic acid (1.3 g in 80 mL water), 5% sodium bicarbonate solution (80 mL) and again with water (80 mL). After phase separation, dichloromethane is distilled off under reduced pressure. The resulting solution can directly be used for the next step. Otherwise, the product can be isolated by crystallization from MCH.

Yield: 95% (GC), yellowish solution, $F_p$=58-60° C.

Step 5: Synthesis of INRF 16-OH

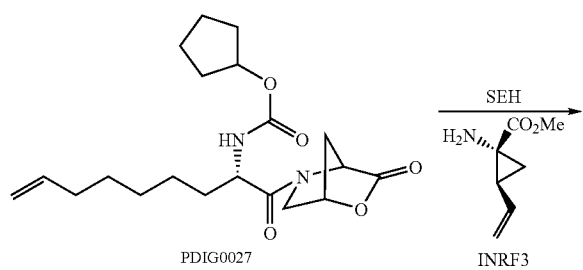

A mixture of PDIG0027 (10.0 g, 23.7 mmol, 1.0 eq.), INRF3 (7.6 g, 24.2 mmol, 1.02 eq.) and sodium 2-ethylhexanoate (SEH) (5.9 g, 35.6 mmol, 1.5 eq.) in water (43 mL) and toluene (12 mL) is stirred at 80° C. for 2 h. For work-up toluene (75 mL) is added at 80° C. After stirring and separation of the aqueous layer, the organic layer is washed with 1M $Na_2CO_3$ (3×30 mL), 0.5M HCl (30 mL) and water (2×30 mL). The solvent is removed under vacuum.

Yield of INRF16-OH: 11.7 g, 22.5 mmol, 95%; purity: >95% (peak-area HPLC) as a slightly yellow oil.

Step 6. Brosylation of INRF16-OH: Synthesis of INRF16-Brs

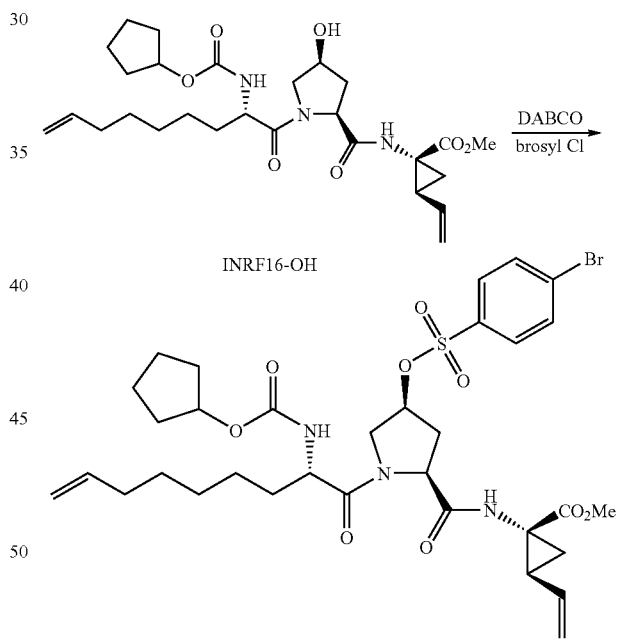

To a mixture of INRF16-OH (10.7 g, 18.5 mmol, 1.0 eq.) and DABCO (3.3 g, 29.7 mmol, 1.6 eq.) and toluene (23 mL) a solution of 4-bromobenzenesulfonyl chloride (brosyl chloride, 6.6 g, 26.0 mmol, 1.4 eq.) in toluene (15 mL) is added slowly at room temperature. The mixture is stirred for 2 h. For work-up the organic layer is washed with 1M $Na_2CO_3$ (2×21 mL), diluted with THF (21 mL) and washed with 0.5M HCl (21 mL) and water (2×21 mL). The solvent is removed under vacuum Yield of INRF16-Brs: 12.3 g, 16.7 mmol, 90%; purity: >95% (peak-area HPLC) as a slightly orange oil. A charcoal treatment of the crude product is possible. .

Step 7: Metathesis of INRF16Brs to INRF12Brs

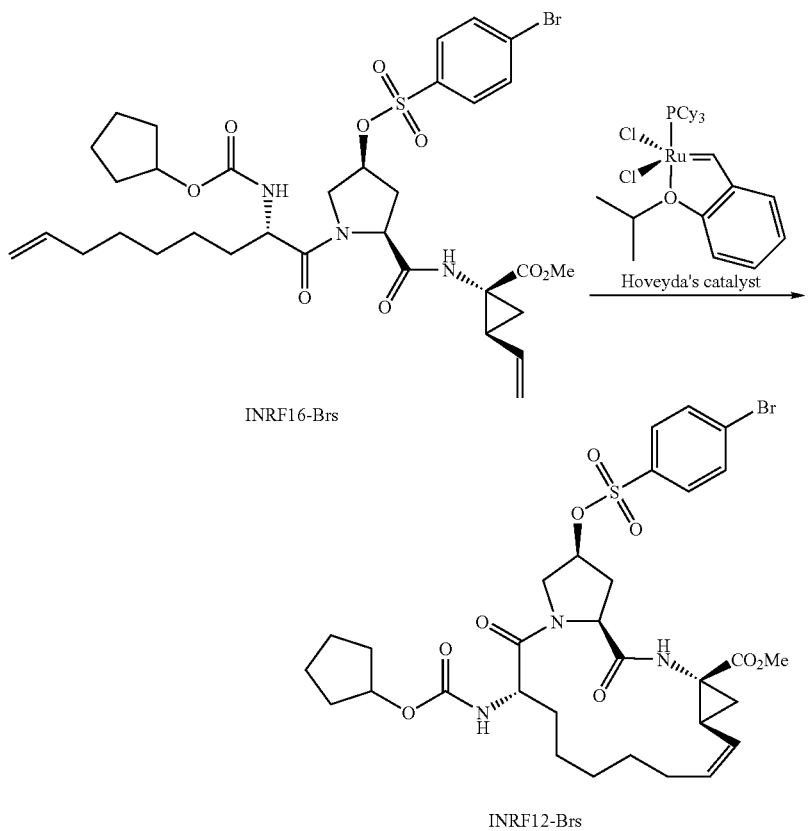

INRF16-Brs

INRF12-Brs

Preparation of the THP-solution (for an experiment with 35.4 g INRF16Brs): 23.5 g Tetrakishydroxymethylphosphoniumchloride (80%, 98.7 mmol) is dissolved in isopropanol (35 mL) under a nitrogen atmosphere. Then 12.1 g (98.7 mmol) of a 45% KOH solution is added within 5 min while the solution is cooled (temperature 20-25° C.). After stirring the suspension for another 30 min under nitrogen, the mixture is filtered and the inorganic residue is washed with 20 mL of degassed isopropanol.

The combined isopropanol solution is stored under a nitrogen atmosphere until use.

Metathesis Reaction:

In a reaction flask 3500 mL of toluene is degassed by bubbling nitrogen through the toluene. 35.2 g (47.7 mmol) of INRF16Brs are dissolved in 70 mL of degassed toluene and added into the reaction flask. The solution is heated up to 80° C. and 3 mol % of Hoveyda's catalyst is added under nitrogen in four portions over a period of 3 hours. After stirring for a further 60 min at the same temperature the conversion is checked by HPLC. In the case that the conversion is below 95%, additional Hoveyda's catalyst is added and the mixture is stirred until the conversion is >95% (during the reaction a slight stream of nitrogen is bubbled through the reaction mixture).

After cooling to 50° C. the THP solution is added to the reaction mixture. After stirring for 8.5 h at 50° C. the mixture is cooled to room temperature and extracted twice with 188 mL of degassed water, 188 mL of 0.5 M HCl, 188 mL of 0.5 M NaHCO$_3$ solution, and 188 mL of water.

Approximately 2800 mL of toluene are distilled off at 50° C. under partial reduced pressure and the remaining solution is treated at 50° C. with 6.8 g of charcoal (Acticarbon L$^2$S). The charcoal is then removed by filtration.

The remaining liquid filtrate (approx. 130 mL) is added over a period of 1 hour to 1.5 liters of pre-cooled MCH (5° C.). After stirring for a further 30 min at 5° C. the precipitate is filtered and washed with 100 mL of MCH (several portions). The white solid is dried in vacuo at 25° C.

Yield (by weight): 38 g of an almost white powder.

Example 2A

Synthesis of 2-carbomethoxy-4-hydroxy-7-methoxy8-methylquinoline (A5)

Step A

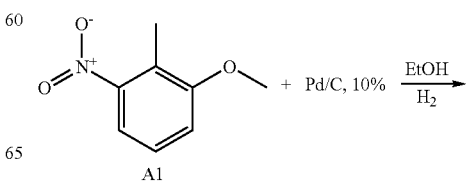

A1

-continued

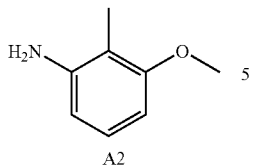

To a solution of 2-methyl-3-nitro anisole A1 (5.1 g; 30.33 mmol; requires ~30 min to dissolve) in absolute ethanol (85 mL) was added 10% Pd/C catalyst (500 mg). The solution was hydrogenated under a hydrogen filled balloon at atmospheric pressure and room temperature for 19 h. The reaction mixture was filtered through a Celite pad, rinsed and evaporated to dryness to obtain 2-methyl-3-methoxyaniline A2 as a deep mauve oil (4.1 g; 29.81 mmol; 98% yield).

MS 137 (MH)$^+$. Reverse Phase HPLC Homogeneity @ 220 nm (0.06% TFA; CH$_3$CN:H$_2$O): 99%.

Step B

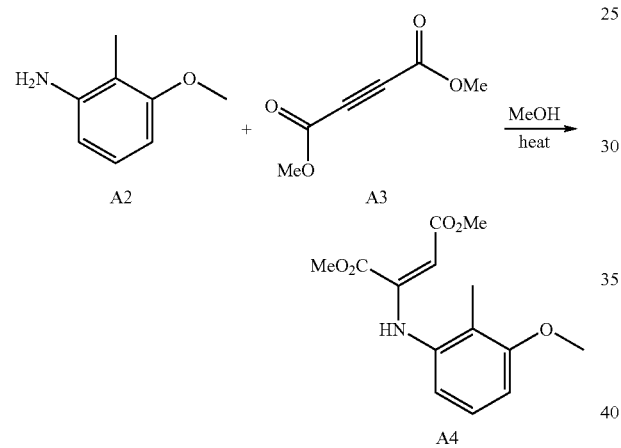

Dimethyl acetylene dicarboxylate A3 (3.6 mL, 29.28 mmol) was added dropwise to a solution of 2-methyl-3-methoxyaniline A2 (3.95 g, 28.79 mmol) in MeOH (100 mL) (reaction is exothermic). The mixture was heated at a gentle reflux for 5 hours cooled and concentrated under vacuum. The crude material was purified by flash column chromatography on silica gel with hexane:EtOAc (95:5) to provide, after evaporation of the pure fractions, the product A4 (6.5 g; 23.27 mmol; 81% yield). Reverse Phase HPLC Homogeneity @ 220 nm (0.06% TFA; CH$_3$CN:H$_2$O): 95%.

Step C

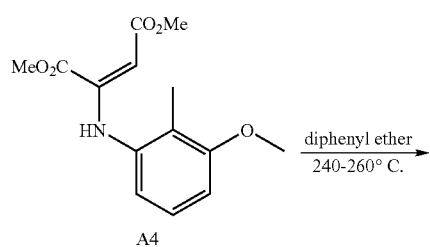

-continued

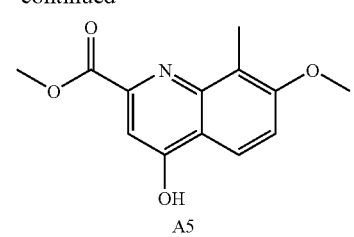

The diester A4 (6.5 g, 23.27 mmol) was dissolved in diphenyl ether (12 mL) and the reaction mixture placed into a pre-heated sand bath at a bath temperature of 350-400° C. Once the reaction mixture attained an internal temperature of 240° C. (observe MeOH evolution at 230-240° C.) a count of six minutes was begun before the bath (temperature end point: 262° C.) was removed and the reaction allowed to cool to room temperature. A solid formed upon cooling which was diluted with ether, filtered and dried to give a tan brown solid (3.48 g crude). The crude material was chromatographed on silica gel column with hexane:EtOAc; 5:5 to remove impurities, then 2:8 and then 100% EtOAc to complete the elution of the product to provide A5, after evaporation, as a pale yellow solid (2.1 g, 37% yield).

MS (M+H)$^+$; 248.1, and (M−H)$^−$; 246. Reverse Phase HPLC Homogeneity @ 220 nm (0.06% TFA; CH$_3$CN:H$_2$O): 99%.

Example 2B

Synthesis of 2-carbomethoxy-8-bromo-4-hydroxy-7-methoxyquinoline (B6)

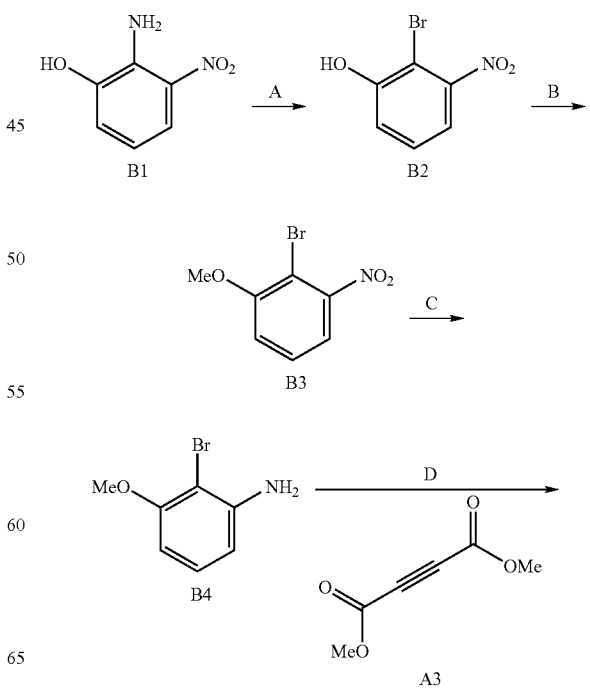

-continued

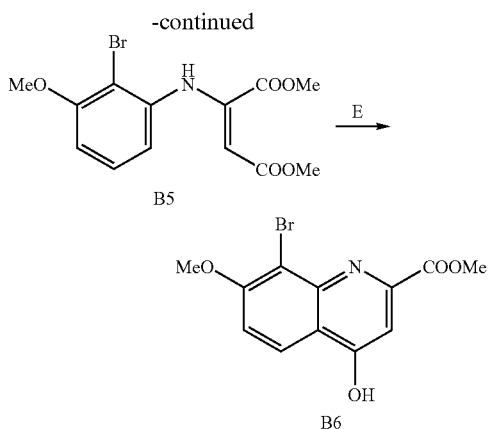

Step A

2-Amino-3-nitrophenol B1 (5 g; 32.4 mmol) was dissolved in H$_2$O (29.5 mL) and 1,4-dioxane (14.7 mL). The mixture was heated to reflux and hydrobromic acid (48%; 16.7 mL; 147 mmol) was added dropwise over a period of 20 min. Upon completion of the addition, the reflux was maintained an additional 15 min. The reaction was cooled to 0° C. (ice bath), and sodium nitrite (2.23 g; 32.3 mmol) in H$_2$O (20 mL) was added over a period of 30 min. The stirring was continued for 15 min at 0° C., then the mixture was transferred to a jacketed dropping funnel (0° C.) and added dropwise to a stirred mixture of Cu(I)Br (5.34 g; 37.2 mmol) in H$_2$O (29.5 mL) and HBr (48%; 16.7 mL; 147 mmol) at 0° C. The reaction was stirred for 15 min at 0° C., warmed to 60° C., stirred for an additional 15 min, cooled to room temperature, and left to stir overnight. The reaction mixture was transferred to a separatory funnel and extracted with ether (3×150 mL). The organic layers were combined, washed with brine (1×), dried (Na$_2$SO$_4$), filtered and concentrated to afford the crude product (7.99 g) as a red-brown oil. The crude material was purified by flash column chromatography (1:25 ultra pure silica gel, 230-400 mesh, 40-60 mm, 60 angstroms; CH$_2$Cl$_2$ as the solvent) to afford pure 2-bromo-3-nitrophenol B2 (45%; 3.16 g) as an orange-brown solid.

MS 217.8 (MH)$^-$. Homogeneity by HPLC (TFA) @ 220 nm: 97%.

Step B

The nitrophenol starting material B2 (3.1 g; 14.2 mmol) was dissolved in DMF (20 mL) and to the solution was added ground cesium carbonate (5.58 g; 17.1 mmol) followed by MeI (2.6 mL; 42.5 mmol). The mixture was stirred at room temperature overnight. The DMF was evaporated, the residue taken up in ether (1×200 mL), washed with water (1×200 mL), brine (4×100 mL), dried (MgSO$_4$), filtered and evaporated to afford the crude 2-bromo-3-nitroanisole B3 (94%; 3.1 g) as an orange solid.

MS 234 (M+2H)$^+$; Homogeneity by HPLC (TFA) @ 220 nm: 98%.

Step C

2-Bromo-3-nitroanisole B3 (1.00 g; 4.31 mmol) was dissolved in glacial acetic acid (11.0 mL) and ethanol (11.0 mL). To this solution was added iron powder (0.98 g; 17.5 mmol). The mixture was stirred at reflux for 3.5 h and worked up. The reaction mixture was diluted with water (35 mL), neutralized with solid Na$_2$CO$_3$ and the product extracted with CH$_2$Cl$_2$ (3×50 mL). The extracts were dried (Na$_2$SO$_4$), filtered and concentrated in vacuo to afford the crude product, 2-bromo-3-methoxyaniline B4 (91%; 0.79 g) as a pale yellow oil.

MS 201.8 (MH)$^+$; Homogeneity by HPLC (TFA) @ 220 nm: 95%.

Step D

To a solution of 2-bromo-3-methoxyaniline B4 (0.79 g; 3.9 mmol) in MeOH (7.6 mL) was added dimethyl acetylene dicarboxylate A3 (0.53 mL; 4.3 mmol) dropwise at 0° C. (caution: reaction is exothermic!). The solution was heated overnight at reflux and worked-up. The MeOH was evaporated and the crude product dried under high vacuum to afford a red gum, purified by flash column chromatography (1:30 ultra pure silica gel, 230-400 mesh, 40-60 mm, 60 angstroms; 4:1 hexane/EtOAc) to afford adduct B5 (86%; 1.16 g) as a pale yellow solid.

MS 344.0 (MH)$^+$; Homogeneity by HPLC (TFA) @ 220 nm: 72%.

Step E

To a pre-heated sand bath at about 440° C. (external temperature) was placed the diester adduct B5 (1.1 g; 3.16 mmol) in diphenyl ether (3.6 mL). The reaction was stirred between 230° C.-245° C. (internal temperature; MeOH started evaporating off at about 215° C.) for 7 min and subsequently cooled to room temperature. As the solution cooled the product crystallized from the reaction mixture. The resulting brown solid was filtered, washed with ether and dried under high vacuum to afford the crude bromoquinoline B6 product (74%; 0.74 g) as a brown solid. NMR revealed this product to be a mixture of about 1:1 tautomers.

NMR (DMSO; 400 MHz) ok (1:1 mixture of tautomers); MS 311.9 (MH)$^+$; Homogeneity by HPLC (TFA) @ 220 nm: 96%.

Example 2C

Synthesis of 2-carbomethoxy-8-chloro-4-hydroxy-7-methoxyquinoline (C6)

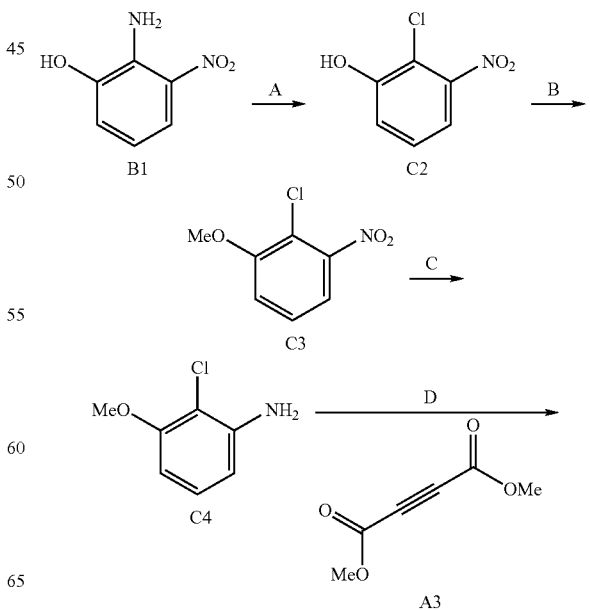

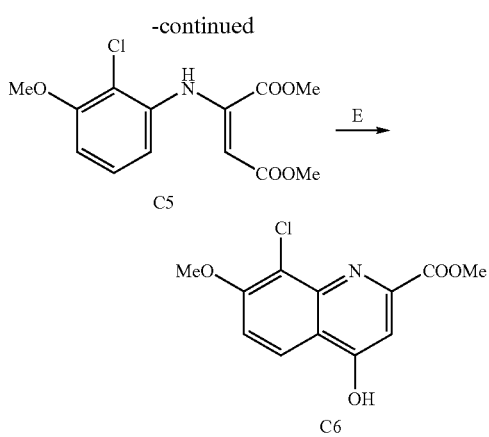

Step A

2-Amino-3-nitrophenol B1 (5 g; 32.4 mmol) was dissolved in concentrated HCl (75 mL) and 1,4-dioxane (14.7 mL). The mixture was heated to 70° C. until most of the solids were in solution. The reaction mixture was cooled to 0° C. (ice bath), and sodium nitrite (2.23 g; 32.3 mmol) in H$_2$O (5.4 mL) was added over a period of 3 hours to the brown solution. The temperature was maintained below 10° C. during the addition and the stirring was continued for an additional 15 min at 0° C. This diazonium intermediate was poured into a solution of Cu(I)Cl (3.8 g; 38.9 mmol) in H$_2$O (18.5 mL) and conc. HCl (18.5 mL) at 0° C. The reaction was stirred for 15 min at 0° C., warmed to 60° C., and stirred for an additional 15 min The reaction mixture was then brought to room temperature, and left to stir overnight. The reaction mixture was transferred to a separatory funnel and extracted with ether (3×150 mL). The organic layers were combined, washed with brine (1×), dried (Na$_2$SO$_4$), filtered and concentrated to afford the crude product (5.83 g) as a red-brown oil. The crude material was purified by flash column chromatography (1:25 ultra pure silica gel, 230-400 mesh, 40-60 mm, 60 angstroms; 3:1 hexane/EtOAc as the solvent) to afford pure 2-chloro-3-nitrophenol C2 (48%; 2.7 g) as an orange solid.

MS 171.8 (MH)⁻: Homogeneity by HPLC (TFA) @ 220 nm: 96%.

Relevant literature for the Sandmeyer Reaction: *J. Med. Chem*, 1982, 25(4), 446-451.

Step B

The nitrophenol starting material C2 (1.3 g; 7.49 mmol) was dissolved in DMF (10 mL) and to this solution was added ground cesium carbonate (2.92 g; 8.96 mmol), followed by MeI (1.4 mL; 22.5 mmol). The mixture was stirred at room temperature overnight. The DMF was evaporated in vacuo and the residue taken up in ether (150 mL), washed with water (150 mL), brine (4×100 mL), and then dried over (MgSO$_4$). The organic phase was filtered and evaporated to afford the crude 2-chloro-3-nitroanisole C3 (98%; 1.38 g) as an orange solid.

Homogeneity by HPLC (TFA) @ 220 nm: 93%.

Step C

2-Chloro-3-nitroanisole C3 (1.38 g; 7.36 mmol) was dissolved in a mixture of glacial acetic acid (19 mL)/ethanol (19 mL). To this solution was added iron powder (1.64 g; 29.4 mmol). The mixture was stirred at reflux for 3.5 hr and worked up. The reaction mixture was diluted with water (70 mL), neutralized with solid Na$_2$CO$_3$ and the product extracted with CH$_2$Cl$_2$ (3×150 mL). The extracts were combined and washed with saturated. brine and then dried over (Na$_2$SO$_4$), filtered and concentrated in vacuo to afford the crude product, 2-chloro-3-methoxyaniline C4 (100%; 1.2 g) as a yellow oil. This material was used as such in the following steps.

MS 157.9 (MH)⁺; Homogeneity by HPLC (TFA) @ 220 nm: 86%.

Step D

To a solution of 2-chloro-3-methoxyaniline C4 (1.2 g; 7.61 mmol) in MeOH (15 mL) was added dimethyl acetylene dicarboxylate A3 (1.0 mL; 8.4 mmol) dropwise at 0° C. (caution: reaction is exothermic!). The solution was heated overnight at reflux and worked-up. The MeOH was evaporated and the crude product dried under high vacuum to afford a red gum which was purified by flash column chromatography (1:30 ultra pure silica gel, 230-400 mesh, 40-60 mm, 60 angstroms; 4:1 hexane/EtOAc) to afford adduct C5 (74%; 1.68 g) as a yellow solid.

MS 300 (MH)⁺; Homogeneity by HPLC (TFA) @ 220 nm: 90%.

Step E

To a pre-heated sand bath at about 440° C. (external temperature) was placed the diester adduct C5 (1.68 g; 5.6 mmol) in diphenyl ether (6.3 mL). The reaction was stirred between 230° C.-245° C. (internal temperature; MeOH started evaporating off at about 215° C.) for 7 min and subsequently cooled to room temperature. As the solution cooled the product crystallized from the reaction mixture. The resulting brownish solid was filtered, washed with ether and dried under high vacuum to afford the quinoline C6 (83%; 1.25 g) as a beige solid. NMR revealed this product to be a mixture of about 1:1 tautomers (keto/phenol forms).

MS 267.9 (MH)⁺; Homogeneity by HPLC (TFA) @ 220 nm: 92%.

Example 2D

Synthesis of 2-carbomethoxy-4-fluoro-4-hydroxy-7-methoxyquinoline (D5)

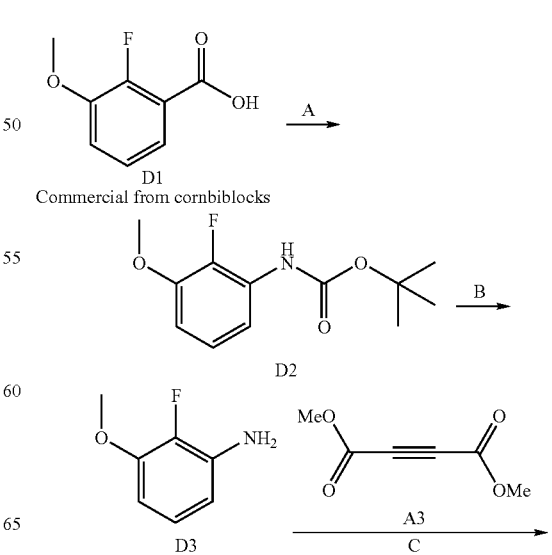

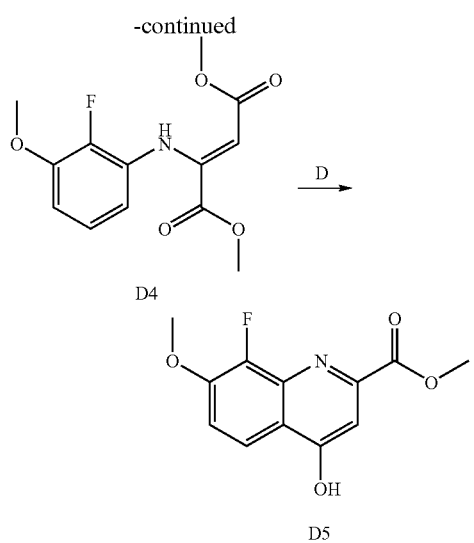

Step A

A solution of 2-fluoro-3-methoxy benzoic acid D1 (1.68 g, 9.87 mmol) and DIPEA (2.07 mL, 11.85 mmol, 1.2 equiv.) in a mixture of toluene (8 mL) and t-BuOH (8 mL) were stirred over activated 4 A molecular sieves for 1 h followed by addition of diphenyl phosphoryl azide (DPPA, 2.55 mL, 11.85 mmol) and this mixture was refluxed overnight. Reaction mixture was filtered and the filtrate was concentrated in vacuo, the residue was taken in EtOAc (50 mL), washed with $H_2O$ (2×30 mL) and brine (1×30 mL). The organic phase was dried ($MgSO_4$), filtered and concentrated under reduced pressure. The crude product D2 (2.38 g, 96%) was used as is in the following step. MS analysis shows the loss of Boc group: 141.9 ((M+H)-Boc)$^+$, 139.9 ((M-H)-Boc)$^-$.

Step B

Compound D2 (2.28 g, 9.45 mmol) was treated with 4N HCl/dioxane solution (from Aldrich) (10 mL, 40 mmol) for 60 min and HPLC analysis showed that the starting material was fully consumed. The reaction mixture was concentrated in vacuo, re-dissolved in EtOAc and washed with water, saturated $NaHCO_3$ (aq), and saturated brine. The organic phase was dried ($MgSO_4$), filtered and concentrated to give 1.18 g (88%) of D3 as a brown oil, which was used as is in the following step. MS: 141.9 (M+H)$^+$, 139.9 (M-H)$^-$.

Step C

Aniline D3 (1.18 g, 8.36 mmol) was combined with dimethylacetylene dicarboxylate A3 (1.45 mL, 10.0 mmol) in methanol (25 mL). The reaction was refluxed for 2 hours before being concentrated to dryness. The crude material was purified by flash chromatography eluting with 9/1 (hexane/EtOAc) to give the Michael adduct D4 as a yellow oil, (1.27 g, 54%).

Step D

The Michael adduct D4 was dissolved in warm diphenyl ether (6 mL) and placed in a sand bath previously heated to 350° C. The internal temperature of the reaction was monitored and maintained at ~245° C. for about 5 minutes (solution turns brown).

After cooling to R.T., the desired 4-hydroxyquinoline crashed out of solution. The brown solid was filtered and washed several times with diethyl ether to give, after drying, quinoline D5 as a brown solid (0.51 g, 45%). MS: 252 (M+H)$^+$, 249.9 (M-H)$^-$. Mixture of 1:1 tautomers, $^1$H-NMR (DMSO-$d_6$, 400 MHz) 12.04 (s, 1H), 11.02 (s, 1H), 8.0 (d, 1H), 7.88 (d, 1H), 7.65 (m, 1H), 7.39 (s, 1H), 7.32 (m, 1H), 6.5 (s, 1H), 4.0 (s, 3H), 3.98 (s, 3H), 3.95 (s, 3H), 3.91 (s, 3H).

Example 2E

Synthesis of 2-carbomethoxy-6,8-dimethyl-4-hydroxy-7-methoxyquinoline (E8)

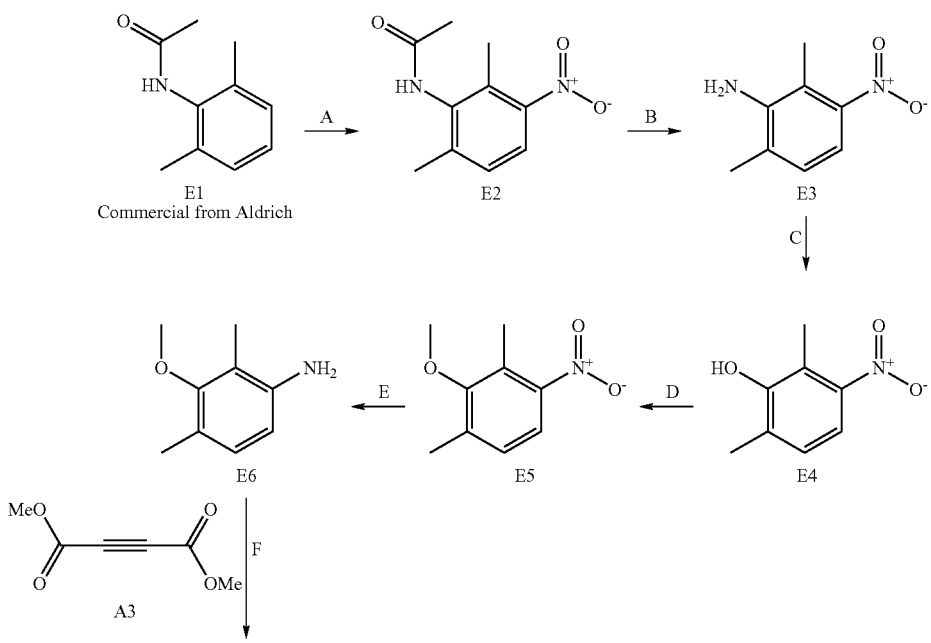

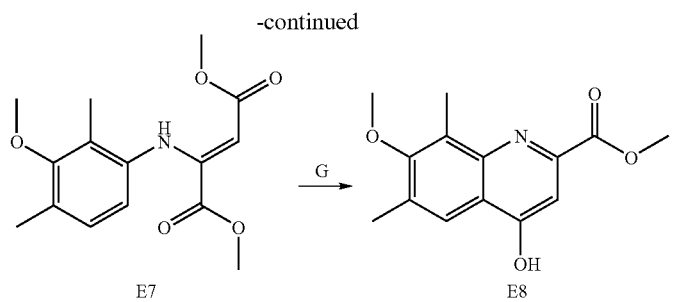

Step A

The amide E1 (5.0 g, 30.63 mmol) was dissolved in a mixture of acetic acid (5 mL) and sulfuric acid (10 mL) and cooled to 0° C. A mixture of nitric acid (70%, 3 mL) and sulfuric acid (2 mL) was added dropwise after which the solution was warmed to R.T. and stirred for 1 h. The reaction mixture was then poured onto crushed ice and filtered (after the ice had melted but the solution was still cold) to yield the desired compound E2 (5.8 g, 91%) which was carried forward to the next reaction without further purification. MS ES$^+$=209.0, ES$^-$=206.9. (Ref: Giumanini, A. G.; Verardo, G.; Polana, M. J. Prak. Chem. 1988, 181).

Step B

Compound E2 (5.8 g, 27.86 mmol) was treated with 6M HCl solution (5 mL) in MeOH (10 mL) and heated at reflux for 48 h to yield the desired product E3 (4.6 g, 99%). RP-HPLC indicates full consumption of starting material (R$_t$ (E2)=2.6 min.; R$_t$(E3)=3.9 min.). The mixture was concentrated and employed in subsequent reaction without further purification.

Step C

Sulfuric acid (18 mL) was added to the solution of aniline E3 (4.20 g, 25.27 mmol) in water (36 mL) at 0° C. followed by the addition of sodium nitrite (2.3 g, 33.33 mmol in water (6 mL). In a separate flask was placed a mixture of water (14 mL) and sulfuric acid (1.5 mL). This solution was brought to reflux and then the initial solution was added dropwise while maintaining a boil. After the addition was complete, boiling was continued for 5 min and the mixture then poured onto ice/sodium carbonate mixture while cooling in an ice bath. The product was extracted with aq. EtOAc and concentrated to yield a dark brown viscous liquid E4 (2.00 g, 47%) which was employed in subsequent reaction without further purification. MS ES$^-$=210.9.

Step D

MeI (1.42 mL, 22.74 mmol) was added to a solution of the starting phenol E4 (1.9 g, 11.37 mmol) and potassium carbonate (2 g) in DMF (25 mL) at R.T. The mixture was heated at 50° C. for 2 h and then cooled to R.T. EtOAc was added and the solution was washed with water (3×) and the aq. layer was then extracted with EtOAc. The combined organic layers were dried, filtered and concentrated to yield the desired methyl ether E5 (2.0 g, 97%). $^1$H-NMR (CDCl$_3$, 400 MHz) 7.62 (d, J=8.4 Hz, 1H), 7.13 (d, J=8.4 Hz, 1H), 3.74 (s, 3H), 2.48 (s, 3H), 2.36 (s, 3H).

Step E

Ten percent (10%) Pd/C (200 mg) was added to a solution of nitro starting material E5 (2.0 g, 11.04 mmol) in EtOH and placed on a Parr shaker under 40 psi H$_2$ atmosphere for 2 h. The solution was filtered through a pad of silica/Celite, rinsed with MeOH and concentrated to yield the desired aniline E6 (1.5 g, 90%) which was employed without further purification.

Step F

Aniline E6 (1.9 g, 12.65 mmol) was combined with dimethylacetylene dicarboxylate A3 (2.32 mL, 18.85 mmol) in methanol (3 mL). The reaction was heated at reflux for 2 h before being concentrated to dryness. The crude material was purified by flash chromatography (9:1 hexane/EtOAc) to give the Michael adduct E7 as a yellow oil (2.8 g, 76%). $^1$H-NMR (CDCl$_3$, 400 MHz) 9.48, (s, br, 1H), 6.89 (d, J=7.9 Hz, 1H), 6.47 (d, J=7.9 Hz, 1H), 5.35 (s, 1H), 3.74 (s, 3H), 3.70 (s, 3H), 3.65 (s, 3H), 2.27 (s, 3H), 2.24 (s, 3H).

Step G

The Michael adduct E7 was dissolved in warm diphenyl ether (10 mL) and placed in a sand bath previously heated to −350° C. The internal temperature of the reaction was monitored, maintained at −245° C. for about 5 minutes (solution turns brown) and cooled to R.T. at which time the desired 4-hydroxyquinoline precipitated out of solution. The brown solid was filtered and washed several times with diethyl ether to give quinoline E8 as a yellow-brown solid after drying (1.10 g, 88%). $^1$H-NMR (CDCl$_3$, 400 MHz) 8.80 (s, br, 1H), 8.06 (s, 1H), 7.26 (s, 1H), 6.93 (s, 1H), 4.04 (s, 3H), 3.80 (s, 3H), 2.45 (s, 3H), 2.39 (s, 3H).

Example 2F

Synthesis of 2-carbomethoxy-4-hydroxy-8-methylthioquinoline (F3)

Step A

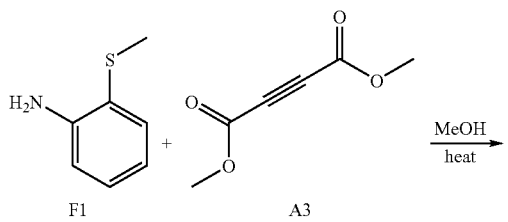

-continued

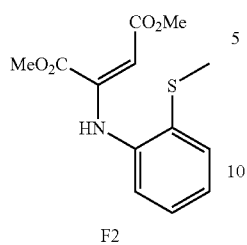

F2

Dimethyl acetylene dicarboxylate A3 (5.21 mL, 35.91 mmol) was added dropwise to a solution of 2-methylmercaptoaniline F1 (5.0 g, 35.91 mmol) in MeOH (100 mL).

Caution the reaction is exothermic. The mixture was heated at a gentle reflux for 2 hours, cooled and concentrated under vacuum. The crude material was purified by flash column chromatography with hexane:EtOAc (90:10) to provide, after evaporation of the pure fractions, the diester adduct F2 (10.53 g; 37.43 mmol; 99% yield).

Homogeneity by HPLC (TFA) @ 220 nm: 85%.

Step B

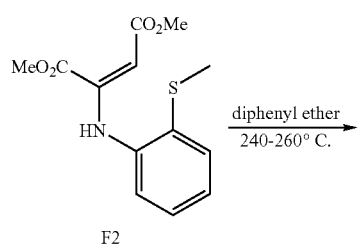

The diester F2 (10.53 g, 37.43 mmol) was dissolved in diphenyl ether (35 mL) and the reaction mixture placed into a pre-heated sand bath at a bath temperature of 350-400° C. Once the reaction mixture attained an internal temperature of 245° C., a count of six minutes was begun before the bath was removed and the reaction allowed to cool to room temperature. A precipitate formed. which was suspended in ether, filtered and washed again with ether to provide the C8-SMe quinoline product F3 (6.15 g; 66%). MS (M+H)⁺; 250 Homogeneity by HPLC (TFA) @ 220 nm: 99%.

Example 2G

Synthesis of 2-carbomethoxy-4-hydroxy-8-methanesulfonylquinoline (G1)

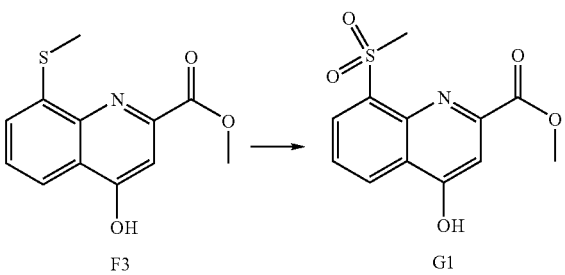

To the 8-thiomethylquinoline F3 (1 g, 4 mmol) in $CH_2Cl_2$ (30 mL) at RT was added mCPBA (1.73 g, 10 mmol). The reaction mixture was stirred at RT for 4 hours, then concentrated and the residue was dissolved in EtOAc (50 mL). The organic phase was washed with $H_2O$ and brine; dried ($MgSO_4$), filtered and concentrated under reduced pressure. A yellow solid was obtained which was triturated with THF and filtered to give 375 mg (yield 33%) of G1 as a yellow solid.

Example 2H

Synthesis of 2-carbomethoxy-4-hydroxy-8-(2-trimethylsilylethynyl)quinoline (H3)

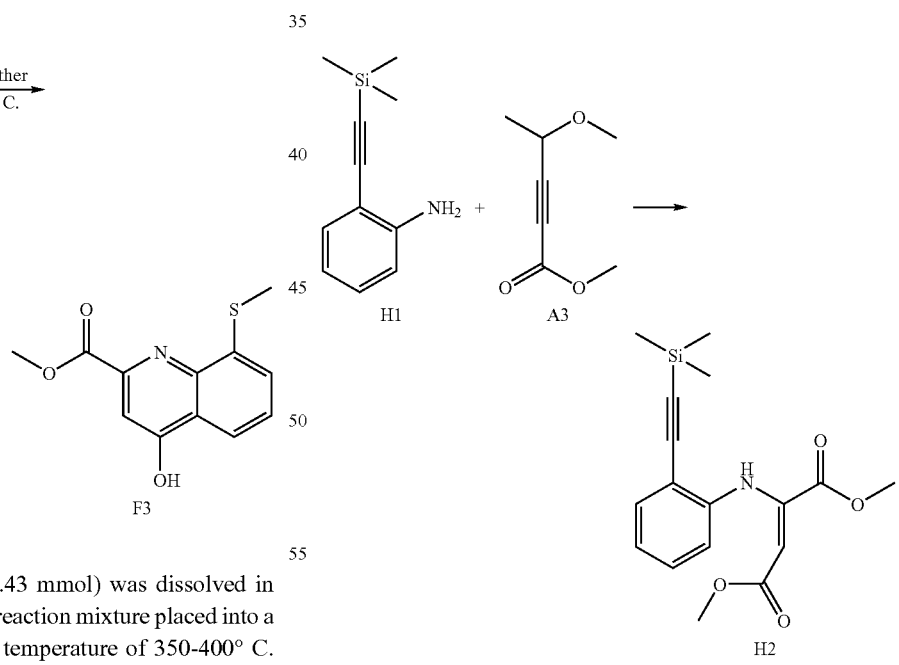

Step A

The commercially available aniline H1 (1.37 g, 6.80 mmol) was dissolved in MeOH (25 mL) and the alkyne A3 (0.84 mL, 6.80 mmol) was added and the mixture was heated to 70° C. for 14 h. The mixture was cooled to RT, the solvent was removed and the resulting oil was purified by flash column chromatography (9:1 to 1:1 hex:EtOAc) to yield the desired product H2 (2.1 g, 93%). MS ES+=332.1, ES−=330.1.

Example 3A

Synthesis of Bromoketone 3d

Step A

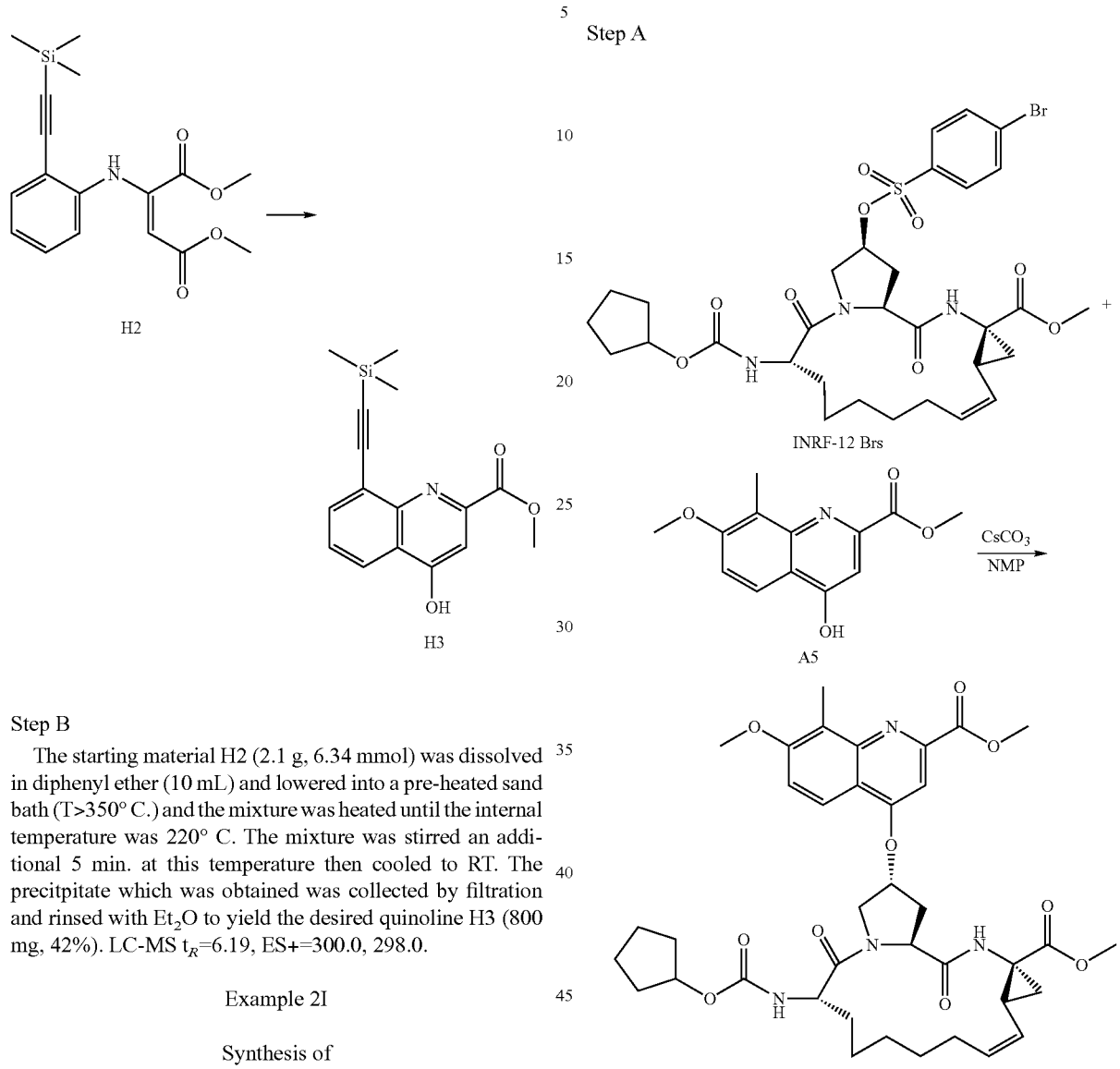

Step B

The starting material H2 (2.1 g, 6.34 mmol) was dissolved in diphenyl ether (10 mL) and lowered into a pre-heated sand bath (T>350° C.) and the mixture was heated until the internal temperature was 220° C. The mixture was stirred an additional 5 min. at this temperature then cooled to RT. The precitpitate which was obtained was collected by filtration and rinsed with $Et_2O$ to yield the desired quinoline H3 (800 mg, 42%). LC-MS $t_R$=6.19, ES+=300.0, 298.0.

Example 2I

Synthesis of 2-carbomethoxy-4-hydroxy-8-methylquinoline (I1)

Employing the same sequence as employed in the preparation of quinoline F3 but starting with the commercially available o-toluidene (Aldrich Chemical Co.) rather than 2-methylmercaptoaniline (F1) the desired quinoline I1 was obtained (1.24 g, 59% yield over two steps).

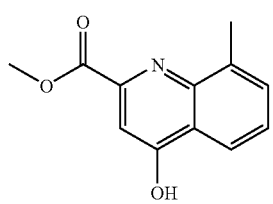

To a solution of the brosylate INRF-12 Brs (2.11 g; 2.97 mmoles) and quinoline A5 (881 mg; 3.56 mmoles) in 1-methyl-2-pyrrolidinone (15 mL) was added ground cesium carbonate (1.45 mg; 4.45 mmoles). The resulting suspension was stirred for 6 hours in a preheated 40° C. oil bath, then, at room temperature overnight. The reaction mixture was diluted with EtOAc, washed extensively with $H_2O$ (3×), $NaHCO_3$ (sat'd; 2×), water (2×) and brine (2×), dried ($MgSO_4$), filtered and concentrated to afford the crude product (2.15 g) as an off white solid. Purification by chromatography on silica gel column with hexane:EtOAc (5:5 to 4:6) provided the pure product 3a as an off-white solid (1.9 g; 89%)

MS 719.3 (M−H)− 721.4 (M+H)+. Reverse Phase HPLC Homogeneity @ 220 nm (0.06% TFA; $CH_3CN:H_2O$): 96%

Step B

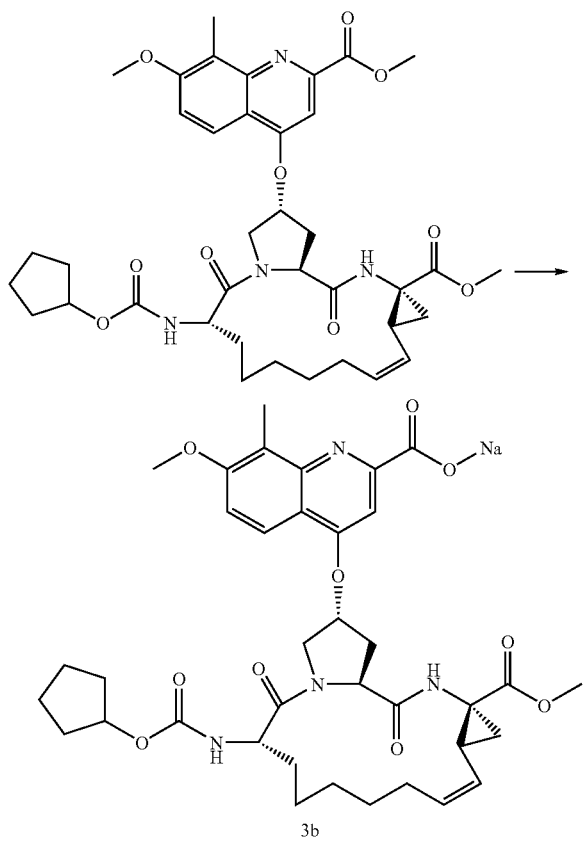

To the methyl ester 3a (1.9 g; 2.64 mmol) dissolved in THF (12 mL), MeOH (6 mL) and water (6 mL) was added 1N NaOH (1.05 equivalents; 2.77 mL). The yellow solution was stirred at room temperature for 2.5 hours (no visible starting material by HPLC). The mixture was evaporated to near dryness, diluted with water, frozen and lyophilized to provide the sodium salt 3b as a white amorphous solid (2.04 g; quantitative). Reverse Phase HPLC Homogeneity @ 220 nm (0.06% TFA; $CH_3CN:H_2O$): 86%.

Step C

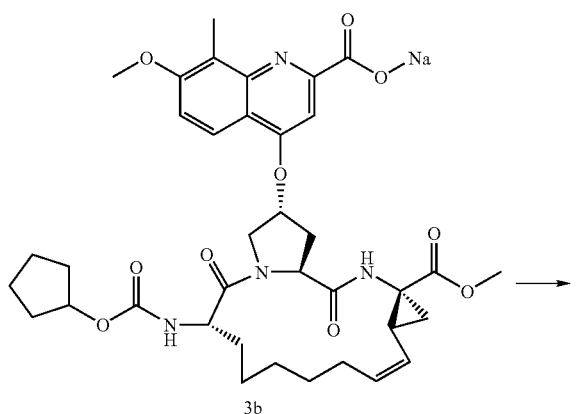

-continued

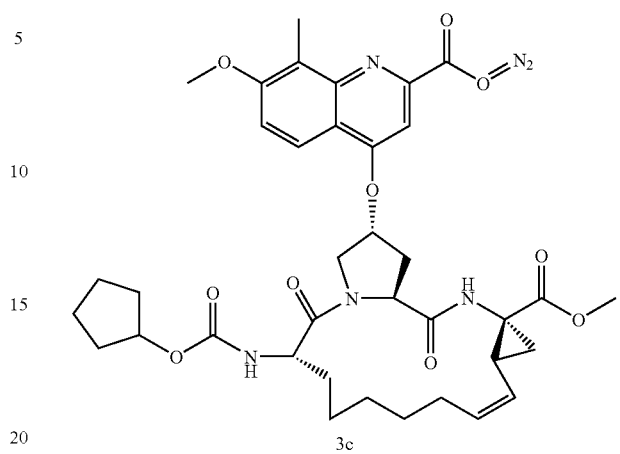

To a cooled (0° C.) solution of the crude mono-acid Na salt 3b (assume 2.64 mmol) in THF (35 mL), and triethylamine (514 µL; 3.69 mmol) was added dropwise isobutylchloroformate (479 µL; 3.69 mmol). The white suspension was stirred at 0° C. for 2 hours, then, diazomethane (0.67M in ether; 23.6 mL; 15.82 mmol) was added. The reaction mixture was stirred 1 hour at 0° C. and 1.5 hours at room temperature after which it was evaporated to near dryness to provide a thick suspension. This suspension was dissolved by dilution with EtOAc and water and washed with saturated $NaHCO_3$ (2×), water (2×) and brine (1×), dried ($MgSO_4$), filtered and evaporated to provide the diazoketone product 3c as an ivory solid (crude material used for next step; assume 2.64 mmol).

M.S. (electrospray) 729.3 (M−H)⁻ 731.4 (M+H)⁺. Reverse Phase HPLC Homogeneity @ 220 nm (0.06% TFA; $CH_3CN:H_2O$): 87%.

Step D

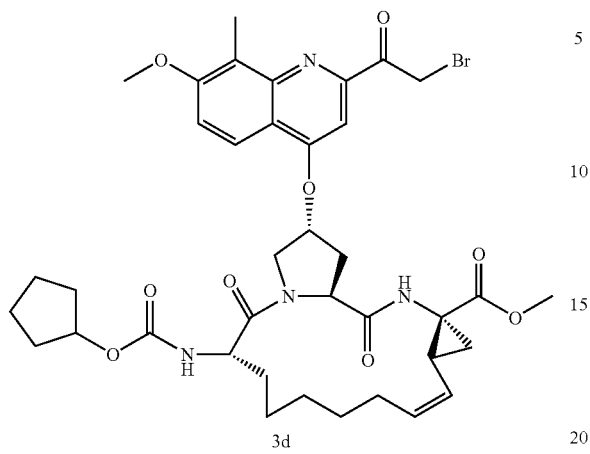

To the crude diazoketone 3c (assume 2.64 mmol) dissolved in THF (60 mL) was added dropwise, at 0° C., the HBr solution (48% aq.; 1.9 mL; 16.87 mmol) and stirred for 1 hour at 0° C. TLC (hexane:EtOAc; 5:5) after 2 hours indicated a complete reaction. The mixture was diluted with EtOAc, washed with saturated NaHCO$_3$ (2×), water (2×) and brine (1×), dried (MgSO$_4$), filtered and evaporated to provide the bromoketone product 3d as a yellow solid (2.03 g; crude; 2.59 mmol).

M.S. (electrospray) 783 (M) 785.3 (M+2).

Example 3B

Synthesis of Compound 101

Step A

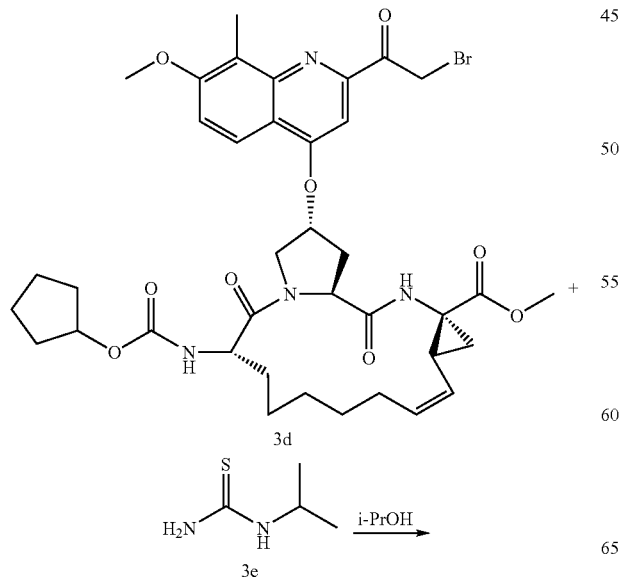

The crude α-bromoketone 3d (71 mg; 0.91 mmol) and the N-isopropylthiourea 3e (11.8 mg; 0.10 mmol) dissolved in isopropanol (3.0 mL) was stirred for 1.5 hours in a preheated 70° C. oil bath. TLC (Hexane:EtOAc; 5:5) indicated a complete reaction. The mixture was cooled to R.T., evaporated to dryness, diluted with EtOAc washed with saturated NaHCO$_3$ (2×), water (2×) and brine (1×), dried (MgSO$_4$), filtered and evaporated to provide the crude product 3f as a yellow solid.

M.S. (electrospray): 803.4 (M+H)$^+$. Reverse Phase HPLC Homogeneity @ 220 nm (0.06% TFA; CH$_3$CN:H$_2$O): 90%

Step B

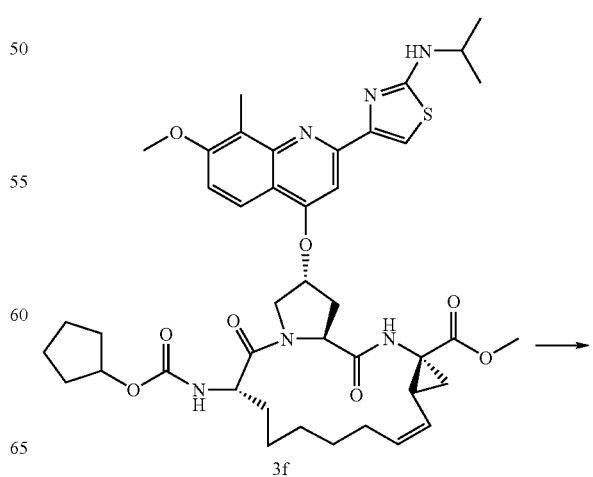

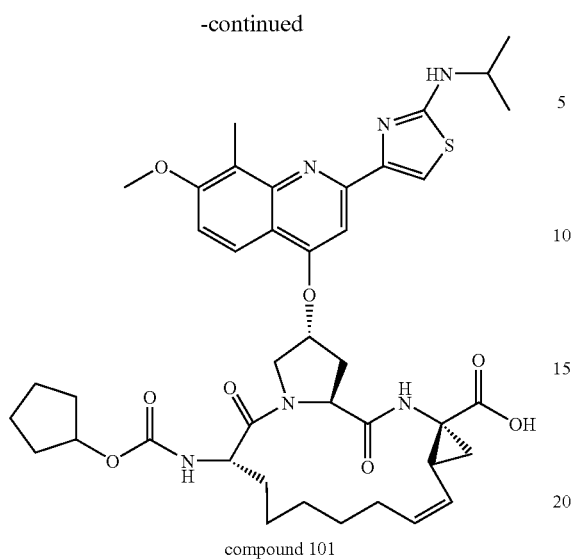

compound 101

A solution of methyl ester 3f (assume 0.091 mmol)) in THF (2 mL), MeOH (1 mL) and an aqueous solution of LiOH (38.2 mg; 0.91 mmol) in water (1 mL) was stirred overnight The organic solution was concentrated to provide a yellow paste. The crude material was purified by preparatory HPLC (YMC CombiScreen ODS-AQ, 50×20 mm ID S-5 micron, 120A @ 220 nm) using a linear gradient and 0.06% TFA CH$_3$CN/H$_2$O. The pure fractions were combined, concentrated, frozen and lyophilized to provide compound 101 as a yellow amorphous solid (45.3 mg; 63%).

M.S. (electrospray): 787.3 (M−H)⁻ 789.3 (M+H)⁺. Reverse Phase HPLC Homogeneity @ 220 nm (0.06% TFA; CH$_3$CN:H$_2$O): 99%. ¹H NMR (400 MHz, DMSO-d$_6$): δ 8.62 (s, 1H), 8.14-8.03 (m, 2H), 7.65-7.51 (m, 1H), 7.42-7.33 (m, 1H), 7.24 (d, J=6.5 Hz, 1H), 5.60 (bs, 1H), 5.58-5.47 (m, 1H), 5.28 (dd, J=9.6, 19.2 Hz, 1 Hz), 4.59-4.45 (m, 3H), 4.11-4.06 (m, 2H), 3.96 (s, 3H), 3.95-3.82 (m, 1H), 2.56 (s, 3H), 2.58-2.50 (m, 1H), 2.44-2.35 (m, 1H), 2.34-2.14 (m, 1H), 2.21-2.14 (m, 1H), 1.82-1.69 (m, 2H), 1.55-1.26 (m, 17H), 1.27 (d, J=6.3 Hz, 6H).

Example 3C

Synthesis of Compound 102

Step A

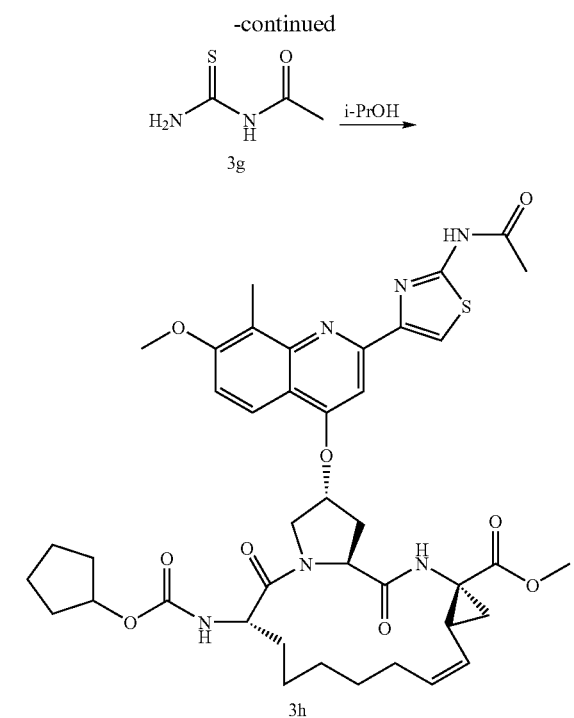

3h

The crude alpha-bromoketone 3d (71 mg; 0.91 mmol) and 1-acetyl-2-thiourea 3g (11.8 mg; 0.10 mmol) dissolved in isopropanol (3.0 mL). was stirred for 1.5 hours in a pre-heated 70° C. oil bath. TLC (Hexane:EtOAc; 5:5) indicated a complete reaction. The mixture was cooled to R.T., evaporated to dryness, diluted with EtOAc washed with saturated NaHCO$_3$ (2×), water (2×) and brine (1×), dried (MgSO$_4$), filtered and evaporated to provide the crude product 3h as a yellow solid (assume 0.091 mmol). M.S. (electrospray): 803.4 (M+H)⁺. Reverse Phase HPLC Homogeneity @ 220 nm (0.06% TFA; CH$_3$CN:H$_2$O): 92%.

Step B

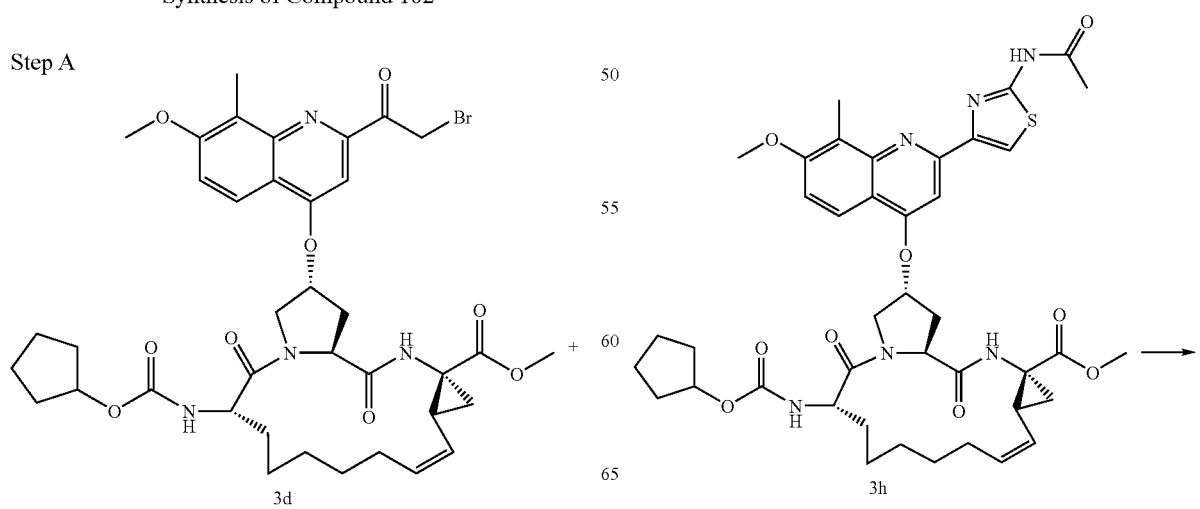

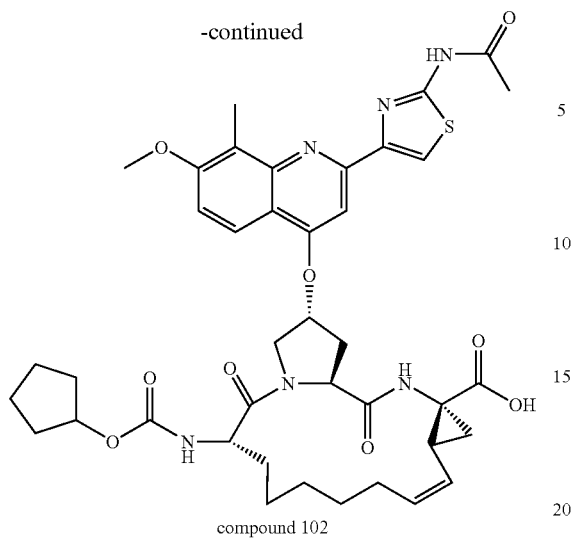

compound 102

A solution of methyl ester 3h (assume 0.091 mmol)) in THF (2 mL), MeOH (1 mL) and an aqueous solution of LiOH (38.2 mg; 0.91 mmol) in water (1 mL) was stirred overnight The organic solution was concentrated to provide an yellow paste. The crude material was purified by preparatory HPLC (YMC CombiScreen ODS-AQ, 50×20 mm ID S-5 micron, 120A @ 220 nm) using a linear gradient and 0.06% TFA $CH_3CN/H_2O$. The pure fractions were combined, concentrated, frozen and lyophilized to provide compound 102 as a yellow amorphous solid (45.9 mg; 64%).

M.S. (electrospray): 787.3 (M−H)⁻ 789.3 (M+H)⁺. Reverse Phase HPLC Homogeneity @ 220 nm (0.06% TFA; $CH_3CN:H_2O$): 99%. ¹H NMR (400 MHz, DMSO-$d_6$): δ 12.39 (s, 1H), 8.62 (s, 1H), 8.13-8.05 (m, 1H), 8.07 (d, J=9 Hz, 1H), 7.47 (s, 1H), 7.32 (d, J=9.2 Hz, 1H), 7.25 (d, J=6.7 Hz, 1H), 5.56-5.46 (m, 2H), 5.28 (dd, J=9.8, 19.2 Hz, 1 Hz), 4.62-4.53 (m, 2H), 4.47 (dd, J=8, 16.2 Hz, 1H), 4.14-4.05 (m, 1H), 4.05-3.93 (m, 1H), 3.95 (s, 3H), 2.60 (s, 3H), 2.61-2.50 (m, 1H), 2.42-2.31 (m, 1H), 2.20 (s, 3H), 1.82-1.69 (m, 2H), 1.69-1.13 (m, 19H)

Example 3D

Synthesis of Compound 103

The synthesis of compound 103 was carried out using the same reaction sequence as described in Example 3B above but using 2-methylpropionylthiourea instead of N-isopropylthiourea.

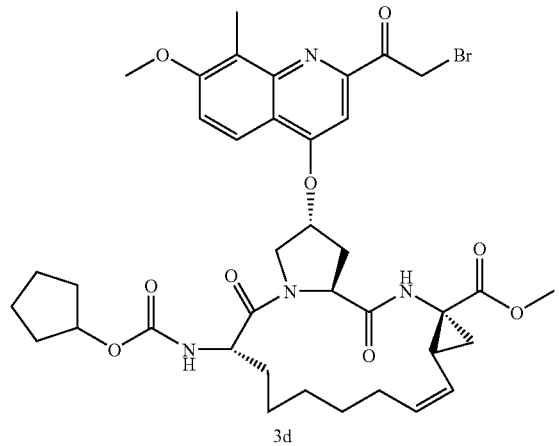

3d

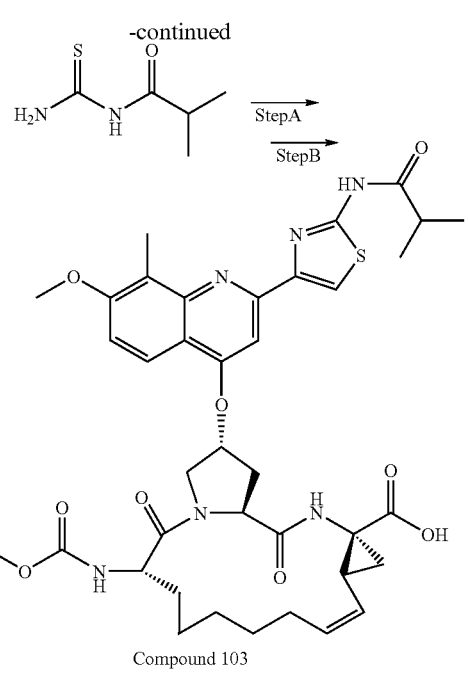

Compound 103

Compound 103 was obtained in 60% yield. M.S. (electrospray): 815.4 (M−H)⁻ 817.4 (M+H)⁺. Reverse Phase HPLC Homogeneity @ 220 nm (0.06% TFA; $CH_3CN:H_2O$): 99%.

¹H NMR (400 MHz, DMSO-$d_6$): δ 12.30 (s, 1H), 8.62 (s, 1H), 8.03 (s, 2H), 7.43 (s, 1H), 7.28 (d, J=9.4 Hz, 1H), 7.24 (d, J=6.9 Hz, 1H), 5.52 (dd, J=8.3, 18.2 Hz, 1H), 5.45 (bs, 1H), 5.28 (dd, J=9.4, 19.2 Hz, 1H), 4.63 (bs, 1H), 4.54 (d, J=11.2 Hz, 1H), 4.46 (dd, J=8.0, 16.0 Hz, 1H), 4.13 (dd, J=8.0, 16.0 Hz, 1H), 3.93 (s, 3H), 3.99-3.90 (m, 1H), 2.86-2.79 (m, 1H), 2.60 (s, 3H), 2.57-2.50 (m, 1H), 2.40-2.33 (m, 1H), 2.23-2.17 (m, 1H), 1.79-1.11 (m, 20H), 1.16 (d, J=6.1 Hz, 6H)

Example 3E

Synthesis of Compound 105

The synthesis of compound 105 was carried out using the same reaction sequence as described in Examples 3A and 3B but using 2-carbomethoxy-8-bromo-4-hydroxy-7-methoxyquinoline (B6) instead of 2-carbomethoxy-4-hydroxy-7-methoxy-8-methylquinoline (A5) in step A of Example 3A; and using propionylthiourea instead of N-isopropylthiourea in step A of Example 3B.

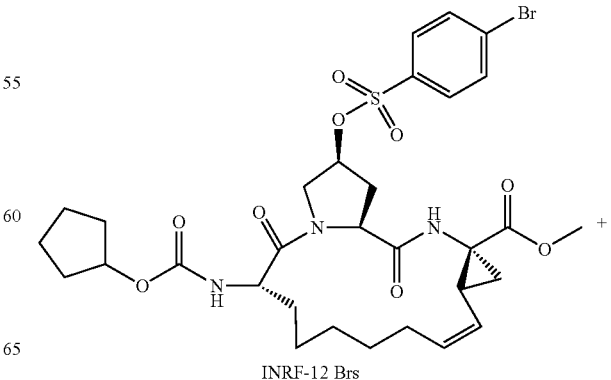

INRF-12 Brs

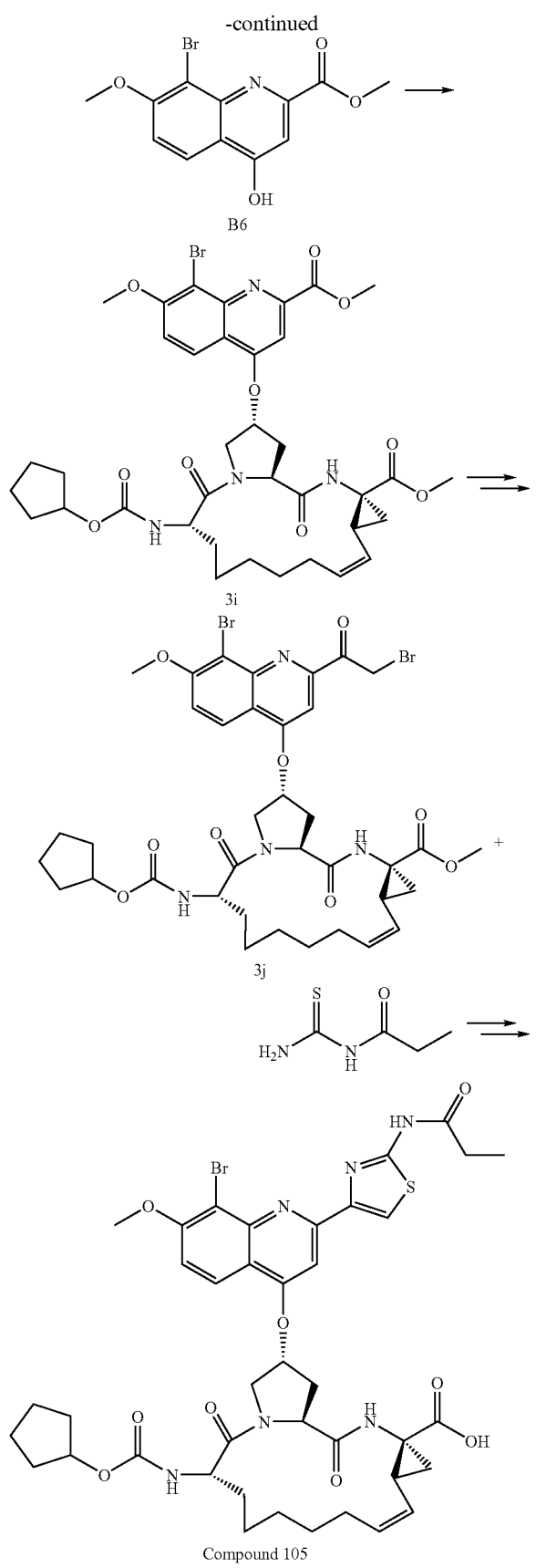

Compound 105

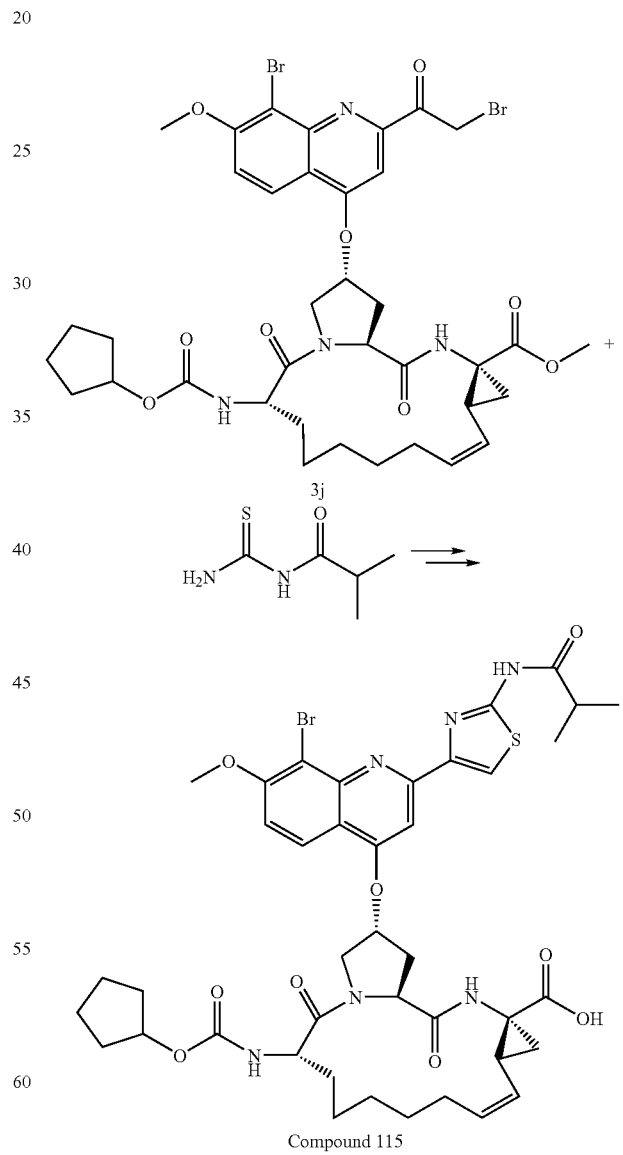

Compound 115

Compound 105 was obtained as a lyophilized solid.
$^1$H NMR (400 MHz, DMSO-$d_6$): δ 12.33 (s, 1H), 8.62 (s, 1H), 8.17 (d, J=9.1 Hz, 1H), 8.04 (s, 1H), 7.49 (s, 1H), 7.37 (d, J=9.4 Hz, 1H), 7.23 (d, J=6.7 Hz, 1H), 5.57-5.45 (m, 2H), 5.28 (t, J=9.5 Hz, 1H), 4.62-4.54 (m, 2H), 4.53-4.44 (m, 2H), 4.12-4.04 (m, 1H), 4.01 (s, 3H), 3.95-3.87 (m, under H$_2$O, 1H), 2.58-2.44 (m, under DMSO, 4H), 2.43-2.33 (m, 1H), 2.25-2.12 (m, 1H), 1.80-1.18 (m, 19H), 1.13 (t, J=7.4 Hz, 3H). M.S. (electrospray): 867.3 (M+H)+. Reverse Phase HPLC Homogeneity (0.06% TFA; CH$_3$CN:H$_2$O) 98%

Example 3F

Synthesis of Compound 115

The synthesis of compound 115 was carried out using the same reaction sequence as described in Example 3E above but using 2-methylpropionylthiourea in place of propionylthiourea.

Compound 115 was obtained as a lyophilized solid
$^1$H NMR (400 MHz, DMSO-$d_6$): δ 12.33 (s, 1H), 8.62 (s, 1H), 8.17 (d, J=9.0 Hz, 1H), 8.04 (s, 1H), 7.50 (s, 1H), 7.37 (d, J=9.4 Hz, 1H), 7.23 (d, J=6.9 Hz, 1H), 5.58-5.44 (m, 2H), 5.28 (t, J=9.6 Hz, 1H), 4.62-4.44 (m, 3H), 4.13-4.04 (m, 1H), 4.01 (s, 3H), 3.95-3.86 (m, 1H), 2.88-2.75 (m, 1H), 2.61-2.45 (m, under DMSO, 4H), 2.44-2.38 (m, 1H), 2.25-2.12 (m, 1H), 1.80-1.25 (m, 18H), 1.16 (d, J=6.1 Hz, 6H). M.S. (electrospray): 881.1 (M−H)− 883.2 (M+H)+. Reverse Phase HPLC Homogeneity (0.06% TFA; CH$_3$CN:H$_2$O): 97%

Example 3G

Synthesis of Compound 113

The synthesis of compound 113 was carried out using the same reaction sequence as described in Examples 3A and 3B but using 2-carbomethoxy-8-chloro-4-hydroxy-7-methoxyquinoline (C6) instead of 2-carbomethoxy-4-hydroxy-7-methoxy-8-methylquinoline (A5) in step A of Example 3A; and using butenylthiourea instead of N-isopropylthiourea in step A of Example 3B.

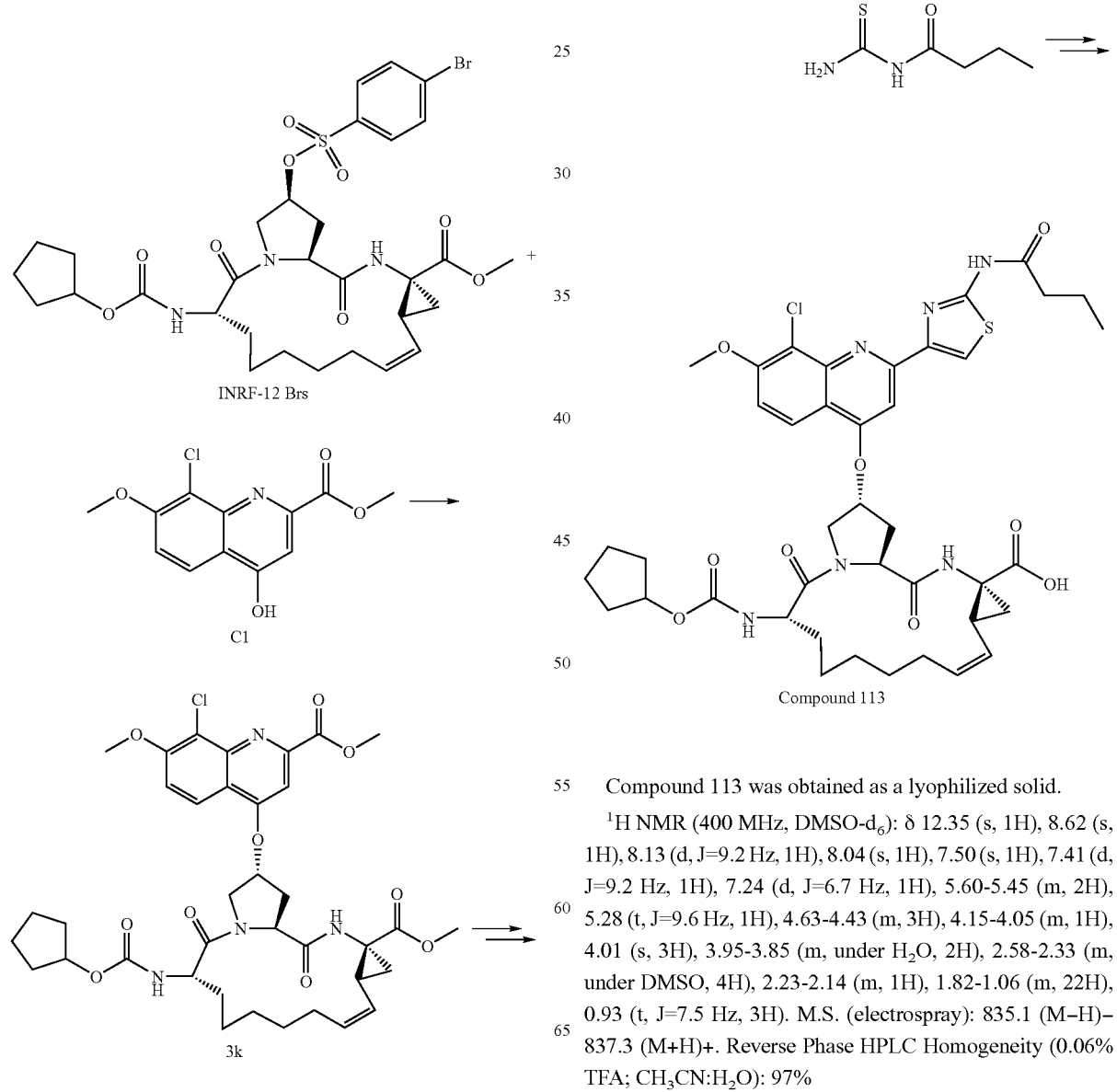

Compound 113

Compound 113 was obtained as a lyophilized solid.

$^1$H NMR (400 MHz, DMSO-d$_6$): δ 12.35 (s, 1H), 8.62 (s, 1H), 8.13 (d, J=9.2 Hz, 1H), 8.04 (s, 1H), 7.50 (s, 1H), 7.41 (d, J=9.2 Hz, 1H), 7.24 (d, J=6.7 Hz, 1H), 5.60-5.45 (m, 2H), 5.28 (t, J=9.6 Hz, 1H), 4.63-4.43 (m, 3H), 4.15-4.05 (m, 1H), 4.01 (s, 3H), 3.95-3.85 (m, under H$_2$O, 2H), 2.58-2.33 (m, under DMSO, 4H), 2.23-2.14 (m, 1H), 1.82-1.06 (m, 22H), 0.93 (t, J=7.5 Hz, 3H). M.S. (electrospray): 835.1 (M−H)− 837.3 (M+H)+. Reverse Phase HPLC Homogeneity (0.06% TFA; CH$_3$CN:H$_2$O): 97%

Example 4

Synthesis of Compound 201

Step A

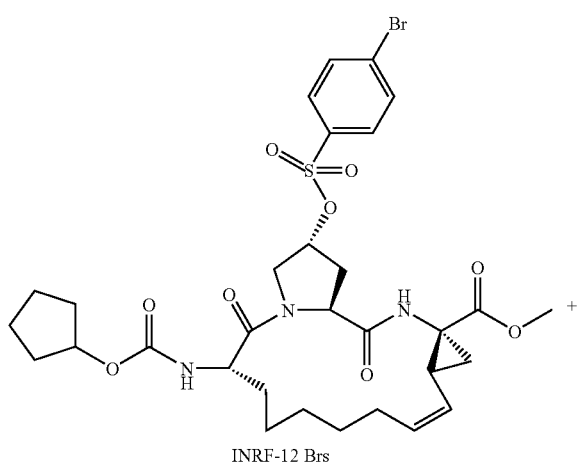

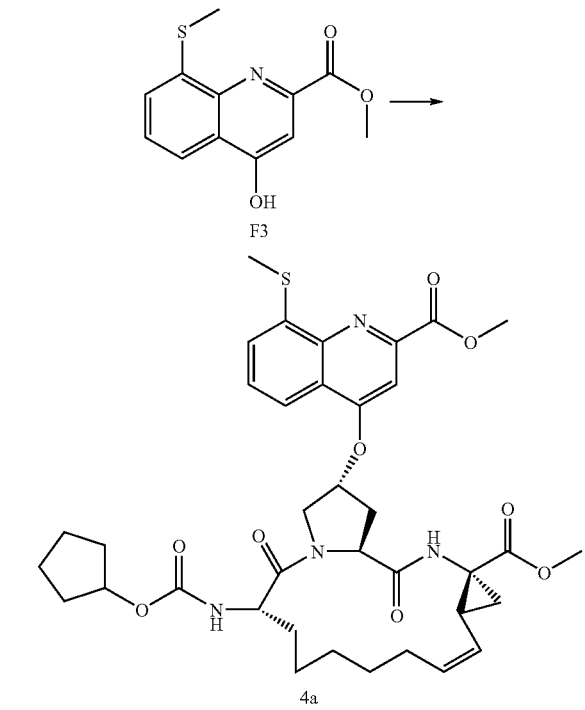

To a solution of brosylate INRF-12 Brs (1.4 g, 2.0 mmol) and the quinoline F3 (0.5 g, 2.0 mmol) in 1-methyl-2-pyrrolidinone (NMP, 7 mL) was added cesium carbonate (0.78 g, 2.4 mmol). The mixture was heated to 70° C. overnight, then cooled, poured into EtOAc, and washed with H₂O (2×), NaHCO₃ saturated solution containing 1M NaOH (3/1 mixture) (2×), and brine (3×). The organic phase was dried, filtered and concentrated to afford the crude product 4a as a yellow oil. This material was purified by flash chromatography using regular SiO₂ (250-400 Mesh) eluting with 55% EtOAc/hexane to afford 903 mg of a yellow solid (yield 62%).

Step B

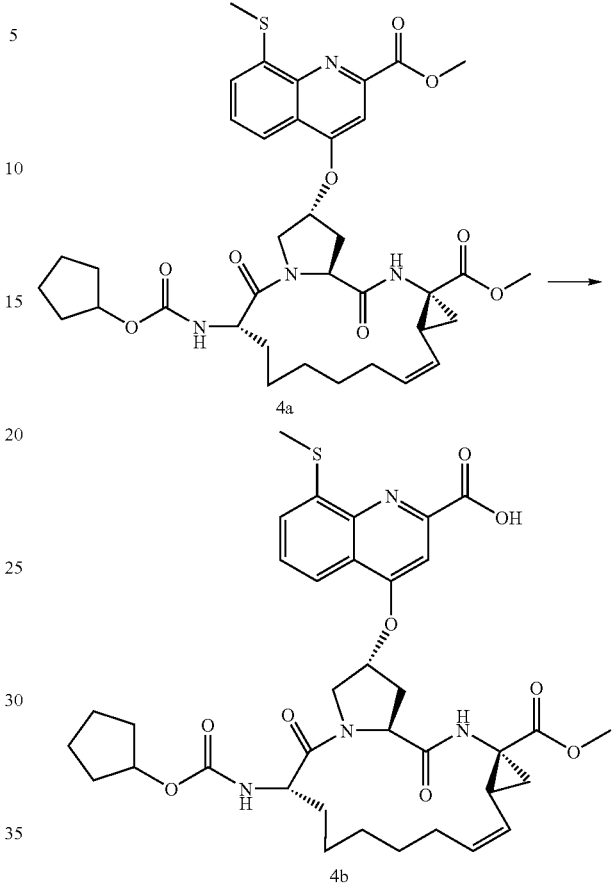

To a solution of the ester 4a (0.9 g, 1.25 mmol) in a mixture of THF/MeOH (8 mL each) was added NaOH 1M (1.33 mL, 1.33 mmol). The reaction mixture was stirred at RT for 18 hours followed by concentration to dryness to afford 0.8 g of compound 4b as a beige solid (quantitative). The residue was used as such for the next step.

Step C

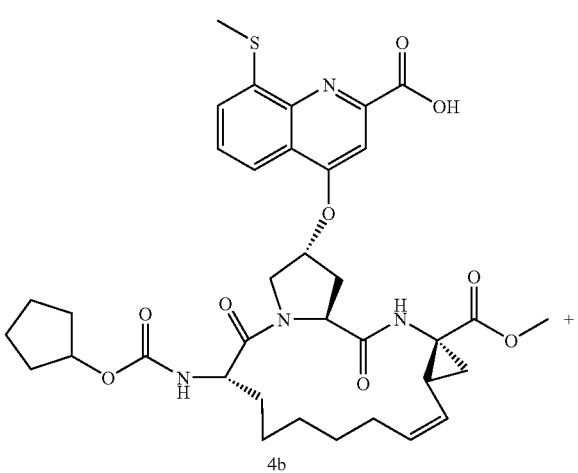

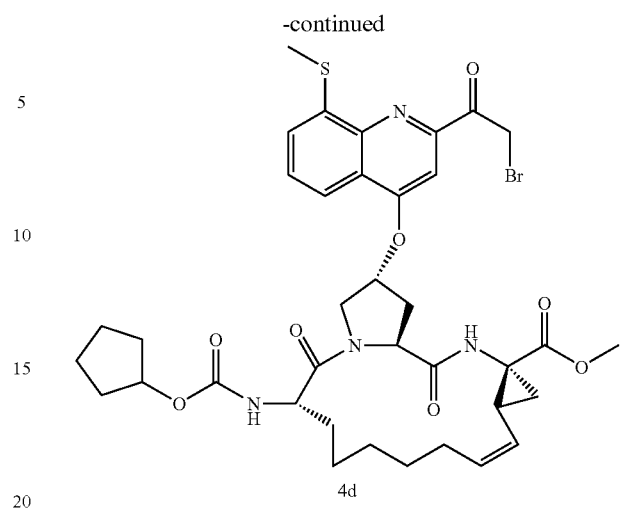

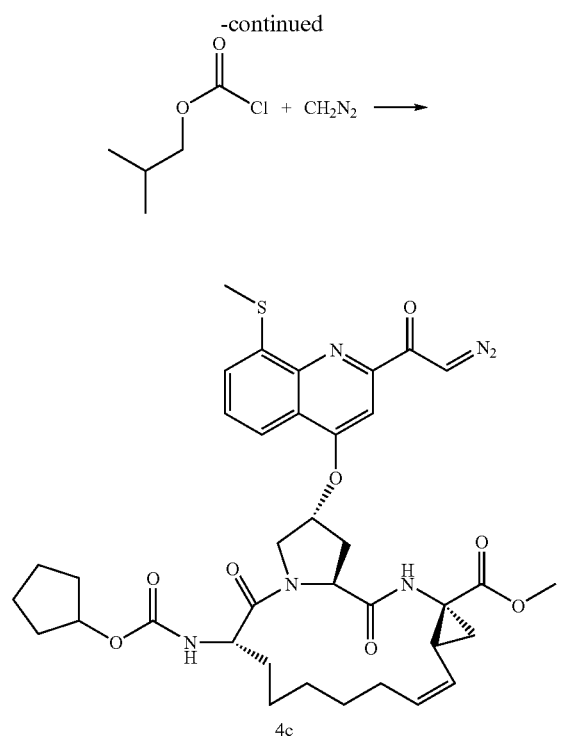

To a solution of the acid 4b (sodium salt) (0.8 g, 1.23 mmol) in THF (14 mL) at 0° C., was added Et₃N (0.51 mL, 3.7 mmol), followed by isobutyl chloroformate (0.32 mL, 2.4 mmol). The reaction mixture was stirred at 0° C. for 1 hour, then diazomethane (6 mL, 6.1 mmol) was added. The mixture was stirred for another 10 min at 0° C., then at RT for 2 hours. The mixture was concentrated to dryness and the residue was diluted with EtOAc. The organic phase was washed with a saturated NaHCO₃ soln (2×) and brine; dried (MgSO₄), filtered and concentrated under reduced pressure to afford 956 mg of 4c as a pale yellow solid (quantitative), which was used as such for the next step, without any further characterization.

Step D

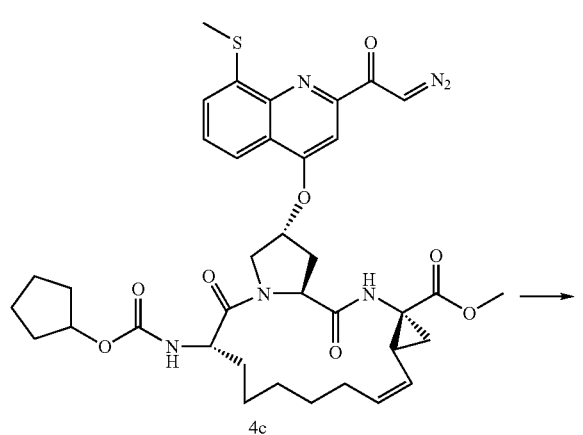

To the diazoketone 4c (0.96 g, 1.31 mmol) in THF (11 mL) at 0° C., was added HBr soln (48%) (0.55 mL, 3.2 mmol). The reaction mixture was stirred at 0° C. for 1.5 h, then was neutralized with satd NaHCO₃ solution. The mixture was concentrated to dryness and the residue was diluted with EtOAc. The organic phase was washed with a satd NaHCO₃ soln, H₂O and brine, dried (MgSO₄), filtered and concentrated under reduced pressure to afford 780 mg of 4d as a yellow solid (yield 76%), which was used as such for the next step, without any further characterization.

Step E

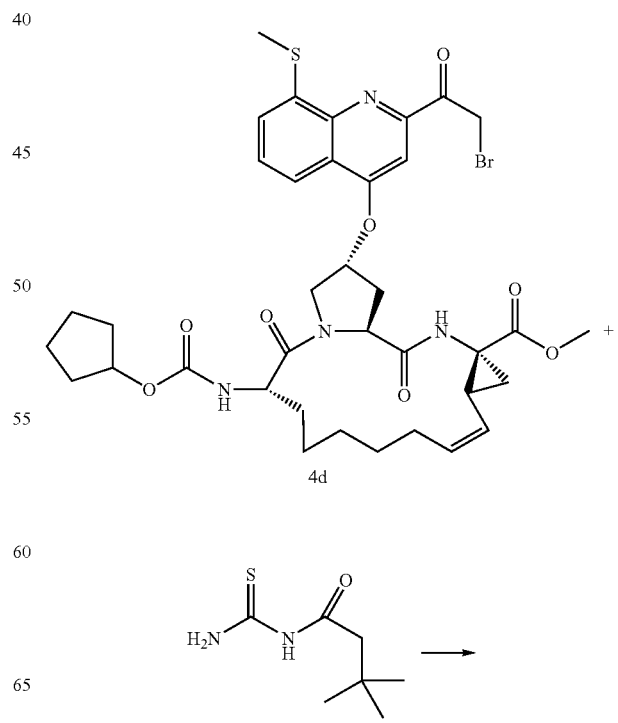

-continued

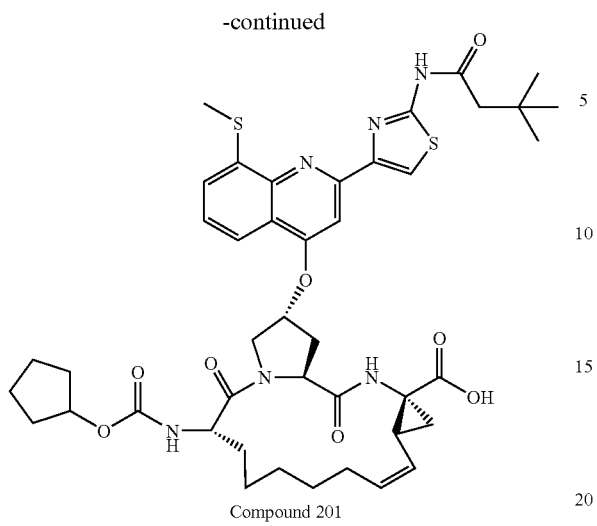

Compound 201

Bromoketone 4d (0.065 g, 0.08 mmol) was dissolved in isopropanol (3 mL) and 3,3-dimethylbutanoylthiourea (15.8 mg, 0.1 mmol) was added to the solution. The reaction mixture was stirred at 70° C. for 45 min, at which point the starting material was consumed as shown by TLC. HPLC along with mass spectra confirmed the new product. The mixture was cooled to RT and THF (2 mL) and NaOH 1M solution were added. The reaction mixture was stirred at RT overnight, then concentrated.

The residue was dissolved in DMSO and purified by prep HPLC (Combiprep ODS-AQ, 20×50 mm) to give 20 mg of compound 201 as a yellow lyophilized solid (yield 31%).

$^1$H NMR (400 MHz, DMSO-d$_6$)-12.27 (s, 1H), 8.60 (s, 1H), 7.94 (s, 1H), 7.90 (d, J=7.8 Hz, 1H), 7.56 (s, 1H), 7.50-7.35 (m, 2H), 7.25 (d, J=6.7 Hz, 1H), 5.60-5.45 (m, 3H), 5.34-5.20 (m, 1H), 4.65-4.55 (m, 2H), 4.50-4.40 (m, 1H), 4.15-4.05 (m, 1H), 3.95-3.85 (m, 1H), 2.66 (s, 3H, under DMSO signal), 2.42-2.31 (m, 3H), 2.25-2.15 (m, 1H), 1.8-1.1 (m, 20H), 1.03 (s, 9H). MS (ESI) (M−H)=846.3.

Example 5

Synthesis of Compound 209

Step A

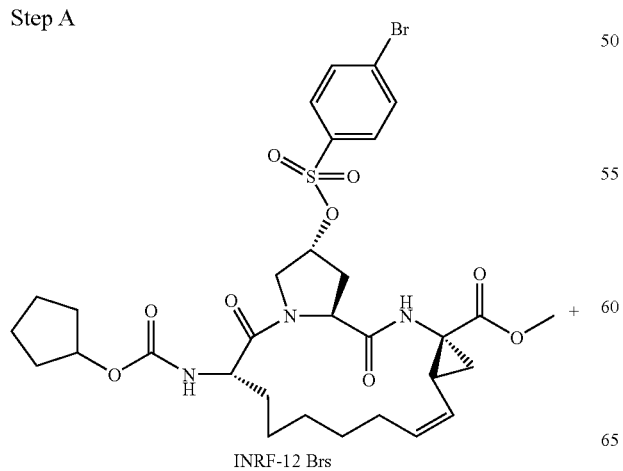

INRF-12 Brs

-continued

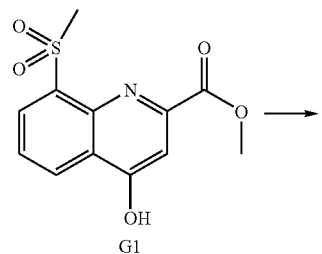

G1

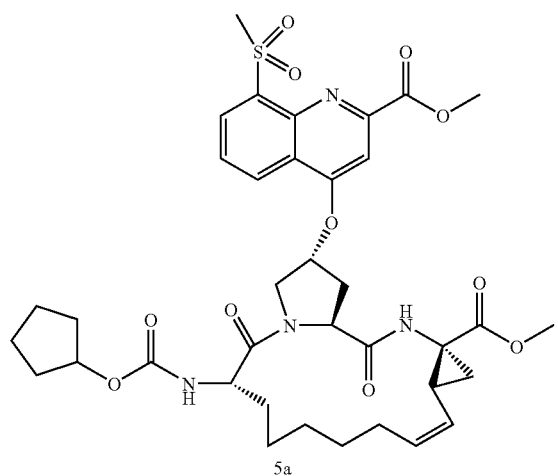

5a

To a solution of brosylate INRF-12 Brs (0.95 g, 1.33 mmol) and the quinoline G1 (0.37 g, 1.33 mmol) in 1-methyl-2-pyrrolidinone (NMP, 5 mL) was added cesium carbonate (0.52 g, 1.60 mmol). The mixture was heated to 70° C. overnight, then cooled, poured into EtOAc, and washed with H$_2$O (2×), NaHCO$_3$ saturated solution containing 1M NaOH (3/1 mixture) (2×), and brine (3×). The organic phase was dried, filtered and concentrated to afford the crude product 5a as a yellow oil. This material was purified by flash chromatography using regular SiO$_2$ (250-400 Mesh) eluting with 55% EtOAc/hexane to afford 294 mg of a white solid (yield 29%).

Step B

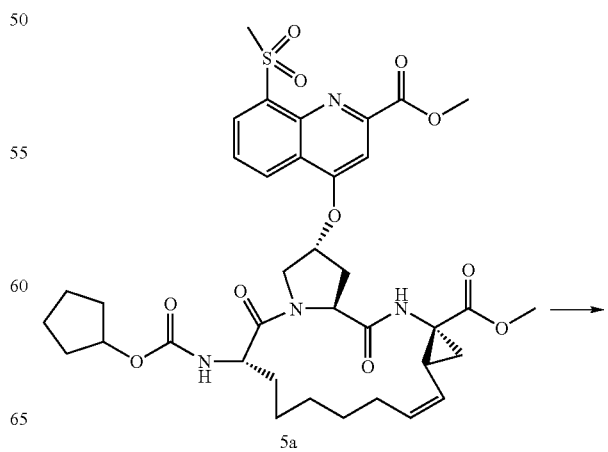

5a

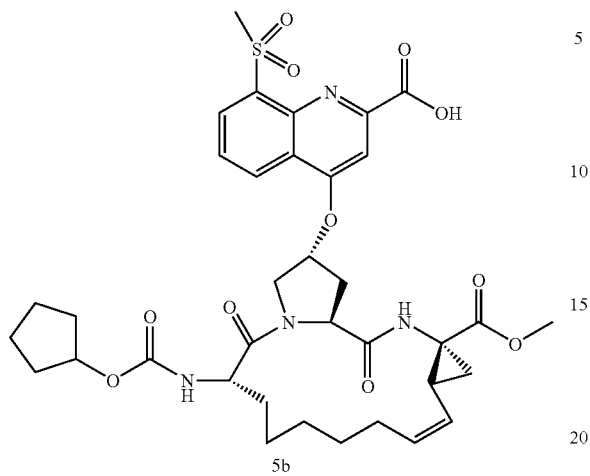

5b

To a solution of the ester 5a (0.24 g, 0.32 mmol) in a mixture of THF/MeOH (5 mL each) was added NaOH 1M (0.33 mL, 0.33 mmol). The reaction mixture was stirred at RT for 18 hours followed by concentration to dryness to afford 230 mg of compound 5b as a beige solid (98%). The residue was used as such for the next step.

Step C

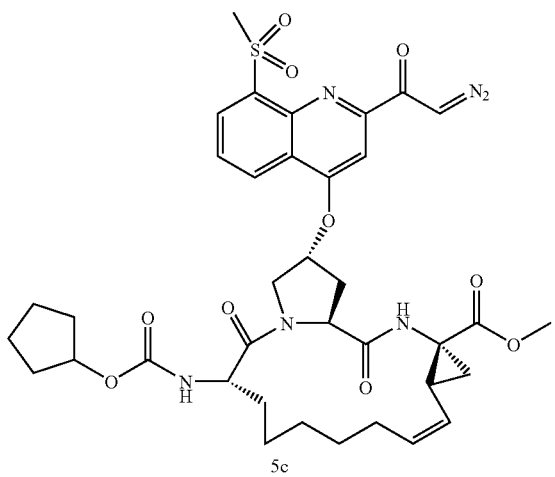

5c

To a solution of the acid 5b (sodium salt) (0.23 g, 0.31 mmol) in THF (5 mL) at 0° C., was added Et₃N (0.13 mL, 0.93 mmol), followed by isobutyl chloroformate (0.08 mL, 0.62 mmol). The reaction mixture was stirred at 0° C. for 1 hour, then diazomethane (2 mL, 1.55 mmol) was added. The mixture was stirred for another 10 min at 0° C., then at RT for 2 hours. The mixture was concentrated to dryness and the residue was diluted with EtOAc. The organic phase was washed with a saturated NaHCO₃ soln (2×) and brine; dried (MgSO₄), filtered and concentrated under reduced pressure to afford 237 mg of 5c as a pale yellow solid (yield 99%), which was used as such for the next step, without any further characterization.

Step D

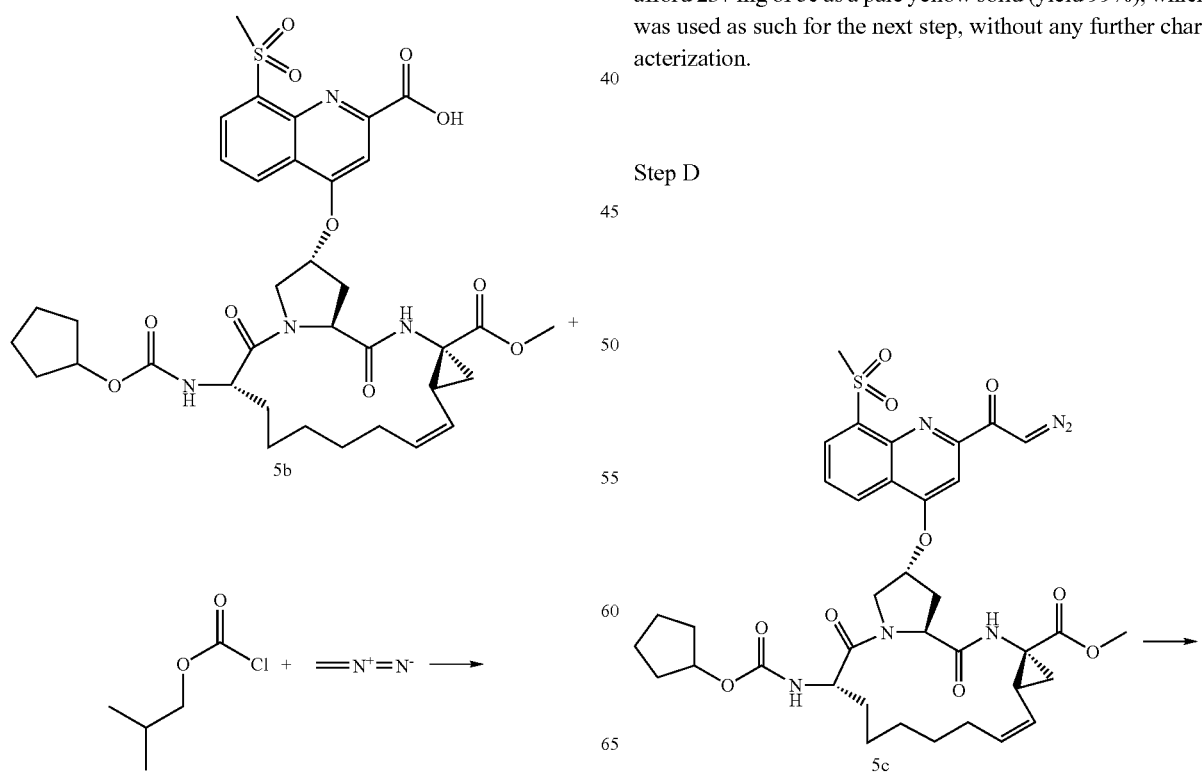

-continued

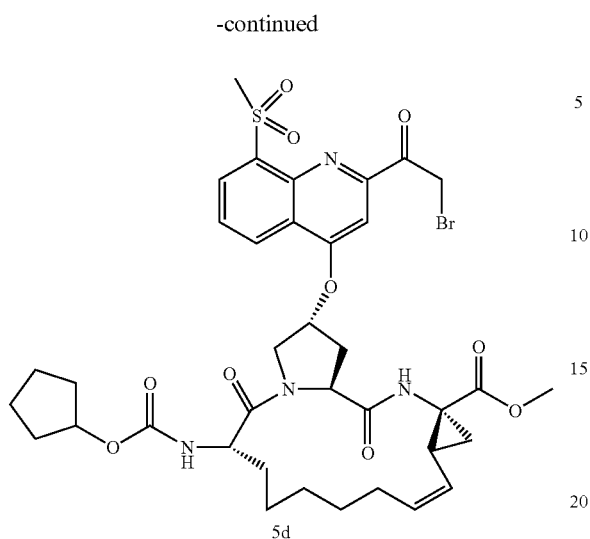

5d

To the diazoketone 5c (0.24 g, 0.31 mmol) in THF (5 mL) at 0° C., was added HBr soln (48%) (0.13 mL, 0.77 mmol). The reaction mixture was stirred at 0° C. for 1.5 h, then was neutralized with satd NaHCO₃ solution. The mixture was concentrated to dryness and the residue was diluted with EtOAc. The organic phase was washed with a satd NaHCO₃ soln, H₂O and brine, dried (MgSO₄), filtered and concentrated under reduced pressure to afford 205 mg of 5d as a yellow solid (yield 81%), which was used as such for the next step, without any further characterization.

Step E

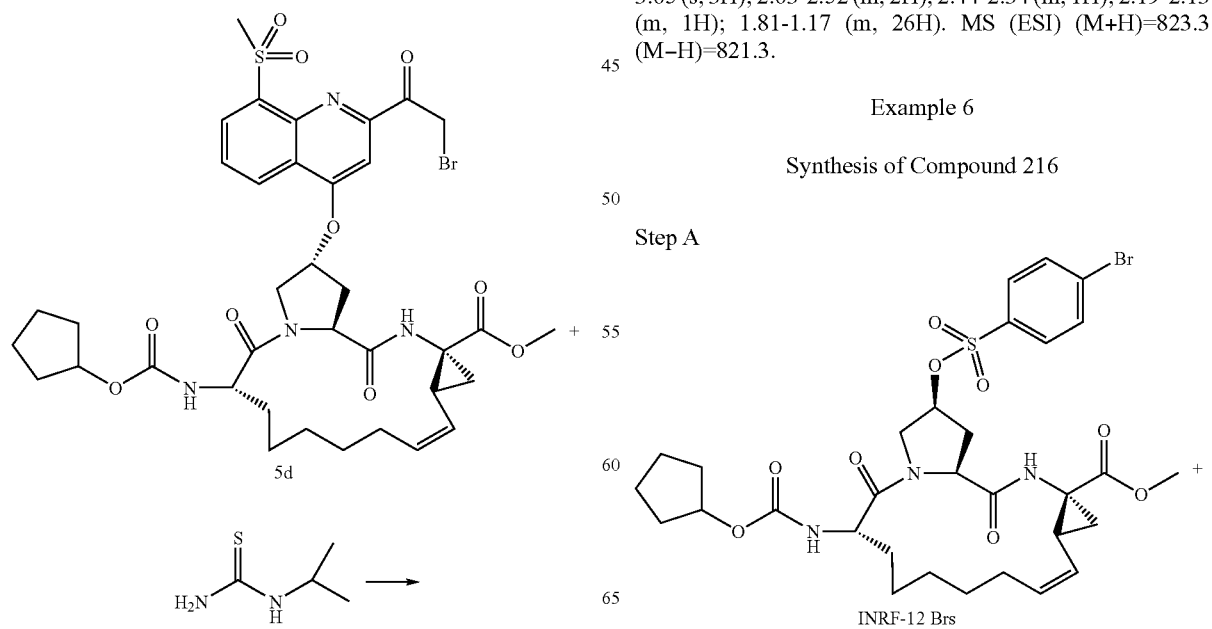

-continued

Compound 209

Bromoketone 5d (0.045 g, 0.05 mmol) was dissolved in isopropanol (3 mL) and isopropylthiourea (7.8 mg, 0.06 mmol) was added to the solution. The reaction mixture was stirred at 70° C. for 45 min, at which point the starting material was consumed as shown by TLC. HPLC along with mass spectra confirmed the new product. The mixture was cooled to RT and THF (2 mL) and NaOH 1M solution were added. The reaction mixture was stirred at RT overnight, then concentrated.

The residue was dissolved in DMSO and purified by prep HPLC (Combiprep ODS-AQ, 20×50 mm) to give 17 mg of compound 209 as a yellow lyophilized solid (yield 45%).

$^1$H NMR (400 MHz, DMSO-$d_6$) 8.59 (s, 1H); 8.47 (d, J=8.2 Hz, 1H); 8.34 (d, J=7.3 Hz, 1H); 7.81 (broad s, 1H); 7.67 (s, 1H); 7.61 (t, J=7.8 Hz, J=15.6 Hz, 1H); 7.55 (s, 1H); 7.24 (d, J=6.3 Hz, 1H); 5.58 (s, 1H); 5.48-5.54 (m, 1H); 5.26 (t, J=9.7 Hz, J=19.1 Hz, 1H); 4.57-4.55 (m, 2H); 4.47 (t, J=8.0 Hz, J=16.4 Hz, 1H); 4.09-4.05 (m, 1H); 3.92-3.85 (m, 2H); 3.65 (s, 3H); 2.63-2.52 (m, 2H); 2.44-2.34 (m, 1H); 2.19-2.13 (m, 1H); 1.81-1.17 (m, 26H). MS (ESI) (M+H)=823.3 (M−H)=821.3.

Example 6

Synthesis of Compound 216

Step A

-continued

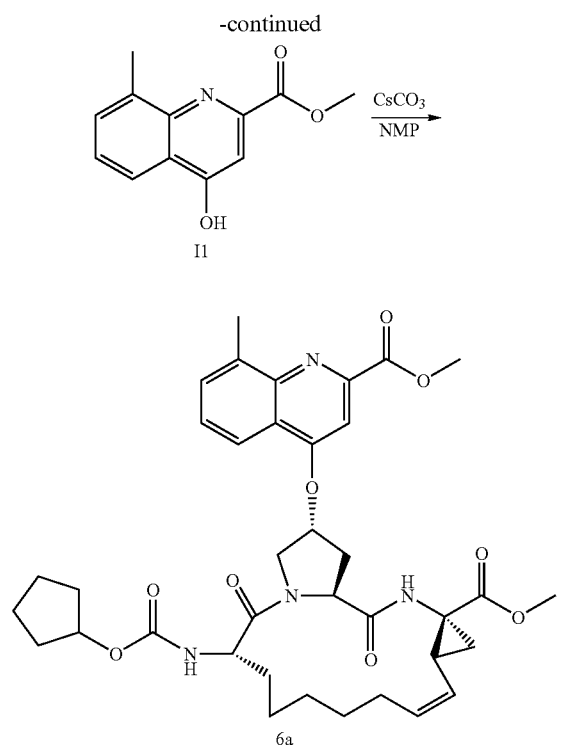

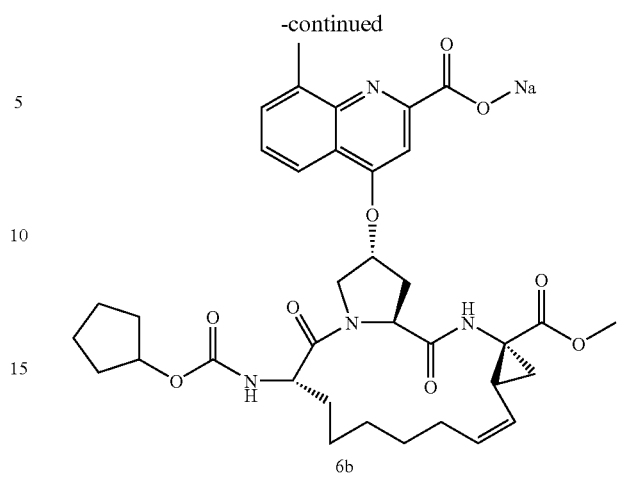

To a solution of the brosylate INRF-12 Brs (0.98 g; 1.38 mmol) and quinoline I1 (0.30 g; 1.38 mmol) in 1-methyl-2-pyrrolidinone (18 mL) was added ground cesium carbonate (0.54 g; 1.66 mmol). The resulting suspension was stirred for 6 hours in a preheated 40° C. oil bath, then, at room temperature overnight. The reaction mixture was diluted with EtOAc, washed extensively with H₂O (3×), NaHCO₃ (sat'd; 2×), water (2×) and brine (2×), dried (MgSO₄), filtered and concentrated followed by purification by column chromatography on silica gel column with hexane:EtOAc (5:5 to 4:6) provided the pure product 6a as an off-white solid (540 mg; 54%).

MS 719.3 (M−H)− 721.4 (M+H)+. Reverse Phase HPLC Homogeneity @ 220 nm (0.06% TFA; CH₃CN:H₂O): 96%

Step B

To the methyl ester 6a (541 mg; 0.78 mmol) dissolved in THF/MeOH/H₂O (3:2:1, 12 mL total volume) was added 1N NaOH (0.82 mL, 0.82 mmol). The yellow solution was stirred at room temperature for 2.5 hours (no visible starting material by HPLC).

The mixture was evaporated to near dryness, diluted with water, frozen and lyophilized to provide the sodium salt 6b as a white amorphous solid (530 mg; 100%) which was employed without further purification in the subsequent step.

Step C

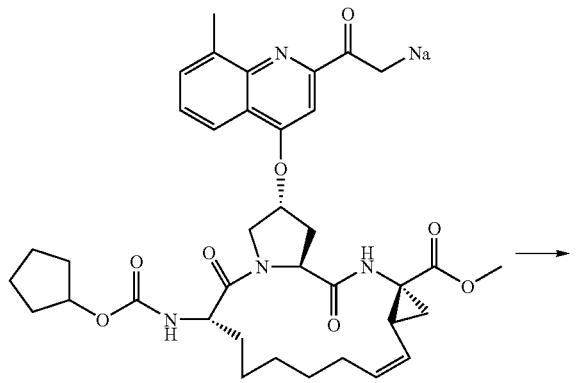

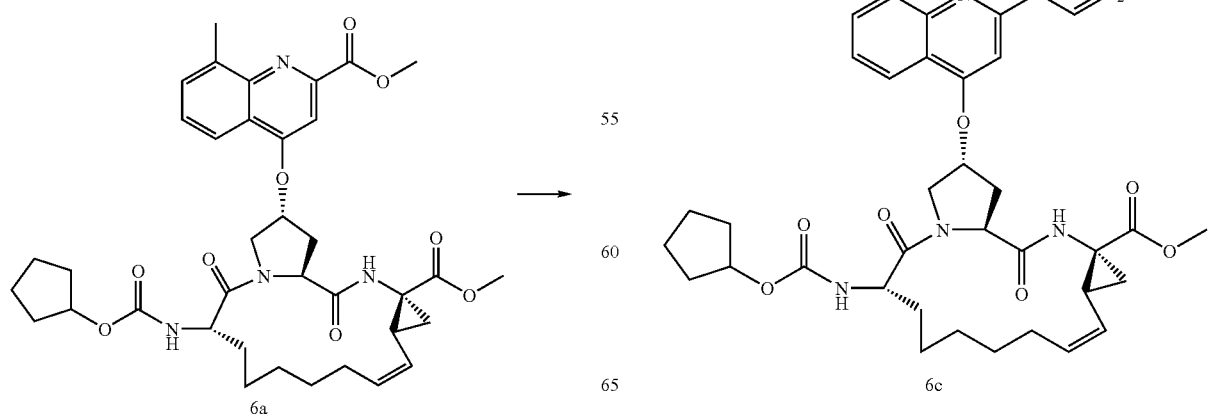

To a cooled (0° C.) solution of the crude mono-acid Na salt 6b (0.53 g, 0.78 mmol) in THF (7 mL), and triethylamine (0.35 mL; 2.51 mmol) was added dropwise isobutylchloroformate (0.23 mL; 1.72 mmol). The white suspension was stirred at 0° C. for 2 hours, then, diazomethane (0.67M in ether; 23.6 mL; 15.82 mmol) was added. The reaction mixture was stirred 1 hour at 0° C. and 1.5 hours at room temperature after which it was evaporated to near dryness to provide a thick suspension. This suspension was dissolved by dilution with EtOAc and water and washed with saturated NaHCO₃ (2×), water (2×) and brine (1×), dried (MgSO₄), filtered and evaporated to provide the diazoketone product 6c as an ivory solid (crude material used for next step).

M.S. (electrospray) 701.5 (M+H)⁺.

Step D

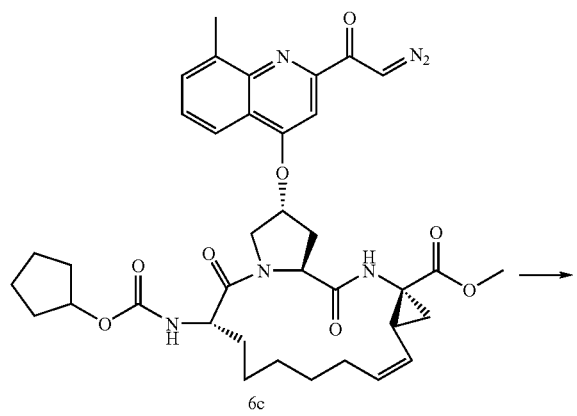

6c

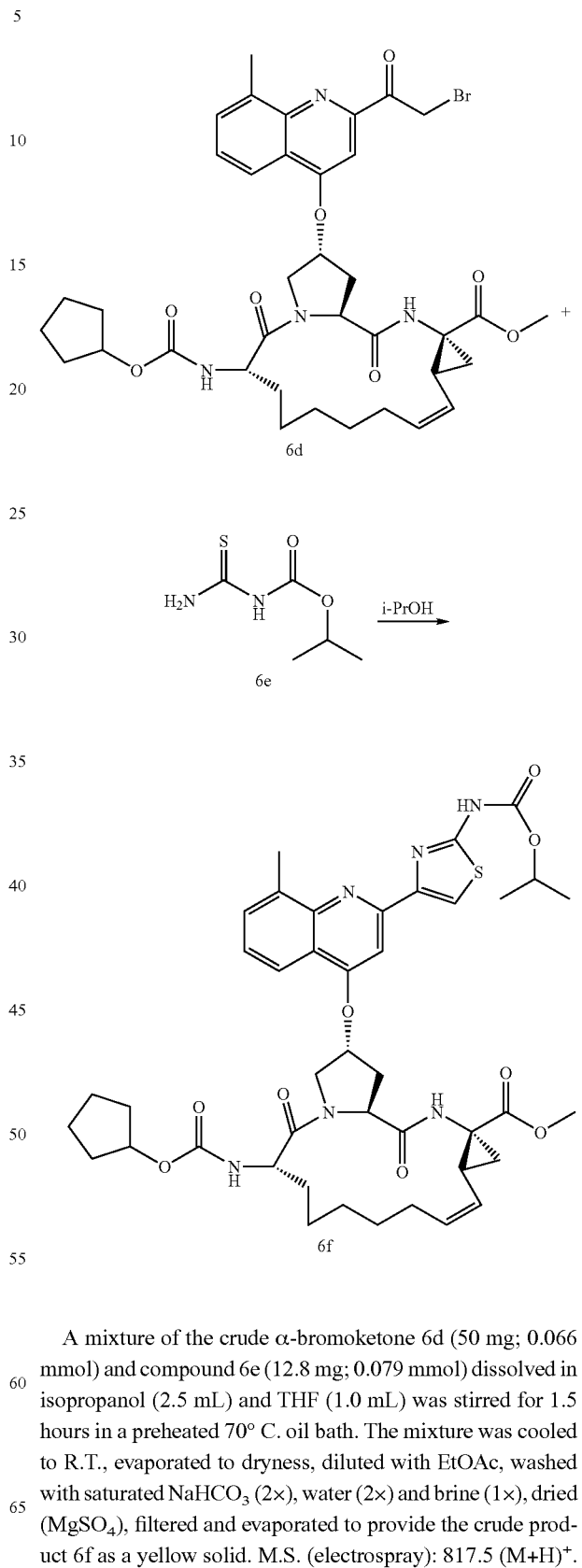

To the crude diazoketone 6c (373 mg, 0.53 mmol) dissolved in THF (5.3 mL) was added dropwise, at 0° C., the HBr solution (48% aq.; 0.24 mL) and stirred for 1 hour at 0° C. The mixture was diluted with EtOAc, washed with saturated NaHCO₃ (2×), water (2×) and brine (1×), dried (MgSO₄), filtered and evaporated to provide the bromoketone product 6d as a yellow solid (323 mg; crude; 0.43 mmol).

M.S. (electrospray) 753.3, 755.3 (M+).

Step E

A mixture of the crude α-bromoketone 6d (50 mg; 0.066 mmol) and compound 6e (12.8 mg; 0.079 mmol) dissolved in isopropanol (2.5 mL) and THF (1.0 mL) was stirred for 1.5 hours in a preheated 70° C. oil bath. The mixture was cooled to R.T., evaporated to dryness, diluted with EtOAc, washed with saturated NaHCO₃ (2×), water (2×) and brine (1×), dried (MgSO₄), filtered and evaporated to provide the crude product 6f as a yellow solid. M.S. (electrospray): 817.5 (M+H)⁺.

Step F

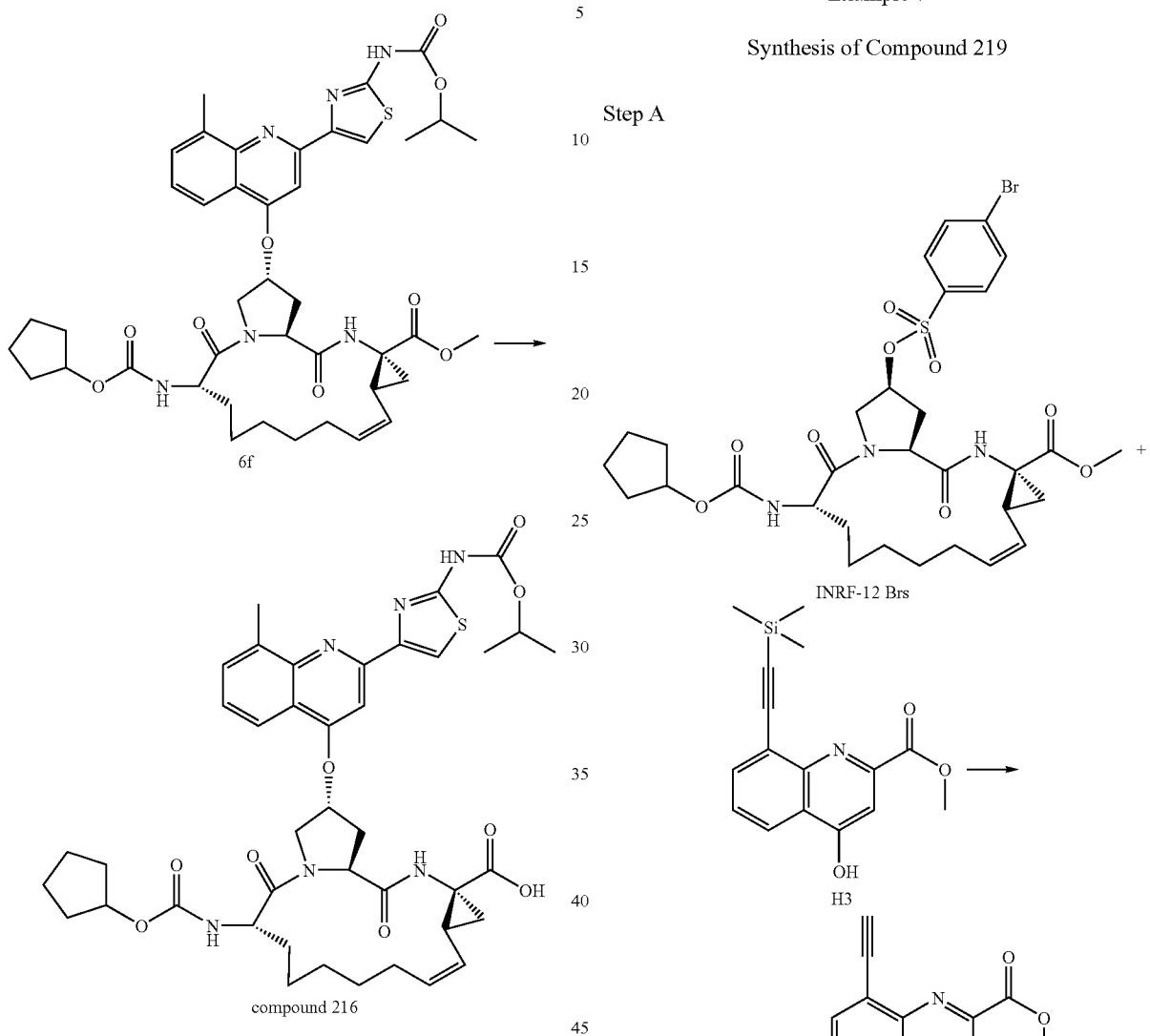

compound 216

A solution of methyl ester 6f (assume 0.091 mmol)) in THF (2 mL), MeOH (1 mL) and an aqueous solution of LiOH (38.2 mg; 0.91 mmol) in water (1 mL) was stirred overnight The organic solution was concentrated to provide a yellow paste. The crude material was purified by preparatory HPLC (YMC CombiScreen ODS-AQ, 50×20 mm ID S-5 micron, 120A @ 220 nm) using a linear gradient and 0.06% TFA CH₃CN/H₂O. The pure fractions were combined, concentrated, frozen and lyophilized to provide compound 216 as a yellow amorphous solid (13.6 mg; 23%).

M.S. (electrospray) 803.4 (M−H)⁻ 801.3 (M+H)⁺. Reverse Phase HPLC Homogeneity @ 220 nm (0.06% TFA; CH₃CN: H₂O): 99.8%. ¹H NMR (400 MHz, DMSO-d₆): δ 11.88 (s, 1H), 8.59 (s, 1H), 8.01-8.03 (m, 2H), 7.60 (d, J=6.9 Hz, 1H), 7.54 (s, 1H), 7.32 (t, J=7.7 Hz, 1H), 7.26 (d, J=6.9 Hz, 1H), 5.45-5.55 (m, 2H), 5.24-5.28 (m, 1H), 4.97 (quin., J=6.3 Hz, 1H), 4.63 (br s, 1H), 4.53-4.59 (m, 1H), 4.42-4.46 (m, 1H), 4.09-4.13 (m, 1H), 3.90-3.95 (m, 1H), 2.74 (s, 3H), 2.66 (m, 1H), 2.53-2.60 (m, 2H), 2.31-2.38 (m, 1H), 2.16-2.22 (m, 1H), 1.31-1.76 (m, 19H), 1.28 (d, J=6.2 Hz, 6H).

Example 7

Synthesis of Compound 219

Step A

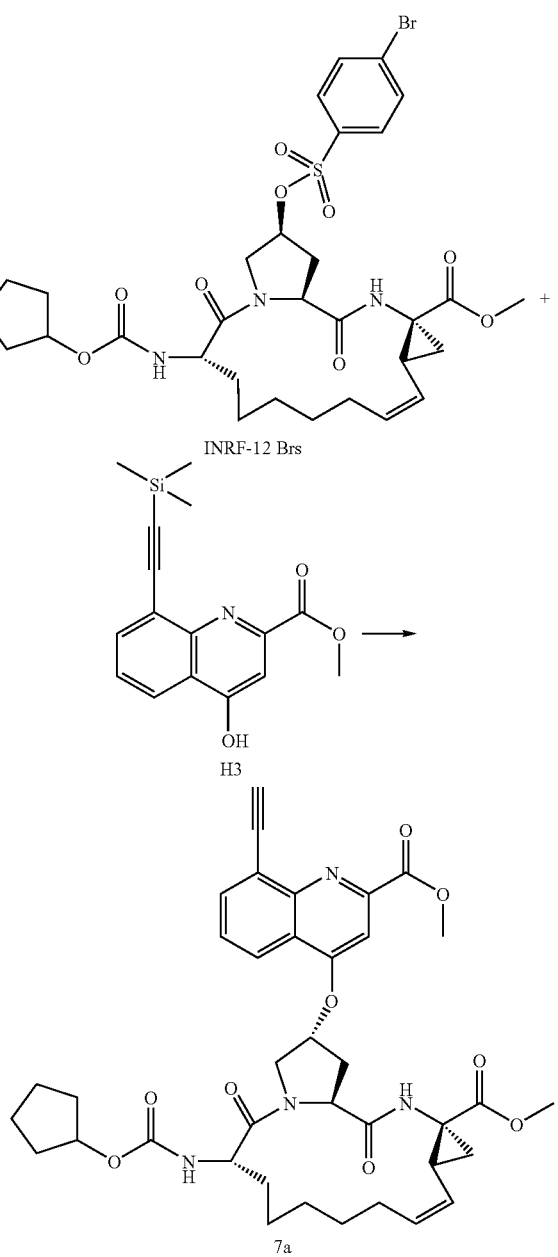

The brosylate INRF-12 Brs (914 mg, 1.29 mmol) was dissolved in NMP (10 mL) and then the quinoline H3 (360 mg, 1.20 mmol) was added followed by cesium carbonate (419 mg, 1.29 mmol). The mixture was heated at 70° C. for 14 h, cooled to RT, poured into EtOAc, and washed with H₂O, NaHCO₃, and brine. It was dried over MgSO₄, filtered and evaporated to afford compound 7a as a yellow solid (250 mg, 28%) which was employed in subsequent reactions without further purification. (ES−=699.3).

Step B

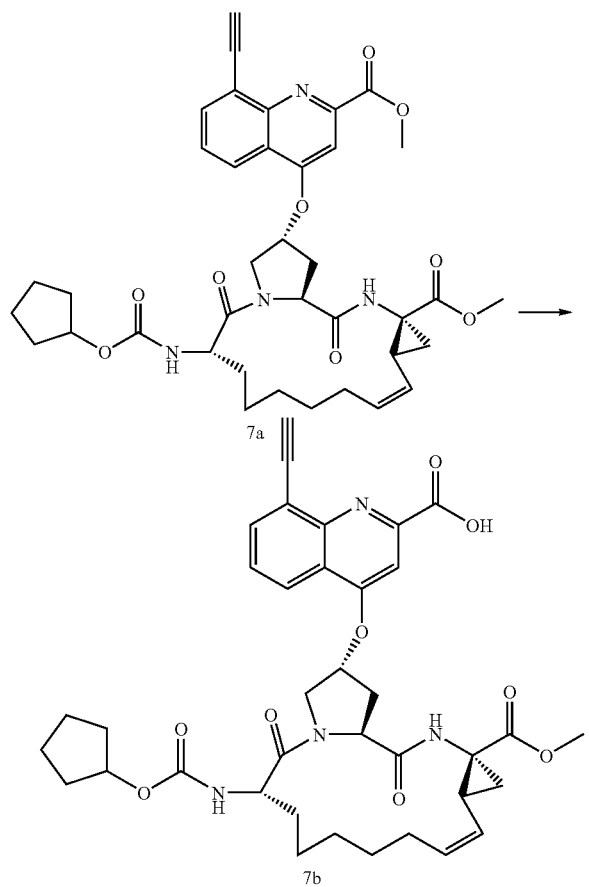

NaOH (1M, 0.7 mL, 0.7 mmol) was added to a solution of ester 7a (440 mg, 0.63 mmol) in a mixture of THF (5.7 mL)/water (1.1 mL)/MeOH (2.2 mL). The mixture was allowed to stir for 14 h at RT, concentrated and the water was azeotropically removed using benzene to yield 7b as a yellow foamy solid (RP-HPLC rt=6.03, purity 90.6%).

Step C

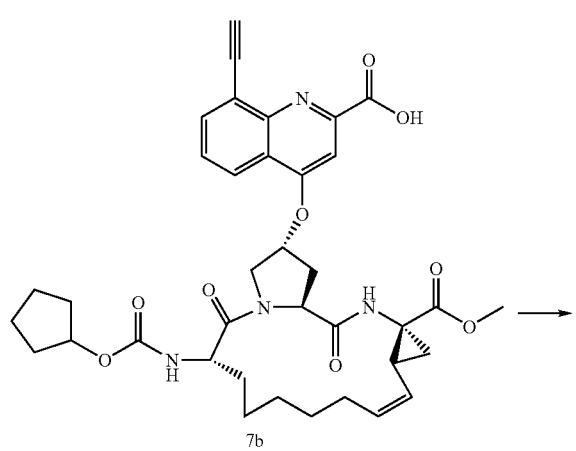

-continued

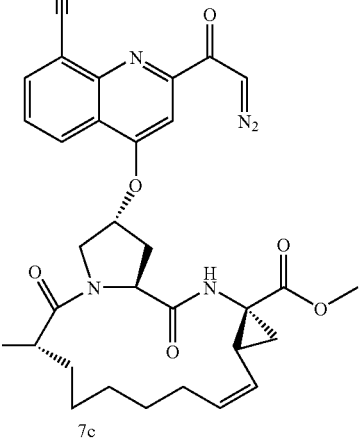

Isobutylchloroformate (0.08 mL, 0.6 mmol) was added to a solution of acid 7b (200 mg, 0.29 mmol) in THF (15 mL)/TEA (0.08 mL, 0.6 mmol) at 0° C. and the mixture was stirred for 1 h at RT. The mixture was cooled to 0° C. and diazomethane (excess) was added. The mixture was allowed to slowly warm to RT and the reaction was quenched with silica followed by $NaHCO_3$ and the mixture was extracted with EtOAc. The product 7c was employed without further purification in subsequent reactions. Yield (198 mg, 96%).

Step D

HBr (48%, 0.12 mL, 0.73 mmol) was added to a solution of diazoketone 7c (200 mg, 0.28 mmol) in THF (25 mL) at RT. The mixture was stirred for 2 h and then sodium bicarbonate (sat'd) was added and the mixture was extracted with EtOAc. The organic extract was dried filtered and concentrated and the product 7d was employed in subsequent reaction without purification. (200 mg, 93%). MS ES+=763.2.

Step E

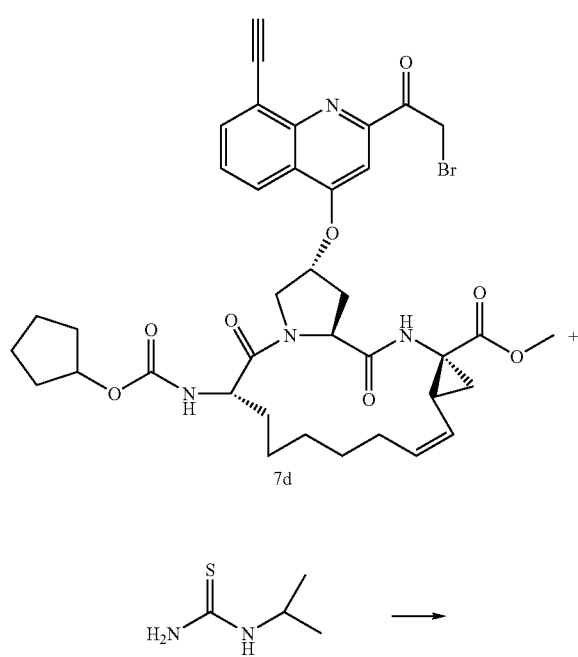

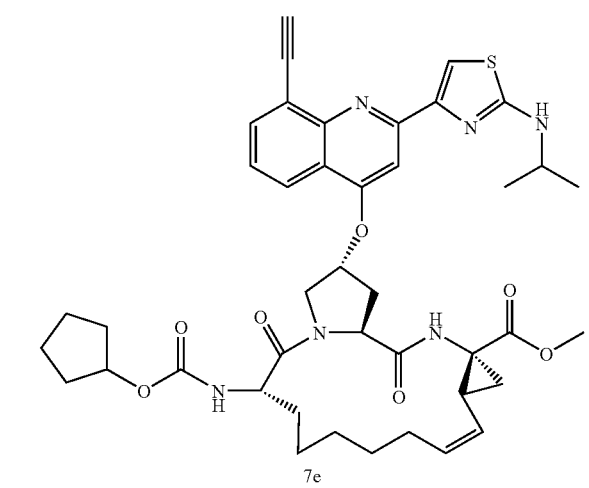

A mixture of bromo-ketone 7d (50 mg, 0.066 mmol) and isopropylthiourea (7.7 mg, 0.066 mmol) in iPrOH was heated at 70° C. for 4 h, until the reaction appeared complete by RP-HPLC and MS. The mixture was concentrated and the residue 7e was employed in subsequent reactions without further purification. MS ES+=783.3.

Step F

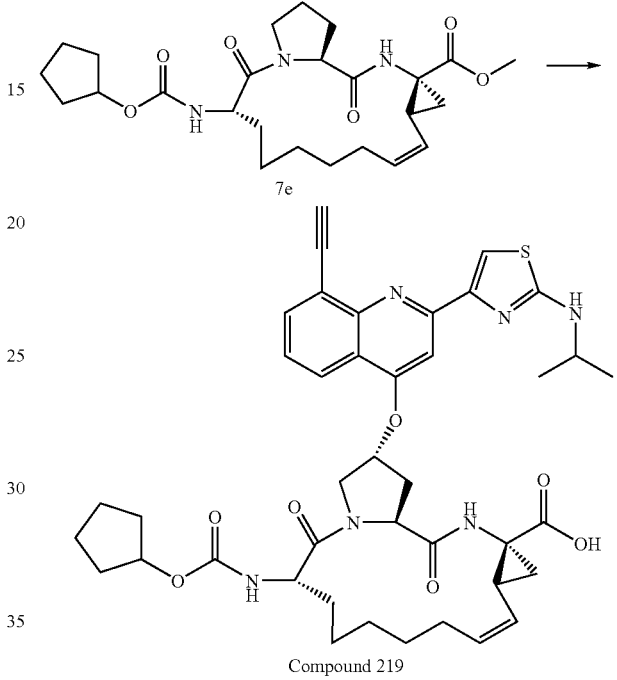

Compound 219

1M NaOH solution (0.64 mL, 0.64 mmol) was added to the starting ester 7e (50 mg, 0.064 mmol) in a THF/MeOH/water solvent mixture (2:1:1 ratio, 4 mL total volume) and the mixture was allowed to stir overnight at RT. The mixture was concentrated, diluted with DMSO and purified by prep-HPLC (H$_2$O/CH$_3$CN/0.06% TFA). The pure fractions were combined and solvents were removed by lyophilzation to obtain Compound 219 as a white solid (12 mg, 24%). MS ES+=769.3, ES−=767.3.

$^1$H NMR, 400 MHz, DMSO-d$_6$: 12.20-12.50 (br, s, 1H); 8.60 (s, 1H); 8.21 (d, J=8.2 Hz, 1H); 7.90-7.97 (m, 2H); 7.64-7.68 (m, 1H); 7.44-7.48 (m, 1H); 5.48-5.60 (m, 2H); 5.27 (t, J=9.5 Hz, 1H); 4.46-4.60 (m, 4H); 4.06-4.09 (m, 1H); 3.85-3.93 (m, 2H); 2.40-2.46 (m, 1H); 2.12-2.18 (m, 1H); 1.13-1.78 (m, 29H); RP-HPLC purity 93.8% (220 nm).

Example 8

The following compounds were made using analogous procedures to those described above using appropriate reagents.

Compound 106

$^1$H NMR (400 MHz, DMSO-d$_6$): δ 8.62 (s, 1H), 8.15 (d, J=9.0 Hz, 1H), 7.99-7.77 (m, 1H), 7.72-7.59 (m, 1H), 7.54 (br s, 1H), 7.38 (d, J=9.2 Hz, 1H), 7.21 (d, J=6.6 Hz, 1H), 5.59-5.47 (m, 2H), 5.28 (t, J=9.6 Hz, 1H), 4.58-4.40 (m, 3H), 4.11-3.85 (m, 2H), 4.01 (s, 3H), 3.80-3.40 (m, under H$_2$O, 1H), 2.59-2.45 (m, under DMSO, 2H), 2.44-2.31 (m, 1H), 2.22-2.13 (m, 1H), 1.81-1.77 (m, 19H), 1.26 (brd, J=6.2 Hz, 6H). M.S. (electrospray): 853.3 (M−H)− 853.3 (M+H)+ 855.3 (M+H)+. Reverse Phase HPLC Homogeneity (0.06% TFA; CH$_3$CN:H$_2$O): 96%

Compound 108

$^1$H NMR (400 MHz, DMSO-d$_6$): δ 12.34 (s, 1H), 8.62 (s, 1H), 8.13 (d, J=9.2 Hz, 1H), 8.04 (s, 1H), 7.50 (s, 1H), 7.41 (d, J=9.4 Hz, 1H), 7.23 (d, J=6.7 Hz, 1H), 5.57-5.46 (m, 2H), 5.28 (t, J=9.6 Hz, 1H), 4.62-4.44 (m, 3H), 4.13-4.03 (m, 1H), 4.01 (s, 3H), 3.95-3.86 (m, 1H), 2.63-2.44 (m, under DMSO, 4H), 2.43-2.36 (m, 1H), 2.24-2.13 (m, 1H), 1.82-1.20 (m, 19H), 1.13 (t, J=7.5 Hz, 3H). M.S. (electrospray): 821.2 (M−H)− 823.3 (M+H)+. Reverse Phase HPLC Homogeneity (0.06% TFA; CH$_3$CN:H$_2$O): 97%

Compound 110

$^1$H NMR (400 MHz, DMSO-d$_6$): δ 12.31 (s, 1H), 8.61 (s, 1H), 8.04 (s, 1H), 7.83 (s, 1H), 7.49 (s, 1H), 7.25 (d, J=6.3 Hz, 1H), 5.58-5.42 (m, 2H), 5.28 (t, J=9.6 Hz, 1H), 4.77-4.68 (m, 1H), 4.57-4.41 (m, 2H), 4.18-3.90 (m, under H$_2$O, 2H), 3.77 (s, 3H), 2.67 (s, 3H), 2.58-2.44 (m, under DMSO, 4H), 2.40 (s, 3H), 2.42-2.31 (m, 1H), 2.24-2.14 (m, 1H), 1.83-1.15 (m, 19H), 1.13 (t, J=7.5 Hz, 3H). M.S. (electrospray): 815.3 (M−H)− 817.4 (M+H)+. Reverse Phase HPLC Homogeneity (0.06% TFA; CH$_3$CN:H$_2$O): 99%

Compound 112

$^1$H NMR (400 MHz, DMSO-d$_6$): δ 12.36 (s, 1H), 8.62 (s, 1H), 8.04 (s, 1H), 7.94 (d, J=9.2 Hz, 1H), 7.49 (s, 1H), 7.40 (t, J=8.4 Hz, 1H), 7.24 (d, J=6.6 Hz, 1H), 5.57-5.46 (m, 2H), 5.28 (t, J=9.6 Hz, 1H), 4.61-4.52 (m, 2H), 4.51-4.43 (m, 1H), 4.14-3.87 (m, under H$_2$O, 2H), 3.99 (s, 3H), 2.62-2.44 (m, under DMSO, 4H), 2.43-2.31 (m, 1H), 2.24-2.14 (m, 1H), 1.82-1.15 (m, 19H), 1.12 (t, J=7.5 Hz, 3H). M.S. (electrospray): 805.2 (M−H)− 807.3 (M+H)+. Reverse Phase HPLC Homogeneity (0.06% TFA; CH$_3$CN:H$_2$O): 99%

Compound 202

$^1$HNMR (400 MHz, DMSO-d$_6$)-12.31 (s, 1H); 8.60 (s, 1H); 7.96 (s, 1H); 7.90 (s, J=8 Hz, 1H); 7.55 (s, 1H); 7.45-7.37 (m, 2H); 7.25 (d, J=7 Hz, 1H); 5.5-5.43 (m, 3H); 5.3-5.23 (m, 2H); 4.65-4.54 (m, 2H); 4.15-4.05 (m, 1H); 3.95-3.87 (m, 1H); 2.55 (m, 3H, under DMSO-d6 signal); 2.40-2.14 (m, 3H); 1.84-1.05 (m, 30H). MS (ESI) (M+H)=859.5; (M−H)=857.4

Compound 207

$^1$H NMR (400 MHz, DMSO-d$_6$)-11.88 (s, 1H), 8.59 (s, 1H), 7.92 (s, 1H), 7.90 (d, J=8 Hz, 1H), 7.53 (s, 1H), 7.44-7.36 (m, 2H), 7.25 (d, J=7 Hz, 1H), 5.54-5.45 (m, 2H), 5.29-5.24 (m, 1H), 5.02-4.93 (m, 2H), 4.65-4.55 (m, 3H), 4.50-4.38 (m, 1H), 3.95-3.85 (m, 1H), 2.55 (s, 3H, under DMSO signal), 2.38-2.32 (m, 1H), 2.21-2.15 (m, 1H), 1.80-1.30 (m, 20H), 1.28 (d, J=6 Hz, 6H). MS (ESI) (M+H)=835.4 (M−H)=833.3.

Compound 214

M.S. (electrospray): 815.4 (M−H)$^−$ 813.4 (M+H)$^+$. Reverse Phase HPLC Homogeneity @ 220 nm (0.06% TFA; CH$_3$CN:H$_2$O): 98.9%. $^1$H NMR (400 MHz, DMSO-d$_6$): δ 12.28 (s, 1H), 8.60 (s, 1H), 8.02-8.06 (m, 2H), 7.60 (d, J=6.6 Hz, 1H), 7.56 (s, 1H), 7.33 (t, J=7.6 Hz, 1H), 7.26 (d, J=6.6 Hz, 1H), 5.47-5.53 (m, 2H), 5.24-5.29 (m, 1H), 4.56-4.64 (m, 2H), 4.42-4.46 (m, 1H), 4.09-4.4.13 (m, 1H), 3.90-3.93 (m, 1H), 2.75 (s, 3H), 2.53-2.59 (m, 2H), 2.32-2.40 (m, 3H), 2.16-2.24 (m, 1H), 1.16-1.75 (m, 20H), 1.03 (s, 9H).

Example 9

Synthesis of Sulfonamide Fragments 9d and 9g

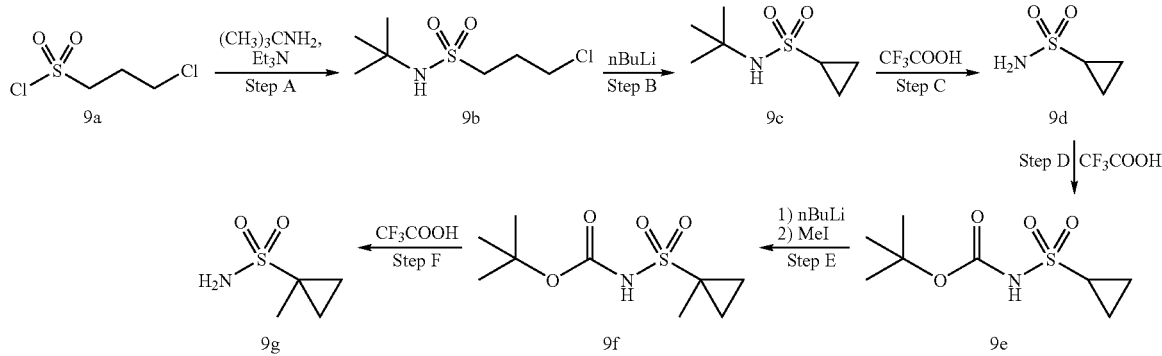

Step A

A dry 3 L 3-neck flask equipped with a magnetic stir bar, addition funnel and argon inlet was flushed with argon, then charged with 3-chloropropanesulfonyl chloride 9a (100.48 g, 0.57 mol, 1.0 eq). Anhydrous dichloromethane (900 mL) was transferred into the flask via cannula, the mixture was cooled in an ice/water bath and tert-butylamine (72 mL, 0.68 mol, 1.2 eq) was added. The mixture was stirred 15 minutes then a solution of triethylamine (158 mL, 1.13 mol, 2.0 eq) in anhydrous dichloromethane (100 mL) was added dropwise over 45 minutes and stirring was continued for 1 h. The mixture was diluted with dichloromethane (500 mL) and washed with 1N HCl (3×400 ml) and brine. The organic layer was dried over sodium sulfate, filtered and evaporated to dryness to give compound 9b as an orange-beige solid (107.04 g, 88% yield). $^1$H NMR (CDCl$_3$, 400 MHz): δ 4.46 (s, 1H), 3.71 (tr, 2H), 3.25 (tr, 2H), 2.31 (m, 2H), 1.41 (s, 9H).

Step B

A dry 5 L 3-neck flask equipped with a magnetic stir bar, argon inlet and 2 addition funnels was flushed with argon and anhydrous THF (1.5 L) was transferred into the flask via cannula and cooled to −78° C. Compound 9b (96.73 g, 0.453 mol, 1.0 eq) was dissolved in anhydrous THF (390 mL) and the solution was transferred into one of the addition funnels. n-Butyllithium solution (2.5 M in hexanes, 390 mL, 0.975 mol, 2.15 eq) was transferred to the other addition funnel and the solutions in the addition funnels were added to the flask simultaneously over 4 hours. When addition was complete, the mixture was allowed to warm to room temperature. Once the internal temperature reached~0° C., the reaction was quenched by dropwise addition of saturated $NH_4Cl$ solution (200 mL). The THF was removed under vacuum and the residue was diluted with $CH_2Cl_2$ (2 L) and water (1 L). The layers were separated and the organic layer was washed with water (2×1 L) and brine (800 mL), dried over sodium sulfate, filtered and evaporated to dryness. Compound 9c was obtained as an orange-beige solid (77.32 g, 96% yield). $^1$H NMR ($CDCl_3$, 400 MHz): δ 4.25 (s, 1H), 2.48 (m, 1H), 1.42 (s, 9H), 1.19 (m), 1.01 (m).

Step C

A 2 L flask equipped with a magnetic stir bar and condenser was charged with Compound 9c (82.53 g, 0.466 mol, 1.0 eq), dichloromethane (400 mL) and trifluoroacetic acid (460 mL, 5.97 mol, 13 eq). The mixture was heated to reflux for 2 h, allowed to cool, and evaporated and co-evaporated several times with $CH_2Cl_2$ to remove most of the TFA. The crude product was dissolved in 95:5 $CH_2Cl_2$:MeOH and $NH_4OH$ and was purified by silica gel column chromatography (94:5:1 $CH_2Cl_2$:MeOH:$NH_4OH$). Compound 9d was obtained as a beige solid (46.38 g, 78% yield). $^1$H NMR (DMSO-$d_6$, 400 MHz): δ 6.79 (s, 2H), 2.54 (1H, under DMSO peak), 0.92 (4H).

Step D

To the solid cyclopropanesulfonamide 9d (1.51 g; 12.46 mmol) was added in sequence: di-t-butyl-dicarbonate (3.26 g; 14.95 mmol) dissolved in anhydrous dichloromethane (15 mL), triethylamine (2.6 mL; 18.65 mmol) and dimethylaminopyridine (76 mg; 0.622 mmol). The resulting solution was stirred at room temperature overnight and subsequently evaporated to near dryness. The residue was diluted with EtOAc, washed with 1N aq. HCl (3×) and brine (1×), dried ($MgSO_4$), filtered and evaporated to dryness to provide the Boc-cyclopropylsulfonamide product 9e as a white solid (2.6 g; 94%).

Step E

To a cooled solution (−78° C.) of the Boc-cyclopropanesulfonamide 9e (500 mg; 2.26 mmol) in anhydrous THF (15 mL) was added dropwise n-BuLi (2.1 mL; 5.20 mmol) and the mixture was allowed to stir 1 h at −78° C. Two portions of methyl iodide (each 280 μL; 4.52 mmol) were added with a one hour interval and the reaction mixture was allowed to warm slowly to RT and stir at RT overnight. The reaction mixture was adjusted to pH 3 with 1N aq. HCl and the product was extracted with EtOAc (3×). The combined EtOAc extracts were washed with brine (1×), dried ($MgSO_4$), filtered and evaporated to dryness to provide the crude alkylated product 9f as a light yellow oil. The crude material was purified by flash chromatography over silica gel with hexane:EtOAc (9:1) as eluent to provide pure product as a yellow oil (151.8 mg; 29%).

Step F

To a solution of the Boc-1-methylcyclopropanesulfonamide 9f (151.8 mg: 0.65 mmol) in dichloromethane (6 mL) was added trifluroacetic acid (6 mL) and the mixture allowed to stir at RT for 3.5 h. Evaporation to dryness under high vacuum provided the deprotected material 9g as an off-white wax like solid (79.1 mg, 91%).

$^1$H NMR ($CDCl_3$, 400 MHz): δ 4.56 (s, 2H), 1.58 (s, 3H), 1.43-1.38 (m, 2H), 0.85-0.80 (2H).

Example 10

Synthesis of Compound 301

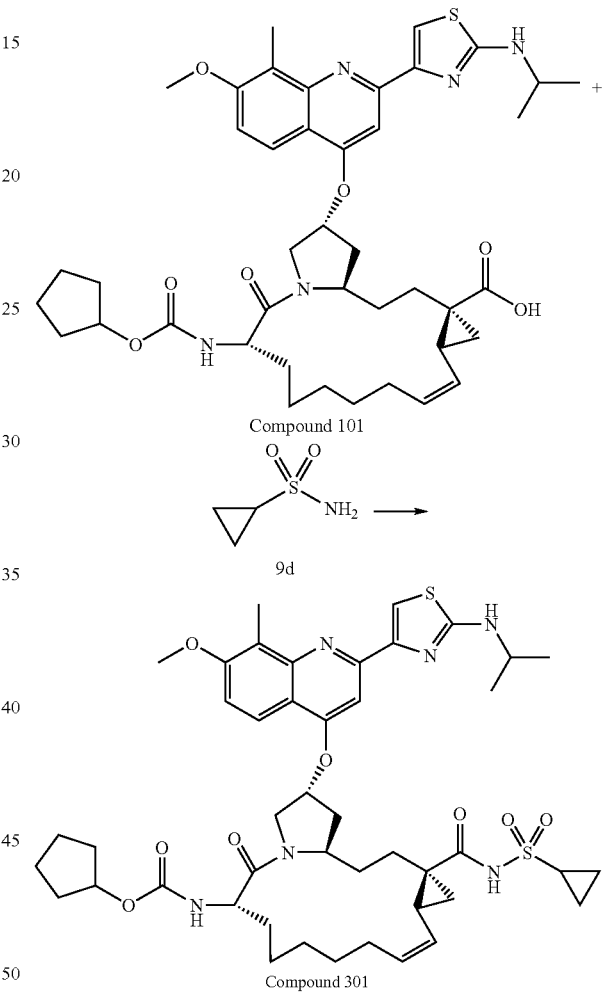

To the acid (compound 101, Example 3) (125 mg; 0.16 mmol) dissolved in anhydrous DMF (4 mL) was added HATU reagent (72.1 mg; 0.63 mmol) followed by a dropwise addition of DIPEA (138 μL; 0.79 mmol). The colourless solution was stirred at RT for 1 hour (Analytical HPLC indicated complete conversion to the activated ester) and the cyclopropylsulfonamide 9d (Example 7) (76.6 mg; 0.63 mmol) was added, followed in 5 minutes by a dropwise addition of DBU (94.5 μL, 0.63 mmol). The reaction mixture was allowed to stir at RT overnight. Analytical HPLC indicated near complete conversion to product. No work up was performed, the crude reaction mixture was purified by preparatory HPLC (Reverse phase: YMC, Combiscreen ODS-AQ, 50×20 mm ID S-5 micron, 120A; λ=220 nm) using a linear gradient and 0.06% TFA $CH_3CN/H_2O$ from 6-100% $CH_3CN$.

The fractions were analyzed by analytical HPLC (Reverse phase: YMC, Combiscreen ODS-AQ, 50×4.6 mm ID S-5 micron, 120A; λ=220 nm), pure fractions were combined, concentrated and lyophilized to provide compound 301 as a bright yellow amorphous solid (64.7 mg; 46% yield). Reverse Phase HPLC Homogeneity (0.06% TFA; $CH_3CN:H_2O$): 99%. M.S. 892.5 $(M+H)^+$ $^1$H NMR (DMSO-$d_6$): δ 11.1 (s, 1H), 8.86 (s, 1H), 8.13-8.08 (m, 2H), 7.65-7.55 (m, 1H), 7.45-7.32 (m, 2H), 5.68-5.54 (m, 2H), 5.11 (dd, J=9.2, 18.8 Hz, 1H), 4.67 (d, J=11.1 Hz, 1H), 4.54-4.45 (m, 1H), 4.43 (dd, J=8.0, 16.8 Hz, 1H), 4.09-4.00 (m, 1H), 3.96 (s, 3H), 3.95-3.81 (m, 3H), 2.95-2.85 (m, 1H), 2.75-2.60 (m, 2H), 2.55 (s, 3H), 2.44-2.26 (m, 3H), 1.76-0.95 (m, 21H), 1.26 (d, J=5.7 Hz, 6H).

Example 11

Synthesis of Compound 302

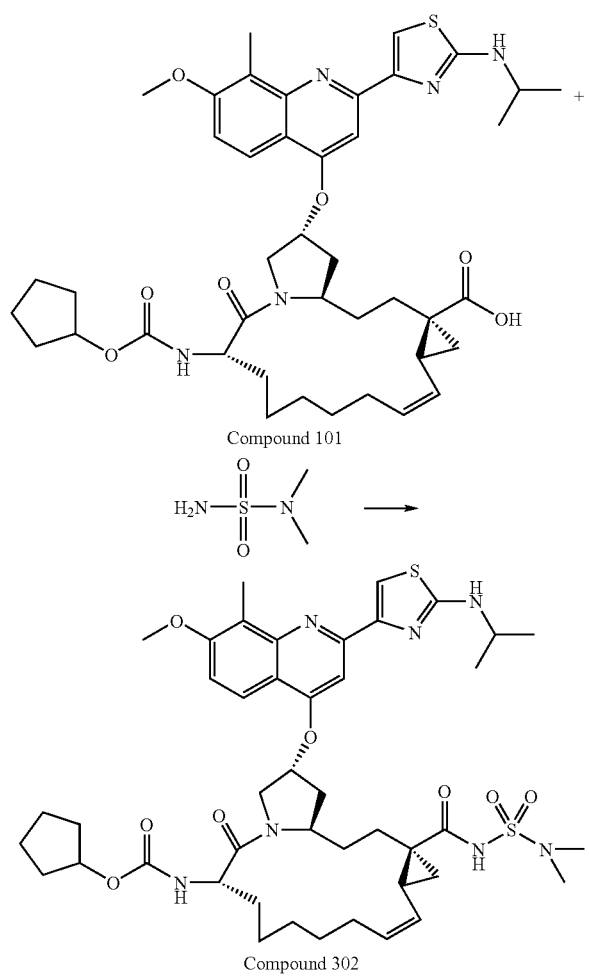

Compound 101

Compound 302

The acid (compound 101, Example 3) (100 mg, 0.127 mmol), N,N-dimethylsulfamide (18.9 mg, 0.152 mmol), and DIPEA (0.132 mL, 0.762 mmol) were dissolved in DMF (4 mL) and to the mixture was added DBU (0.076 mL, 0.51 mmol).

The mixture was stirred for 5 min, then HATU (58 mg, 0.152 mmol) was added and stirring was continued for 12 h. The reaction mixture was concentrated and the residue was dissolved in AcOH, purified by preparatory HPLC (YMC Combiscreen ODS-AQ, 50×20 mm ID S-5 micron, 120A; 220 nm) using a linear gradient and 0.06% TFA $CH_3CN/H_2O$. The pure fractions were combined, concentrated and lyophilized to provide the product compound 302 as the TF salt (13.2 mg, 11.6%).

$^1$H NMR(400 MHz, DMSO-$d_6$): δ 10.80 (s, 1H), 8.91 (s, 1H), 8.09 (d, J=8 Hz, 1H), 7.63 (brs, 1H), 7.40 (d, J=6.5 Hz, 1H), 7.35 (brs, 1H), 5.54-5.50 (m, 2H), 5.07 (t, J=9 Hz, 1H), 4.68 (d, J~8 Hz, 1H), 4.51-4.47 (m, 2H), 4.10-3.80 (m, 5H), 2.72 (s, 6H), 2.69-2.65 (m, 1H), 2.55 (s, 3H), 2.44-2.35 (m, 1H), 2.32-2.25 (m, 1H), 1.80-1.10 (m, 29H) EIMS: (M+H)=895.6 (M−H)=893.5

Example 12

NS3-NS4A Protease Assay

The enzymatic assay used to evaluate the present compounds is described in WO 00/09543 and WO 00/59929.

Example 13

Cell-Based Luciferase Reporter HCV RNA Replication Assay

Cell Culture:

Huh-7 cells with a stable subgenomic HCV replicon that encodes a modified luciferase reporter gene (expressed as a luciferase-FMDV2A-neomycin phosphotransferase fusion gene) were established as previously described (Lohman et al., 1999. Science 285: 110-113; Vroljik et al., 2003 J. Virol Methods 110:201-209.), with the exception that replicon cells were selected with 0.25 mg/ml G418.

The amount of luciferase expressed by selected cells directly correlates with the level of HCV replication. These cells, designated as MP-1 cells, are maintained in Dulbecco's Modified Earle Medium (DMEM) supplemented with 10% FBS and 0.25 mg/ml neomycin (standard medium). The cells are passaged by trypsinization and frozen in 90% FBS/10% DMSO. During the assay, DMEM medium supplemented with 10% FBS, containing 0.5% DMSO and lacking neomycin, was used (Assay medium). The day of the assay, MP-1 cells are trypsinized and diluted to 100 000 cells/ml in assay medium. 100 μL is distributed into each well of a black 96-well ViewPlate™ (Packard). The plate is then incubated at 37° C. with 5% $CO_2$ for two hours.

| Reagents and Materials: | | | |
|---|---|---|---|
| Product | Company | Catalog # | Storage |
| DMEM | Wisent Inc. | 10013CV | 4° C. |
| DMSO | Sigma | D-2650 | RT |
| Dulbecco's PBS | Gibco-BRL | 14190-136 | RT |
| Fetal Bovine Serum | Bio-Whittaker | 14-901F | −20° C./4° C. |
| Geneticin (G418) | Gibco-BRL | 10131-027 | −20° C./4° C. |
| Trypsin-EDTA | Gibco-BRL | 25300-054 | −20° C./4° C. |
| ViewPlate ™-96, Black | Packard | 6005182 | RT |
| Backing tape, Black | Packard | 6005189 | RT |
| PVDF 0.22 μm Filter Unit | Millipore | SLGV025LS | RT |
| Deep-Well Titer Plate Polypropylene | Beckman | 267007 | RT |

Preparation of Test Compound:

The test compound in 100% DMSO was first diluted in assay medium to a final DMSO concentration of 0.5%. The solution was sonicated for 15 min and filtered through a 0.22 µM Millipore Filter unit. Into column 3 of a Polypropylene Deep-Well Titer Plate, the appropriate volume is transferred into assay medium to obtain the starting concentration (2×) to be tested. In columns 2 and 4 to 12, add 200 µL of assay medium (containing 0.5% DMSO). Serial dilutions (1/2) are prepared by transferring 200 µL from column 3 to column 4, then from column 4 to column 5, serially through to column 11. Columns 2 and 12 are the no inhibition controls.

Addition of Test Compound to Cells:

A volume of 100 µL from each well of the compound dilution plate is transferred to a corresponding well of the Cell Plate (Two columns will be used as the "No inhibition control"; ten [10] columns are used for the dose response). The cell culture plate was incubated at 37° C. with 5% $CO_2$ for 72 hours.

Luciferase Assay:

Following the 72 h incubation period, the medium is aspirated from the 96-well assay plate and a volume of 100 µL of 1×Glo Lysis Buffer (Promega) previously warmed to room temperature was added to each well. The plate was incubated at room temperature for 10 min with occasional shaking. A black tape was put at the bottom of the plate. 100 µL of Bright-Glo luciferase substrate (Promega) previously warmed to room temperature was added to each well followed by gentle mixing. The luminescence was determined on a Packard Topcount instrument using the Data Mode Luminescence (CPS) with a count delay of 1 min and a count time of 2 sec.

| Product | Company | Catalog # | Storage |
|---|---|---|---|
| Glo Lysis Buffer | Promega | E266A | 4° C. |
| Bright-Glo Luciferase Assay System | Promega | E2620 | −20° C. |

The luminescence determination (CPS) in each well of the culture plate was a measure of the amount of HCV RNA replication in the presence of various concentrations of inhibitor. The % inhibition was calculated with the following equation:

% inhibition=100-[*CPS*(inhibitor)/*CPS*(control)×100]

A non-linear curve fit with the Hill model was applied to the inhibition-concentration data, and the 50% effective concentration ($EC_{50}$) was calculated by the use of SAS software (Statistical Software; SAS Institute, Inc. Cary, N.C.).

Example 14

Specificity Assays

The specificity assays used to evaluate the selectivity of this compound are described in WO 00/09543.

When the compounds are evaluated in the specificity assays, the compounds of formula 1 are found to be selective in that they do not show significant inhibition in the Human Leukocyte Elastase and Cathepsin B assays.

Example 15

Pharmacokinetic Properties

The present invention comprises compounds that show pharmacokinetic properties such as detectable plasma levels in the rat at 1 hour and 2 h after an oral dose of 5 mg/kg.

More explicitly, the following assay, an in vivo oral absorption screen, is used to determine plasma levels of test compounds in a rat after oral administration:

Materials and Methods:

1. Method Used to Pool Compounds ("Cassette Selection"):

The selection of compounds to be pooled into a "cassette" was based on their structural similarity and physicochemical properties. A solid phase extraction method applicable to all the selected compounds was established. Based on the initial testing where each compound was spiked into rat plasma and run through HPLC or HPLC/MS at a concentration of 0.5 µM, the retention time, ionic mass, and the possible separation among compounds by HPLC and/or HPLC/MS were used as basis for pooling 3-4 compounds into one "cassette".

2. Oral Vehicle and Compound Preparation:

Each "cassette" contains 34 compounds at 5 or 4 mg/kg for each compound. The cassettes were prepared as an oral suspension in 0.5% aqueous methylcellulose and 0.3% of polyoxyethylene (20) sorbiton monooleate (Tween-80). The dosing volume was 10 mL/kg via oral gavage.

3. Dosing and Plasma Sampling:

Male Sprague Dawley rats were fasted overnight in individual cages, with access to aqueous 10% dextrose. Two rats were dosed with each "cassette". Plasma samples (~1 mL) were collected at 1 and 2 h post-dosing from the 2 rats and pooled for extraction and analysis.

4. Compound Extraction and Analysis:

From each cassette, plasma samples at 1 and 2 h, blank plasma, blank plasma spiked with all the compounds at 0.5 µM of each, are extracted by the solid phase extraction method. Samples were analyzed by HPLC and HPLC/MS for comparison purpose. Plasma concentrations are estimated based on the single concentration of 0.5 µM standard.

Results

When assayed in the preceding screen, some compounds of this invention are found in the plasma at the 1 hour and 2 hour intervals following oral administration, with blood plasma levels up to 3.5 µM.

Tables and Compounds

Compounds according to this invention and presented in Tables 1 to 3 usually show $IC_{50}$ values equal or lower than about 50 nM and $EC_{50}$ values equal or lower than about 55 nM.

TABLE 1
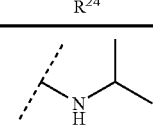
| Cpd # | L² | L⁰ | L¹ | R²⁴ | MS (M + H)⁺ |
|---|---|---|---|---|---|
| 101 | H | —OMe | Me | 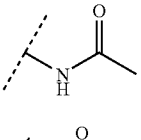 | 789.4 |
| 102 | H | —OMe | Me | 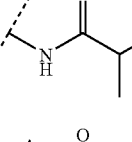 | 789.3 |
| 103 | H | —OMe | Me | 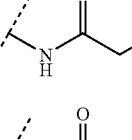 | 817.4 |
| 104 | H | —OMe | Me | 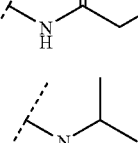 | 803.4 |
| 105 | H | —OMe | Br | 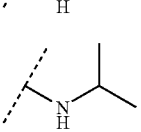 | 867.3 869.3 |
| 106 | H | —OMe | Br | 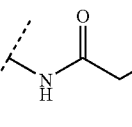 | 853.3 855.3 |
| 107 | H | —OMe | Cl | 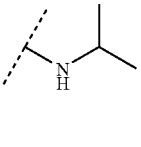 | 809.3 811.3 |
| 108 | H | —OMe | Cl |  | 823.3 825.3 |
| 109 | Me | —OMe | Me | 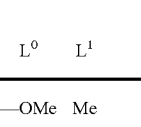 | 803.4 |
TABLE 1-continued
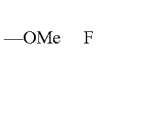
| Cpd # | L² | L⁰ | L¹ | R²⁴ | MS (M + H)⁺ |
|---|---|---|---|---|---|
| 110 | Me | —OMe | Me | 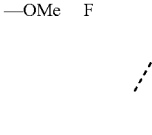 | 817.4 |
| 111 | H | —OMe | F | 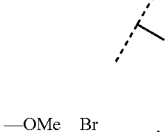 | 793.4 |
| 112 | H | —OMe | F | 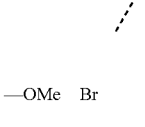 | 807.3 |
| 113 | H | —OMe | Cl | | 837.3 839.2 |
| 114 | H | —OMe | Br | | 881.2 883.2 |
| 115 | H | —OMe | Br | 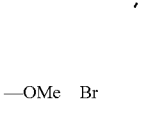 | 881.2 883.2 |
| 116 | H | —OMe | Br | 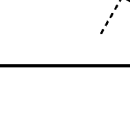 | 897.2 899.2 |

TABLE 2
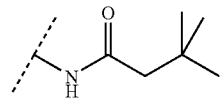
| Cpd # | L¹ | R²⁴ | MS (M + H)⁺ |
|---|---|---|---|
| 201 | —SMe | 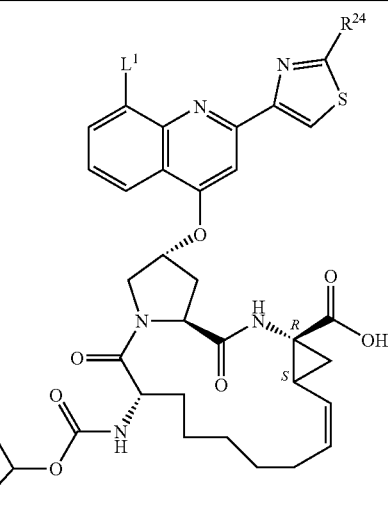 | 845.3 (M − H)⁻ |
| 202 | —SMe | 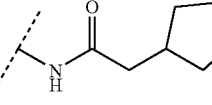 | 859.5 |
| 203 | —SMe | 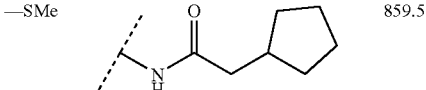 | 805.4 |
| 204 | —SMe | 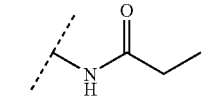 | 791.3 |
| 205 | —SMe | 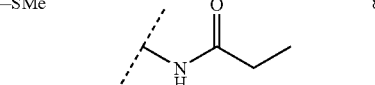 | 819.3 |
| 206 | —SMe | 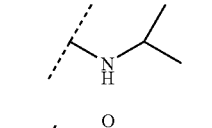 | 819.3 |
| 207 | —SMe | 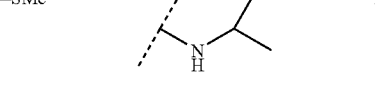 | 835.4 |
| 208 | —SO₂Me | 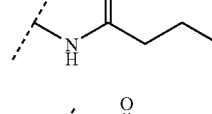 | 837.3 |
| 209 | —SO₂Me | 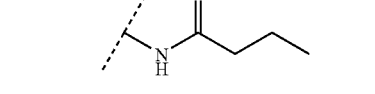 | 823.3 |
TABLE 2-continued
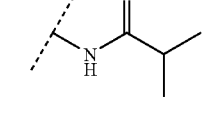
| Cpd # | L¹ | R²⁴ | MS (M + H)⁺ |
|---|---|---|---|
| 210 | —SO₂Me | 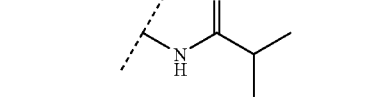 | 851.3 |
| 211 | —SO₂Me | 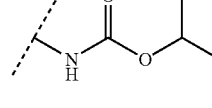 | 867.3 |
| 212 | —Me | 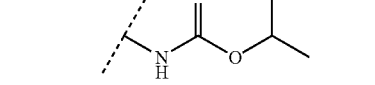 | 759.3 |
| 213 | —Me | 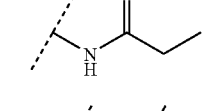 | 773.3 |
| 214 | —Me | 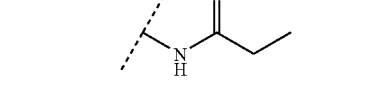 | 815.4 |
| 215 | —Me | 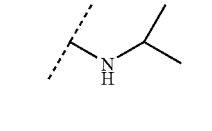 | 787.4 |
| 216 | —Me | 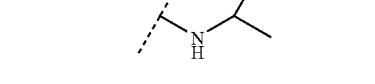 | 803.4 |
| 217 | 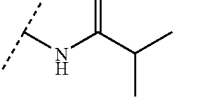 | 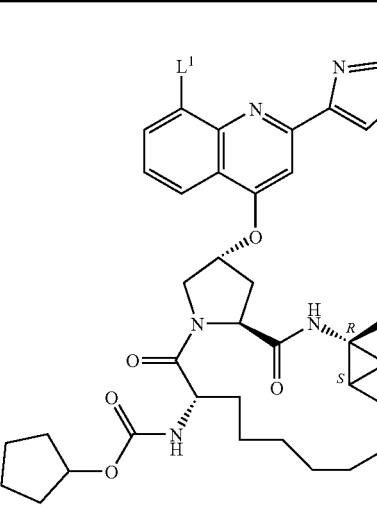 | 797.4 |

TABLE 2-continued

| Cpd # | L¹ | R²⁴ | MS (M + H)⁺ |
|---|---|---|---|
| 218 | propargyl | -NH-C(O)-ethyl | 783.3 |
| 219 | propargyl | -NH-isopropyl | 769.3 |
| 220 | propargyl | -NH-C(O)-CH₂-tBu | 825.4 |

TABLE 3

| Cpd # | R$^S$ | MS (M + H)⁺ |
|---|---|---|
| 301 | cyclopropylmethyl | 892.5 |

TABLE 3-continued

| Cpd # | R$^S$ | MS (M + H)⁺ |
|---|---|---|
| 302 | -CH₂-N(CH₃)₂ | 896.6 |
| 303 | 1-methylcyclopropylmethyl | 906.5 |

What is claimed is:

1. A compound of formula I:

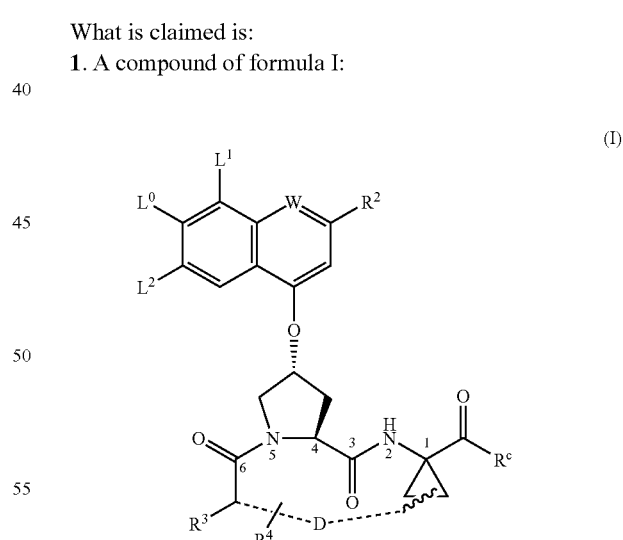

(I)

wherein W is CH or N,

L⁰ is —OH, —O—($C_{1-4}$)alkyl, —NH₂, —NH($C_{1-4}$)alkyl or —N(($C_{1-4}$)alkyl)₂;

L¹, L² are each independently halogen, ($C_{1-4}$)alkyl, —O—($C_{1-4}$)alkyl, —S—($C_{1-4}$)alkyl, —SO—($C_{1-4}$)alkyl, or —SO₂—($C_{1-4}$)alkyl; and either L¹ or L² (but not both at the same time) may also be H; or $L^0$ and $L^1$ or $L^0$ and $L^2$ may be covalently bonded to form, together with the two C-atoms to which they are linked, a 4-, 5- or 6-membered carbocyclic ring wherein one —CH$_2$- group and, in the case of 5- or 6-membered ring, one or two —CH$_2$-groups not being directly linked to each other, may be replaced each independently by —O— or NR$^a$ to form a heterocyclic ring wherein R$^a$ is H or (C$_{1-4}$)alkyl, and wherein said carbo- or heterocyclic ring is optionally mono- or di-substituted with (C$_{1-4}$)alkyl;

R$^2$ is (C$_{6\,or\,10}$)aryl or Het, wherein Het is a five-, six-, or seven-membered, saturated or unsaturated (including aromatic) heterocycle, containing from one to four heteroatoms each independently selected from nitrogen, oxygen and sulfur, said aryl or Het being substituted with R$^{24}$, wherein R$^{24}$ is H, halo, (C$_{1-6}$)alkoxy, (C$_{3-6}$)cycloalkoxy or NO$_2$; or R$^{24}$ is R$^{20}$, —NHCOR$^{20}$, —NHCOOR$^{20}$, —NHR$^{21}$ or —NHCONR$^{21}$R$^{22}$, wherein R$^{20}$ is selected from (C$_{1-8}$)alkyl, (C$_{3-7}$)cycloalkyl and (C$_{1-4}$)alkyl-(C$_{3-7}$)cycloalkyl, wherein said cycloalkyl and alkyl-cycloalkyl may be mono-, di- or tri-substituted with (C$_{1-3}$)alkyl;

R$^{21}$ is H or as defined above; and

R$^{22}$ is H or methyl;

R$^3$ is hydroxy, NH$_2$, or a group of formula —NH—R$^{31}$, wherein R$^{31}$ is (C$_{6\,or\,10}$)aryl, heteroaryl, —C(O)—B, —C(O)—OB, or —C(O)—NH—B, wherein B is (C$_{1-10}$)alkyl, (C$_{3-7}$)cycloalkyl or (C$_{1-4}$)alkyl-(C$_{3-7}$)cycloalkyl, a) wherein each said cycloalkyl, and alkyl-cycloalkyl may be mono-, di- or tri-substituted with (C$_{1-3}$)alkyl; and b) wherein each said alkyl, cycloalkyl, and alkyl-cycloalkyl may be mono- or di-substituted with substituents each independently selected from hydroxy and O—(C$_{1-6}$)alkyl; and c) wherein each of said alkyl groups may be mono-, di- or tri-substituted with halogen; and d) wherein in each of said cycloalkyl groups being 5-, 6- or 7-membered, one or two —CH$_2$-groups not being directly linked to each other may be replaced by —O—;

D is a 5 to 10-atom saturated or unsaturated alkylene chain optionally containing one to three heteroatoms each independently selected from: O, S, and N—R$^{41}$, wherein R$^{41}$ is H, (C$_{1-6}$)alkyl, (C$_{3-6}$)cycloalkyl, or —C(O)—R$^{42}$, wherein R$^{42}$ is (C$_{1-6}$)alkyl, (C$_{3-6}$)cycloalkyl or (C$_{6\,or\,10}$)aryl;

R$^4$ is H or from one to three substituents at any carbon atom of said chain D, said substituents each independently selected from the group consisting of: (C$_{1-6}$)alkyl, (C$_{1-6}$)haloalkyl, (C$_{1-6}$)alkoxy, hydroxy, halo, amino, oxo, thio, and (C$_{1-6}$)alkylthio;

and

R$^C$ is hydroxy or —NHSO$_2$R$^S$ wherein R$^S$ is (C$_{1-6}$)alkyl, (C$_{3-7}$)cycloalkyl, (C$_{1-6}$)alkyl-(C$_{3-7}$)cycloalkyl, phenyl, naphthyl, pyridinyl, (C$_{1-4}$)alkyl-phenyl, (C$_{1-4}$)alkyl-naphthyl or (C$_{1-4}$)alkyl-pyridinyl; each of which optionally being monosubstituted with nitro; and each of which optionally being mono-, di- or tri-substituted with substituents each independently selected from halogen, hydroxy, cyano, (C$_{1-4}$)alkyl, O—(C$_{1-6}$)alkyl, —CO—NH$_2$, —CO—NH(C$_{1-4}$)alkyl, —CO—N((C$_{1-4}$)alkyl)$_2$, —NH$_2$, —NH(C$_{1-4}$)alkyl and —N((C$_{1-4}$)alkyl)$_2$;

or R$^S$ is —NH(C$_{1-6}$)alkyl), N(C$_{1-6}$alkyl)$_2$, -Het, or a pharmaceutically acceptable salt or ester thereof.

2. The compound according to claim 1 wherein R$^3$ is selected from NH—C(O)—B, NH—C(O)—NH—B, and NH—C(O)—O—B, wherein B is defined as in claim 1.

3. The compound according to claim 1 wherein D is a 7-carbon alkylene chain containing one cis double bond at position 13,14 of the chain.

4. The compound according to claim 1 of formula (I')

(I')

wherein:

X is O or NH; and B, L$^0$, L$^1$, L$^2$, R$^2$ and R$^C$ are defined as in claim 1.

5. The compound according to claim 4 wherein R$^2$ is phenyl or Het, wherein said Het is selected from the group consisting of:

wherein R$^{24}$ is H, halo, (C$_{1-6}$)alkoxy, (C$_{3-6}$)cycloalkoxy or NO$_2$; or R²⁴ is R²⁰, —NHCOR²⁰, —NHCOOR²⁰, —NHR²¹ or —NHCONR²¹R²², wherein
R²⁰ is selected from $(C_{1-8})$alkyl, $(C_{3-7})$cycloalkyl and $(C_{1-4})$alkyl-$(C_{3-7})$cycloalkyl, wherein said cycloalkyl and alkyl-cycloalkyl may be mono-, di- or tri-substituted with $(C_{1-3})$alkyl;
R²¹ is H or as defined above; and
R²² is H or methyl.

6. The compound according to claim 5 wherein R² is Het, wherein said Het is selected from the group consisting of:

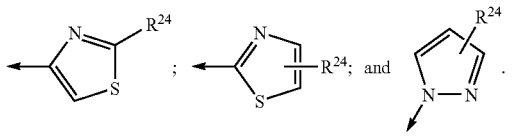

7. The compound according to claim 1 of formula IA

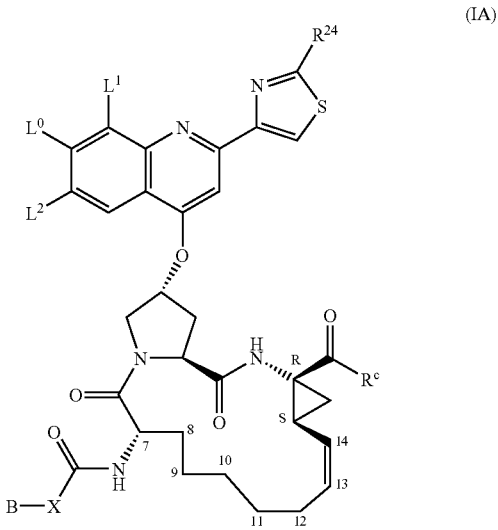

(IA)

wherein
B is $(C_{1-10})$alkyl, $(C_{3-7})$cycloalkyl or $(C_{1-4})$alkyl-$(C_{3-7})$cycloalkyl,
 a) wherein each said cycloalkyl, and alkyl-cycloalkyl may be mono-, di- or tri-substituted with $(C_{1-3})$alkyl; and
 b) wherein each said alkyl, cycloalkyl, and alkyl-cycloalkyl may be mono- or di-substituted with substituents each independently selected from hydroxy and O—$(C_{1-6})$alkyl; and
 c) wherein each of said alkyl groups may be mono-, di- or tri-substituted with halogen; and
 d) wherein in each of said cycloalkyl groups being 5-, 6- or 7-membered, one or two —CH₂-groups not being directly linked to each other may be replaced by —O—;
X is O or NH;
L⁰ is OH, —O—$(C_{1-4})$alkyl, —NH₂, —NH$(C_{1-4})$alkyl or —N$((C_{1-4})$alkyl$)_2$;
L¹, L² are each independently halogen, $(C_{1-4})$alkyl, or —O—$(C_{1-4})$alkyl; and
either L¹ or L² (but not both at the same time) may also be H; or
L⁰ and L¹ or L⁰ and L² may be covalently bonded to form, together with the two C-atoms to which they are linked, a 4-, 5- or 6-membered carbocyclic ring wherein one —OH₂-group and, in the case of 5- or 6-membered ring, one or two —CH₂-groups not being directly linked to each other, may be replaced each independently by —O— or NR$^a$ to form a heterocyclic ring wherein R$^a$ is H or $(C_{1-4})$alkyl, and wherein said carbo- or heterocyclic ring is optionally mono- or di-substituted with $(C_{1-4})$alkyl;
R²⁴ is R²⁰, —NHCOR²⁰, —NHCOOR²⁰, —NHR²¹ or NHCONR²¹R²², wherein
R²⁰ is selected from $(C_{1-8})$alkyl, $(C_{3-7})$cycloalkyl and $(C_{1-4})$alkyl-$(C_{3-7})$cycloalkyl, wherein said cycloalkyl and alkyl-cycloalkyl may be mono-, di- or tri-substituted with $(C_{1-3})$alkyl;
R²¹ is H or R²⁰ as defined above; and
R²² is H or methyl; and
R$^C$ is hydroxy or —NHSO₂R$^S$ wherein R$^S$ is $(C_{1-6})$alkyl, $(C_{3-7})$cycloalkyl, $(C_{1-6})$alkyl-$(C_{3-7})$cycloalkyl, phenyl, naphthyl, pyridinyl, $(C_{1-4})$alkyl-phenyl, $(C_{1-4})$alkyl-naphthyl or $(C_{1-4})$alkyl-pyridinyl; each of which optionally being monosubstituted with nitro; and each of which optionally being mono-, di- or tri-substituted with substituents each independently selected from halogen, hydroxy, cyano, $(C_{1-4})$alkyl, O—$(C_{1-6})$alkyl, —CO—NH₂, —CO—NH$(C_{1-4})$alkyl, —CO—N$((C_{1-4})$alkyl$)_2$, —NH₂, —NH$(C_{1-4})$alkyl and —N$((C_{1-4})$alkyl$)_2$;
or a pharmaceutically acceptable salt or ester thereof.

8. The compound according to claim 1 wherein B is selected from tert-butyl, cyclopropyl, cyclobutyl, cyclopentyl, cyclohexyl, 1-methylcyclopentyl and 1-methylcyclohexyl.

9. The compound according to claim 1 wherein B is cyclopentyl.

10. The compound according to claim 4 wherein X is O.

11. The compound according to claim 4 wherein X is NH.

12. The compound according to claim 1 wherein L⁰ is selected from —OH, —OCH₃ and —N(CH₃)₂.

13. The compound according to claim 1 wherein L¹ and L² are each independently selected from: fluorine, chlorine, bromine, —CH₃, —OCH₃, —OC₂H₅, whereby either L¹ or L², but not both at the same time, may be H.

14. The compound according to claim 13 wherein L¹ is CH₃, —F, —Cl, or —Br, and L² is H.

15. The compound according to claim 1 wherein L⁰ is —OCH₃; L¹ is OH₃, —F, —Cl, or —Br; and L² is H.

16. The compound according to claim 1 wherein R²⁴ is selected from R²⁰, —NHCOR²⁰, —NHCOOR²⁰, —NHR²¹ and NHCONR²¹R²², wherein
R²⁰ is selected from $(C_{1-8})$alkyl, $(C_{3-7})$cycloalkyl, and $(C_{1-3})$alkyl-$(C_{3-7})$cycloalkyl, wherein said cycloalkyl and alkyl-cycloalkyl may be mono-, di- or tri-substituted with $(C_{1-3})$alkyl; and
R²¹ is H or R²⁰ as defined above; and
R²² is H or methyl.

17. The compound according to claim 16 wherein R²⁴ is —NHCOR²⁰, —NHCOOR²⁰, or —NHR²¹.

18. The compound according to claim 1 wherein R²⁰ and R²¹ are each independently selected from: methyl, ethyl, n-propyl, i-propyl, n-butyl, 1-methylpropyl, 2-methylpropyl, tert-butyl, 2,2-dimethylpropyl, 1,1-dimethylpropyl, 1,2-dimethylpropyl, 1,2,2-trimethylpropyl, cyclopropyl, cyclobutyl, cyclopentyl, cyclohexyl, cyclopropylmethyl, cyclobutylmethyl, cyclopentylmethyl and cyclohexylmethyl, each of said cycloalkyl or alkylcycloalkyl groups optionally being mono- or di-substituted with methyl or ethyl.

19. The compound according to claim 18 wherein $R^{20}$ and $R^{21}$ are each independently selected from: methyl, ethyl, n-propyl, i-propyl, 2,2-dimethylpropyl and cyclopentylmethyl.

20. The compound according to claim 1 wherein $R^C$ is hydroxy.

21. The compound according to claim 1 wherein $R^C$ is —$NHSO_2R^S$
wherein $R^S$ is methyl, ethyl, n-propyl, i-propyl, n-butyl, 1-methylpropyl, 2-methylpropyl, tert-butyl, cyclopropyl, cyclobutyl, cyclopentyl, cyclohexyl, cyclopropylmethyl, cyclobutylmethyl, cyclopentylmethyl, cyclohexyl methyl, phenyl, naphthyl, pyridinyl, phenylmethyl, naphthylmethyl or pyridinylmethyl;
a) each of which optionally being mono-, di- or tri-substituted with substituents each independently selected from fluorine and methyl; and
b) each of which optionally being mono- or disubstituted with substituents each independently selected from hydroxy, and methoxy; and
c) each of which optionally being monosubstituted with a substituent selected from chlorine, bromine, cyano, nitro, —CO—$NH_2$, —CO—$NHCH_3$, —CO—N($CH_3$)$_2$, —$NH_2$, —$NH(CH_3)$ and —$N(CH_3)_2$.

22. The compound according to claim 21 wherein $R^C$ is selected from —$NHSO_2$-methyl, —$NHSO_2$-ethyl, —$NHSO_2$-(1-methyl)ethyl, —$NHSO_2$-propyl, —$NHSO_2$-cyclopropyl, —$NHSO_2$—$CH_2$-cyclopropyl, —$NHSO_2$-cyclobutyl, —$NHSO_2$-cyclopentyl, and —$NHSO_2$-phenyl.

23. The compound according to claim 22 wherein $R^C$ is —$NHSO_2$-cyclopropyl.

24. The compound according to claim 1 of formula IA:

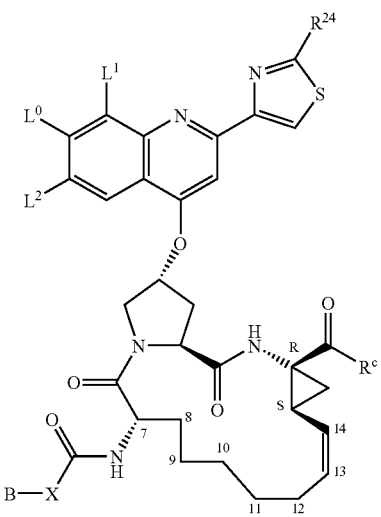

(IA)

wherein
B is cyclopentyl;
X is O;
$L^0$ is —$OCH_3$; $L^1$ is $OH_3$, —F, —Cl, or —Br; and $L^2$ is H;
$R^{24}$ is —$NHCOR^{20}$, —$NHCOOR^{20}$, or —$NHR^{21}$, wherein $R^{20}$ and $R^{21}$ are each independently selected from: methyl, ethyl, n-propyl, i-propyl, 2,2-dimethylpropyl and cyclopentylmethyl; and
$R^C$ is hydroxy.

25. The compound according to claim 1 of the formula

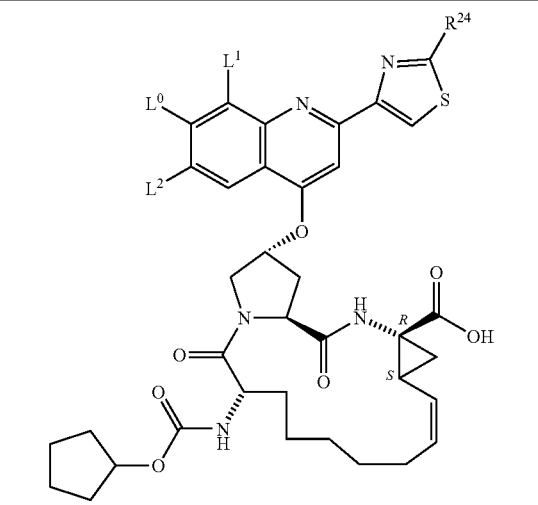

wherein $R^{24}$, $L^0$, $L^1$ and $L^2$ are defined as in the table below

| Cpd # | $L^2$ | $L^0$ | $L^1$ | $R^{24}$ |
|---|---|---|---|---|
| 101 | H | —OMe | Me | isopropylamino; |
| 102 | H | —OMe | Me | acetamido; |
| 103 | H | —OMe | Me | isobutyramido; |
| 104 | H | —OMe | Me | propionamido; |
| 105 | H | —OMe | Br | propionamido; |
| 106 | H | —OMe | Br | isopropylamino; |
| 107 | H | —OMe | Cl | isopropylamino; |
| 108 | H | —OMe | Cl | propionamido; |
| 109 | Me | —OMe | Me | isopropylamino; |

-continued

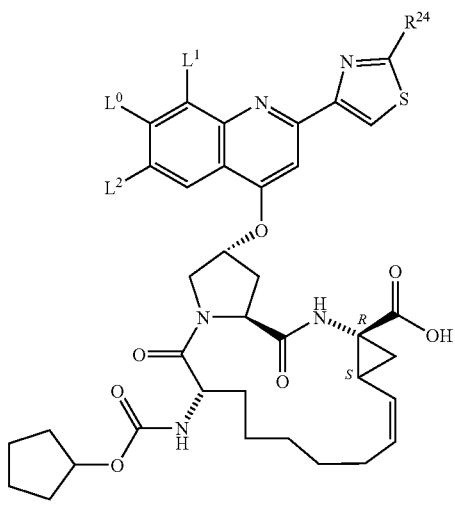

wherein R²⁴, L⁰, L¹ and L² are defined as in the table below

| Cpd # | L² | L⁰ | L¹ | R²⁴ |
|---|---|---|---|---|
| 110 | Me | —OMe | Me | -C(O)NHCH₂CH₃ ; |
| 111 | H | —OMe | F | -NHCH(CH₃)₂ ; |
| 112 | H | —OMe | F | -C(O)NHCH₂CH₃ ; |
| 113 | H | —OMe | Cl | -C(O)NHCH₂CH₂CH₃ ; |
| 114 | H | —OMe | Br | -C(O)NHCH₂CH₂CH₃ ; |
| 115 | H | —OMe | Br | -C(O)NHCH(CH₃)₂ ; or |
| 116 | H | —OMe | Br | -C(O)NHOCH(CH₃)₂ . |

26. A pharmaceutical composition comprising an anti-hepatitis C virally effective amount of a compound according to claim 1, or a pharmaceutically acceptable salt or ester thereof, and a pharmaceutically acceptable carrier medium or auxiliary agent.

27. The pharmaceutical composition according to claim 26 further comprising a therapeutically effective amount of at least one other antiviral agent.

28. The pharmaceutical composition according to claim 27, wherein said antiviral agent is ribavirin.

29. The pharmaceutical composition according to claim 27, wherein said antiviral agent is selected from another anti-HCV agent, HIV inhibitor, HAV inhibitor and HBV inhibitor.

30. The pharmaceutical composition according to claim 29, wherein said anti-HCV agent is selected from the group consisting of immunomodulatory agents, other inhibitors of HCV NS3 protease, inhibitors of HCV polymerase and inhibitors of another target in the HCV life cycle.

31. The pharmaceutical composition according to claim 30, wherein said immunomodulatory agent is selected from α-interferon and pegylated α-interferon.

32. The pharmaceutical composition according to claim 30, wherein said inhibitor of another target in the HCV life cycle is selected from inhibitors of: helicase, NS2/3 protease and internal ribosome entry site (IRES).

33. A method for treating a hepatitis C viral infection in a mammal comprising administering to the mammal an anti-hepatitis C virally effective amount of a compound according to claim 1, or a pharmaceutically acceptable salt or ester thereof.

34. A method for treating a hepatitis C viral infection in a mammal comprising administering to the mammal an anti-hepatitis C virally effective amount of a combination of a compound according to claim 1, or a pharmaceutically acceptable salt or ester thereof, and at least one other antiviral agent.

35. The method according to claim 34, wherein said antiviral agent is ribavirin.

36. The method according to claim 34, wherein said antiviral agent is selected from another anti-HCV agent, HIV inhibitor, HAV inhibitor and HBV inhibitor.

37. The method according to claim 36, wherein said anti-HCV agent is selected from immunomodulatory agents, other inhibitors of HCV NS3 protease, inhibitors of HCV polymerase and inhibitors of another target in the HCV life cycle.

38. The method according to claim 37, wherein said immunomodulatory agent is selected from α-interferon and pegylated α-interferon.

39. The method according to claim 37, wherein said inhibitor of another target in the HCV life cycle is selected from inhibitors of: helicase, NS2/3 protease and internal ribosome entry site (IRES).

40. A method of inhibiting the replication of hepatitis C virus comprising exposing the virus to a hepatitis C viral NS3 protease inhibiting amount of a compound according to claim 1, or a pharmaceutically acceptable salt or ester thereof.

41. An article of manufacture comprising a composition effective to treat an HCV infection or to inhibit the NS3 protease of HCV and packaging material comprising a label which indicates that the composition can be used to treat infection by the hepatitis C virus,
  wherein said composition comprises a compound according to claim 1 or a pharmaceutically acceptable salt or ester thereof.

42. The compound 101 according to claim 25.
43. The compound 102 according to claim 25.
44. The compound 103 according to claim 25.
45. The compound 104 according to claim 25.
46. The compound 105 according to claim 25.
47. The compound 106 according to claim 25.
48. The compound 107 according to claim 25.
49. The compound 108 according to claim 25.

50. The compound 109 according to claim 25.
51. The compound 110 according to claim 25.
52. The compound 111 according to claim 25.
53. The compound 112 according to claim 25.
54. The compound 113 according to claim 25.
55. The compound 114 according to claim 25.
56. The compound 115 according to claim 25.
57. The compound 116 according to claim 25.
58. The compound according to claim 1 of formula IA:

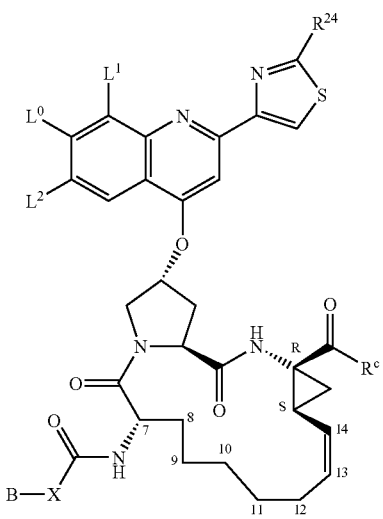

(IA)

wherein

B is cyclopentyl;

X is O or NH;

$L^0$ is —OCH$_3$; $L^1$ is CH$_3$, —F, —Cl, —Br or —OMe; and $L^2$ is H;

$R^{24}$ is —NHCOR$^{20}$, —NHCOOR$^{20}$, or —NHR$^{21}$, wherein $R^{20}$ and $R^{21}$ are each independently selected from: methyl, ethyl, n-propyl, i-propyl, 2,2-dimethylpropyl and cyclopentylmethyl; and $R^c$ is —NHSO$_2$-cyclopropyl, —NHSO$_2$-(1-methylcyclopropyl) or —NHSO$_2$N(CH$_3$)$_2$.

59. A compound according to claim 1 of the following formula:

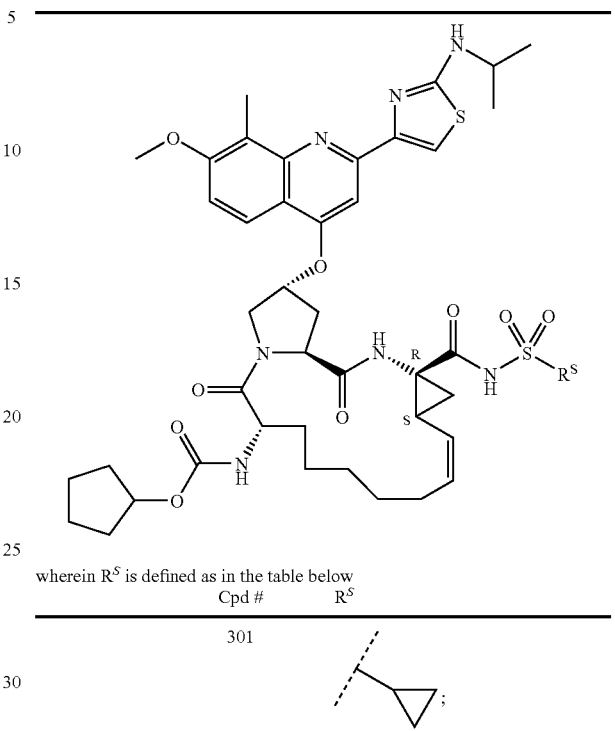

wherein $R^S$ is defined as in the table below

| Cpd # | $R^S$ |
|---|---|
| 301 | cyclopropyl |
| 302 | N,N-dimethylamino ; or |
| 303 | 1-methylcyclopropyl |

* * * * *